US012624041B2

(12) United States Patent
Li et al.

(10) Patent No.: US 12,624,041 B2
(45) Date of Patent: May 12, 2026

(54) HETEROCYCLIC COMPOUND AND USE THEREOF

(71) Applicant: WUHAN LL SCIENCE AND TECHNOLOGY DEVELOPMENT CO., LTD., Wuhan (CN)

(72) Inventors: Jinping Li, Wuhan (CN); Xiaodan Guo, Wuhan (CN); Feng Zhou, Wuhan (CN); Jun Lou, Wuhan (CN); Li Liu, Wuhan (CN); Xiaoya Chen, Wuhan (CN); Yihan Zhang, Wuhan (CN); Yongkai Chen, Wuhan (CN); Chaodong Wang, Wuhan (CN)

(73) Assignee: WUHAN LL SCIENCE AND TECHNOLOGY DEVELOPMENT CO., LTD., Wuhan (CN)

( * ) Notice: Subject to any disclaimer, the term of this patent is extended or adjusted under 35 U.S.C. 154(b) by 546 days.

(21) Appl. No.: 18/014,143

(22) PCT Filed: Jun. 23, 2021

(86) PCT No.: PCT/CN2021/101715

§ 371 (c)(1),
(2) Date: Dec. 30, 2022

(87) PCT Pub. No.: WO2022/001767

PCT Pub. Date: Jan. 6, 2022

(65) Prior Publication Data

US 2023/0257382 A1 Aug. 17, 2023

(30) Foreign Application Priority Data

Jul. 3, 2020 (CN) ......................... 202010636308.0
Dec. 11, 2020 (CN) ......................... 202011460143.2

(51) Int. Cl.
*C07D 487/04* (2006.01)
*A61P 1/16* (2006.01)

(52) U.S. Cl.
CPC .............. *C07D 487/04* (2013.01); *A61P 1/16* (2018.01)

(58) Field of Classification Search
None
See application file for complete search history.

(56) References Cited

U.S. PATENT DOCUMENTS

2011/0224193 A1 9/2011 Ting et al.
2012/0029190 A1 2/2012 Burdi et al.

FOREIGN PATENT DOCUMENTS

EP 4289846 A1 12/2023
JP 2012509333 A 4/2012
JP 2012522793 A 9/2012
WO 2019055966 A2 3/2019
WO 2019141957 A1 7/2019
WO 2019145214 A1 8/2019
WO 2019212937 A1 11/2019
WO 2020061162 A1 3/2020
WO 2020092667 A1 5/2020
WO 2020190774 A1 9/2020
WO 2020191056 A1 9/2020
WO 2020206623 A1 10/2020

OTHER PUBLICATIONS

Dec. 12, 2023 First Office Action issued in Japanese Patent Application No. 2023-500085.
Dec. 25, 2023 First Office Action issued in Eurasian Patent Application No. 202390250.
Jul. 5, 2022 Search Report issued in Chinese Patent Application No. 2021106980268.
May 14, 2024 the Second Office Action issued in Japanese Patent Application No. 2023-500085.
Jun. 10, 2024 Extended European Search Report issued in European Patent Application No. 21833850.7.
Sep. 27, 2021 International Search Report issued in International Patent Application No. PCT/CN2021/101715.
Sep. 27, 2021 Written Opinion of the International Searching Authority issued in International Patent Application No. PCT/CN2021/101715.
Shang-Zhong Xu et al., TRPC channel activation by extracellular thioredoxin, Nature, Jan. 3, 2008, vol. 451, (7174), 69-72.
Michael Dattilo et al., Inhibition of TRPC5 Channels by Intracellular ATP, Molecular Pharmacology, Feb. 2008, 73 (1), 42-49, U.S.A.
Marcus Semtner et al., Potentiation of TRPC5 by Protons, The Journal of Biological Chemistry, Nov. 16, 2007, vol. 282, No. 46, pp. 33868-33878, JBC Papers in Press, U.S.A.

(Continued)

*Primary Examiner* — Brian J Davis

(57) ABSTRACT

Disclosed is a heterocyclic compound as represented by formula (I), a tautomer thereof, or a pharmaceutically acceptable salt thereof. The compound has better inhibitory activity on TRPC5, has good metabolic stability in liver micro-particles, and has good clinical pharmacokinetic properties.

I

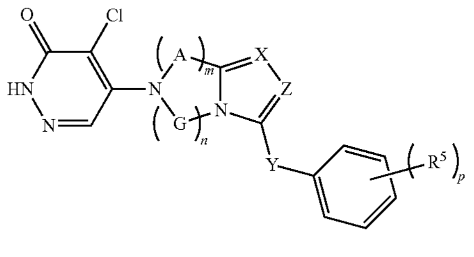

21 Claims, 1 Drawing Sheet

(56) References Cited

OTHER PUBLICATIONS

Min Ji Kim et al., Molecular determinant of sensing extracellular pH in classical transient receptor potential channel 5, Biochemical and Biophysical Research Communications, Jan. 11, 2008, 365 (2) 239-245.

Erik W. Bush et al., Canonical Transient Receptor Potential Channels Promote Cardiomyocyte Hypertrophy through Activation of Calcineurin Signaling, The Journal of Biological Chemistry, Nov. 3, 2006, vol. 281, No. 44, pp. 33487-33496, JBC Papers in Press, U.S.A.

Junko Yoshida et al., Capacitative Ca2+ entries and mRNA expression for TRPC1 and TRPC5 channels in human epidermoid carcinoma A431 cells, European Journal of Pharmacology, Mar. 14, 2005, 510 (3), 217-222.

Philippa K. Flemming et al., Sensing of Lysophospholipids by TRPC5 Calcium Channel, The Journal of Biological Chemistry, Feb. 24, 2006, vol. 281, No. 8, pp. 4977-4982, JBC Papers in Press, U.S.A.

D. J. Beech, Bipolar phospholipid sensing by TRPC5 calcium channel, Biochemical Society Transactions, Jan. 22, 2007, 35 (1), 101-104, Portland Press.

D. J. Beech, Canonical Transient Receptor Potential 5, Handbook of Experimental Pharmacology, Feb. 2007, 179, 109-123.

Li-Ping He et al., A Functional Link between Store-operated and TRPC Channels Revealed by the 3,5-Bis (trifluoromethyl)pyrazole Derivative, BTP2, the Journal of Biological Chemistry, Mar. 25, 2005, vol. 280, No. 12, pp. 10997-11006, JBC Papers in Press, U.S.A.

Shunichi Shimizu et al., Ca2+-calmodulin-dependent myosin light chain kinase is essential for activation of TRPC5 channels expressed in HEK293 cells, J Physiol, Jan. 15, 2006, 570. 2, 219-235.

Anna Greka et al., TRPC5 is a regulator of hippocampal neurite length and growth cone morphology, Nature Neuroscience, Aug. 2003, 6 (8), 837-845.

Yiming Zhou et al., A small-molecule inhibitor of TRPC5 ion channels suppresses progressive kidney disease in animal models, Science, Dec. 8, 2017, 358 (6368), 1332-1336.

Stefan Just et al., Treatment with HC-070, a potent inhibitor of TRPC4 and TRPC5, leads to anxiolytic and antidepressant effects in mice, PLOS One, Jan. 31, 2018, 13 (1): e0191225.

Jenny Bröker-Lai et al., Heteromeric channels formed by TRPC1, TRPC4 and TRPC5 define hippocampal synaptic transmission and working memory, The EMBO Journal, Published online: Aug. 8, 2017, 36 (18), 2770-2789.

Jul. 11, 2022 Chinese First Office Action issued in Chinese Patent Application No. 202110698026.8.

Stephen M. Berge et al., Pharmaceutical Salts, Journal of Pharmaceutical Sciences, Jan. 1977, vol. 66, No. 1, pp. 1-19.

Feb. 3, 2025 First Office Action issued in Korean Patent Application No. 10-2023-7002997.

Feb. 5, 2025 First Office Action issued in New Zealand Patent Application No. 796819.

Feb. 13, 2025 First Office Action issued in Taiwanese Patent Application No. 110124451.

Jun. 2, 2025 First Office Action issued in Canadian Patent Application No. 3,184,594.

Dec. 31, 2025 First Office Action issued in Indian Patent Application No. 202317004165.

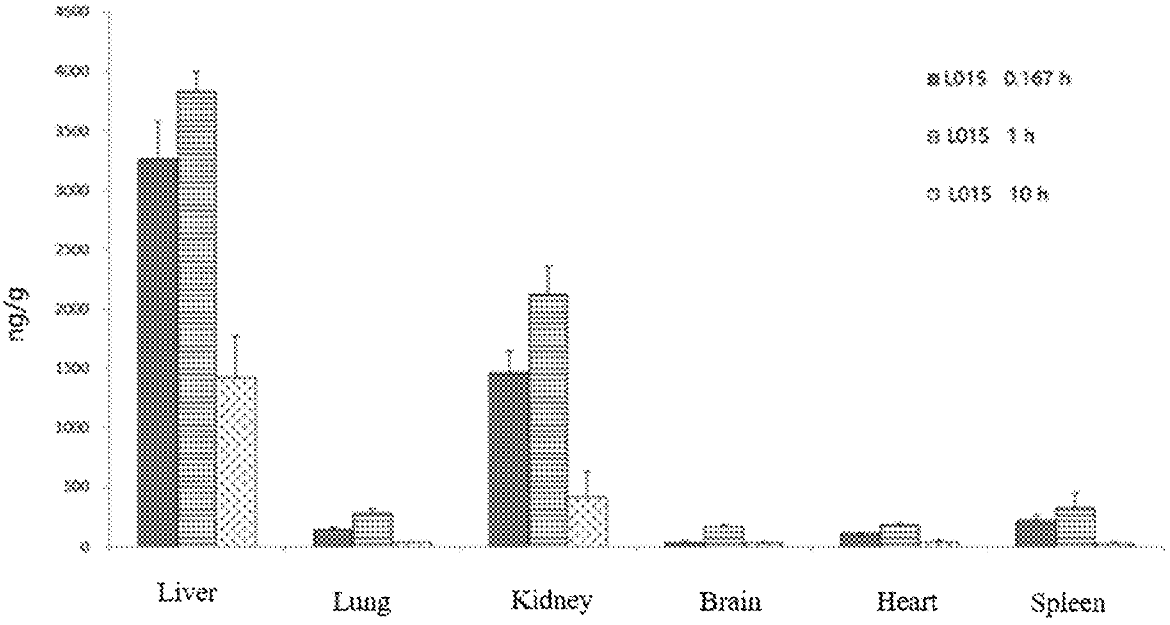
L015 0.167 h
L015 1 h
L015 10 h
ng/g
Liver
Lung
Kidney
Brain
Heart
Spleen

HETEROCYCLIC COMPOUND AND USE THEREOF

The present application claims the right of the priorities of Chinese patent application 2020106363080 filed on Jul. 3, 2020 and Chinese patent application 2020114601432 filed on Dec. 11, 2020. The contents of the above Chinese patent application are incorporated herein by reference in its entireties.

TECHNICAL FIELD

The present disclosure related to a heterocyclic compound and a use thereof.

BACKGROUND

There are various ion channel proteins to regulate the ion flow through the cell membrane. The proper expression and function of ion channel protein are important for the maintenance of cell function and intracellular communication. Many diseases are caused by abnormal regulation of membrane potential or abnormal calcium treatment. Given the central importance of ion channels in the regulation of membrane potential and ion flow in cells, the identification of agents that can promote or inhibit specific ion channels is of great interest as research tools and as possible therapeutic agents.

TRPC (Transient Receptor Potential Canonical) is one of the most important subfamilies in the TRP superfamily, including TRPC1-7, wherein, TRPC2 is a pseudogene and is not expressed in humans. According to amino acid sequence homology and structural characteristics, TRPCs can be divided into two subclasses: TRPC1, 4, 5 are classified as a subclass, and TRPC3, 6, 7 are classified as a subclass. According to the activation mode, functional TRPC can be divided into store-operated calcium channel and receptor-operated calcium channel. Both modes of activation of TRPC channels behave as nonspecific cation channels that mediate sodium and calcium influx and potassium efflux.

Cation channels (such as transient receptor potential (TRP) cation channel subfamily C, member 5 (TRP5)) regulate the flow of calcium and sodium ions through cell membranes. The influx of sodium and calcium leads to depolarization of cells. This increases the likelihood that voltage-gated ion channels will reach the threshold required for activation. Thus, activation of non-selective cation channels increases electrical excitability and increases the frequency of voltage-dependent events. Voltage-dependent events include, but are not limited to, neuronal action potential, cardiac action potential, smooth muscle contraction, cardiac muscle contraction and skeletal muscle contraction.

Calcium influx caused by activation of non-selective cation channels (such as TRPC5) also alters intracellular free calcium concentration. Calcium is a ubiquitous second messenger molecule in cells, and the change in intracellular calcium level has a profound effect on signal transduction and gene expression. Therefore, activation of non-selective cation channels (such as TRPC5) can lead to changes in gene expression and cell phenotype. Gene expression events include, but are not limited to, the production of mRNA encoding cell surface receptors, ion channels and kinases. These changes in gene expression can lead to the hyperexcitability of this cell.

Homomeric TRPC5 ion channels are signaling-gated, $Ca^{2+}$-permeable channels expressed primarily in neurons.

TRPC5 forms homomeric multi-subunit structures (such as tetramers (i.e., TRPC5 homomultimers)) and heteromeric multi-subunit structures (such as tetramers (such as TRPC5-TRPC1 heteromultimers)). Unless otherwise specified, when the term TRPC5 is used herein (for example, when identifying modulators of TRPC5, such as TRPC5 antagonists), the term TRPC5 is generally used to include one or both of TRPC5 homomultimers or heteropolymers (such as TRPC5-TPRC1 or TRPC5-TRPC4 heteropolymers). Examples of TRPC5 in the literature include the following: Nature., Jan. 3, 2008; 451(7174): 69-72; Mol Pharmacol. January 2008; 73(1): 42-9; J Biol Chem. Nov. 16, 2007; 282(46): 33868-78; Biochem Biophys Res Commun. Jan. 11, 2008; 365(2): 239-45; J Biol Chem. Nov. 3, 2006; 281(44): 33487-96; Eur J Pharmacol. Mar. 14, 2005; 510(3): 217-22; J Biol Chem. Feb. 24, 2006; 281(8): 4977-82; Biochem Soc Trans. February 2007; 35 (Pt 1): 101-4; Handb Exp Pharmacol. 2007; (179): 109-23; J Biol Chem. Mar. 25, 2005; 280(12): 10997-1006; J Physiol. Jan. 15, 2006; 570 (Pt 2): 219-35; and Nat Neurosci. (2003) 6:837-45.

Modulating the function of the TRPC5 protein provides methods for modulating calcium homeostasis, sodium homeostasis, membrane polarization, and/or intracellular calcium level, and the compound that can modulate TRPC5 function are useful in many ways, including but not limited to maintaining calcium homeostasis, regulating intracellular calcium level, modulation of membrane polarization, and treatment or prevention of diseases, disorders or conditions associated with calcium and/or sodium homeostasis or dyshomeostasis.

The compound that inhibits TRPC5 containing ion channels is, for example, suitable for treating diseases by regulating the activity of transient receptor potential cation channel subfamily C, member 5 (TRPC5) which can be in the form of homomultimer and heteropolymer with other ion channels (such as TRPC1 or TRPC3), i.e., TRPC5-TRPC1 and TRPC1-TRPC3-TRPC5.

Focal segmental glomerulosclerosis (FSGS) is a clinicopathological syndrome, clinically manifested as massive proteinuria or nephrotic syndrome, and it is pathologically characterized by foot process fusion or disappearance caused by focal segmental distribution of glomerulosclerosis lesions and podocyte degeneration. FSGS accounts for about 5% to 10% of adult nephrotic syndrome in China, and patients are more common in young adult male. 50% or more of patients with persistent nephrotic syndrome progress to end-stage nephropathy within 5 to 10 years.

In healthy glomeruli, TRPC5 is isolated in cytoplasm, maintaining normal filtration barrier, and when podocyte is injured, podocyte injury activates RACI, causing TRPC5 to transfer from cytoplasm to cell membrane, which promotes the influx of calcium ions through TRPC5 channel induced by AT1 receptor, and further promotes RAC1 activity, and RACI activation induces actin recombination and podocyte detachment from glomerulus, and then the loss of podocytes breaks the filter barrier, causing the serum protein to leak into the urine.

The currently clinically used FSGS drugs are mainly hormones, immunosuppressants, CNIs and alkylating agents, all of which have serious side effects, and many of them need to be used in combination with other drugs to be effective, and are prone to relapse.

CONTENT OF THE PRESENT INVENTION

The technical problem to be solved by the present disclosure is that the existing TRPC5 inhibitor has a single structure, for this purpose, the present disclosure provides a heterocyclic compound and a use thereof. The compound has better inhibitory activity on TRPC5, has good metabolic stability in liver microsomes, and has good clinical pharmacokinetic properties.

The present disclosure provides a heterocyclic compound represented by formula I, a tautomer thereof, a pharmaceutically acceptable salt thereof, a solvate thereof or a solvate of the pharmaceutically acceptable salt thereof;

I

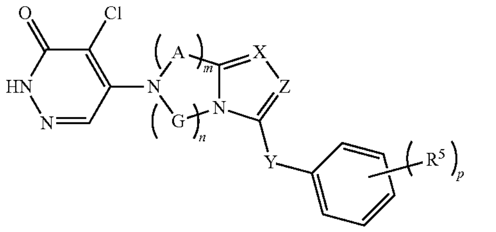

wherein, m is 1 or 2;

A is independently —($CR^1R^2$)— or —(C═O)—;

$R^1$ is independently hydrogen, halogen, $R^{1-1}$, "$R^{1-2}$ substituted by one, two or more $R^{1-3}$", —(C═O)$NHR^{1-4}$, —NH(C═O)$R^{1-5}$, —(C═O)$OR^{1-6}$, —S(═O)$_2R^{1-7}$, or —S(═O)$R^{1-8}$;

$R^{1-1}$ and $R^{1-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S" —$C_1$-$C_{40}$ alkyl;

$R^{1-3}$, $R^{1-4}$, $R^{1-5}$, $R^{1-6}$, $R^{1-7}$ and $R^{1-8}$ are independently —CN, halogen, —OH, —$NH_2$, —COOH, —$NO_2$, —S(═O)$_2CH_3$, —C(═O)$NHCH_2CH_3$, oxo (═O), —NHC(═O)$R^{1-3-4}$, —C(═O)$OR^{1-3-5}$, $R^{1-3-1}$, or "$R^{1-3-2}$ substituted by one, two or more $R^{1-3-33}$";

$R^{1-3-1}$ and $R^{1-3-2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{1-3-3}$ is independently —CN, halogen, —OH, —$NH_2$, oxo (═O), —S(═O)$_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{1-3-4}$ is independently hydrogen, $R^{1-3-41}$, or "$R^{1-3-4-2}$ substituted by one, two or more $R^{1-3-4-3}$";

$R^{1-3-4-1}$ and $R^{1-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{1-3-4-3}$ is independently —CN, halogen, —OH, —$NH_2$, oxo (═O), —S(═O), $CH_3$, $C_2$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{1-3-5}$ is independently hydrogen, $R^{1-3-5-1}$, or "$R^{1-3-5-2}$ substituted by one, two or more $R^{1-3-5-3}$";

$R^{1-3-5-1}$ and $R^{1-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{1-3-5-3}$ is independently —CN, halogen, —OH, —$NH_2$, oxo (═O), —S(═O)$_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^2$ is independently hydrogen, halogen, $R^{2-1}$, "$R^{2-2}$ substituted by one, two or more $R^{2-3}$", —(C═O)$NHR^{2-4}$, —NH(C═O)$R^{2-5}$, —(C═O)$OR^{2-6}$, —S(═O)$_2R^{2-7}$, or —S(═O)$R^{2-8}$;

$R^{2-1}$ and $R^{2-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S"—$C_1$-$C_{40}$ alkyl;

$R^{2-3}$, $R^{2-4}$, $R^{2-5}$, $R^{2-6}$, $R^{2-7}$ and $R^{2-8}$ are independently —CN, halogen, —OH, —$NH_2$, —COOH, —$NO_2$, —S(═O)$_2CH_3$, —C(═O)$NHCH_2CH_3$, oxo (═O), —NHC(═O)$R^{2-3-4}$, —C(═O)$OR^{2-3-5}$, $R^{2-3-1}$, or "$R^{2-3-2}$ substituted by one, two or more $R^{2-3-3}$";

$R^{2-3-1}$ and $R^{2-3-2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{2-3-3}$ is independently —CN, halogen, —OH, —$NH_2$, oxo (═O), —S(═O)$_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{2-3-4}$ is independently hydrogen, $R^{2-3-4-1}$, or "$R^{2-3-42}$ substituted by one, two or more $R^{2-3-4-3}$";

$R^{2-3-4-1}$ and $R^{2-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{2-3-4-3}$ is independently —CN, halogen, —OH, —$NH_2$, oxo (═O), —S(═O)$_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{2-3-5}$ is independently hydrogen, $R^{2-3-5-1}$, or "$R^{2-3-5-2}$ substituted by one, two or more $R^{2-3-5-3}$";

$R^{2-3-5-1}$ and $R^{2-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{2\text{-}3\text{-}5\text{-}3}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

n is 1 or 2;

G is independently —($CR^3R^4$)— or —(C═O)—;

$R^3$ is independently hydrogen, halogen, $R^{3\text{-}1}$, "$R^{3\text{-}2}$ substituted by one, two or more $R^{3\text{-}3}$", —(C═O)NH$R^{3\text{-}4}$, —NH(C═O)$R^{3\text{-}5}$, —(C═O)O$R^{3\text{-}6}$, —S(═O)$_2R^{3\text{-}7}$, or —S(═O)$R^{3\text{-}8}$;

$R^{3\text{-}1}$ and $R^{3\text{-}2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S"—$C_1$-$C_4$ alkyl;

$R^{3\text{-}3}$, $R^{3\text{-}4}$, $R^{3\text{-}5}$, $R^{3\text{-}6}$, $R^{3\text{-}7}$ and $R^{3\text{-}8}$ are independently —CN, halogen, —OH, —$NH_2$, —COOH, —$NO_2$, —S(═O) ¿CH$_3$, —C(═O)NHCH$_2$CH$_3$, oxo (═O), —NHC(═O)$R^{3\text{-}3\text{-}4}$, —C(═O)O$R^{3\text{-}3\text{-}5}$, $R^{3\text{-}3\text{-}1}$, or "$R^{3\text{-}3\text{-}2}$ substituted by one, two or more $R^{3\text{-}3\text{-}3}$";

$R^{3\text{-}3\text{-}1}$ and $R^{3\text{-}3\text{-}2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{3\text{-}3\text{-}3}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{3\text{-}3\text{-}4}$ is independently hydrogen, $R^{3\text{-}3\text{-}4\text{-}1}$, or "$R^{3\text{-}3\text{-}4\text{-}2}$ substituted by one, two or more $R^{3\text{-}3\text{-}4\text{-}3}$";

$R^{3\text{-}3\text{-}4\text{-}1}$ and $R^{3\text{-}3\text{-}4\text{-}2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{3\text{-}3\text{-}4\text{-}3}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{3\text{-}3\text{-}5}$ is independently hydrogen, $R^{3\text{-}3\text{-}5\text{-}1}$, or "$R^{3\text{-}3\text{-}5\text{-}2}$ substituted by one, two or more $R^{3\text{-}3\text{-}5\text{-}3}$";

$R^{3\text{-}3\text{-}5\text{-}1}$ and $R^{3\text{-}3\text{-}5\text{-}2}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{3\text{-}3\text{-}5\text{-}3}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^4$ is independently hydrogen, halogen, $R^{4\text{-}1}$, "$R^{4\text{-}2}$ substituted by one, two or more $R^{4\text{-}3}$", —(C═O)NH$R^{4\text{-}4}$, —NH(C═O)$R^{4\text{-}5}$, —(C═O)O$R^{4\text{-}6}$, —S(═O)$_2R^{4\text{-}7}$, or —S(═O)$R^{4\text{-}8}$;

$R^{4\text{-}1}$ and $R^{4\text{-}2}$ are independently amino, $C_1$-$C_{40}$ alkyl, $C_2$-$C_{46}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S"—$C_1$-$C_{40}$ alkyl;

$R^{4\text{-}3}$, $R^{44}$, $R^{45}$, $R^{46}$, $R^{4\text{-}7}$ and $R^{4\text{-}8}$ are independently —CN, halogen, —OH, —$NH_2$, —COOH, —$NO_2$, —S(═O)$_2$CH$_3$, —C(═O)NHCH$_2$CH$_3$, oxo (═O), —NHC(═O)$R^{4\text{-}3\text{-}4}$, —C(═O)O$R^{4\text{-}3\text{-}5}$, $R^{4\text{-}3\text{-}1}$, or "$R^{4\text{-}3\text{-}2}$ substituted by one, two or more $R^{4\text{-}3\text{-}3}$";

$R^{4\text{-}3\text{-}1}$ and $R^{4\text{-}3\text{-}2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{4\text{-}3\text{-}3}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{4\text{-}3\text{-}4}$ is independently hydrogen, $R^{4\text{-}3\text{-}4\text{-}1}$, or "$R^{4\text{-}3\text{-}4\text{-}2}$ substituted by one, two or more $R^{4\text{-}3\text{-}4\text{-}3}$";

$R^{4\text{-}3\text{-}4\text{-}1}$ and $R^{4\text{-}3\text{-}4\text{-}2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{4\text{-}3\text{-}4\text{-}3}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{4\text{-}3\text{-}5}$ is independently hydrogen, $R^{4\text{-}3\text{-}5\text{-}1}$, or "$R^{4\text{-}3\text{-}5\text{-}2}$ substituted by one, two or more $R^{4\text{-}3\text{-}5\text{-}3}$";

$R^{4\text{-}3\text{-}5\text{-}1}$ and $R^{4\text{-}3\text{-}5\text{-}2}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{4\text{-}3\text{-}5\text{-}3}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

X is N or CH;

when X is N, Z is $CR^6$; when X is CH, Z is N or $CR^7$;

Re is hydrogen, halogen, amino, $C_1$-$C_4$ alkyl substituted by one or more $R^{6\text{-}2}$, $C_1$-$C_4$ alkoxy or —C(═O)—NH—$R^{6\text{-}1}$; $R^{6\text{-}1}$ is $C_1$-$C_4$ alkyl; $R^{6\text{-}2}$ is independently —CN, halogen, —OH, —$NH_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^7$ is hydrogen, halogen, amino, $C_1$-$C_4$ alkyl substituted by one or more $R^{7-2}$, $C_1$-$C_4$ alkoxy or —C(═O)—NH—$R^{7-1}$; $R^{7-1}$ is $C_1$-$C_4$ alkyl; $R^{7-2}$ is independently —CN, halogen, —OH, —NH$_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

Y is —O—, —S—, —NR$^8$—, —CH$_2$—, —C(═O)— or —S(═O)—;

$R^8$ is hydrogen, $C_1$-$C_4$ alkyl substituted by one or more $R^{8-2}$, $C_1$-$C_4$ alkoxy or —C(═O)—NH—$R^{8-1}$; $R^{8-1}$ is $C_1$-$C_4$ alkyl; $R^{8-2}$ is independently —CN, halogen, —OH, —NH$_2$, oxo (═O), —S(═O)$_2$CH$_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

p is 1, 2 or 3;

$R^5$ is independently cyano, halogen, —OH, $C_1$-$C_4$ alkyl, $C_1$-$C_4$ alkoxy, —NR$^9$R$^{10}$, $C_3$-$C_6$ cycloalkyl, or $C_1$-$C_4$ alkyl substituted by one or more halogens;

$R^9$ and $R^{10}$ are independently H or $C_1$-$C_4$ alkyl.

In a certain embodiment, the heterocyclic compound represented by formula I is represented by formula II or formula III:

II

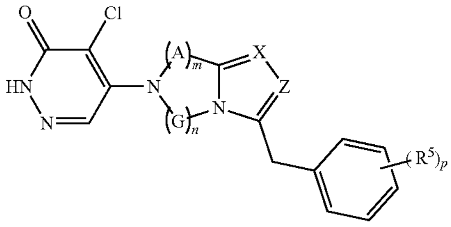

or

III

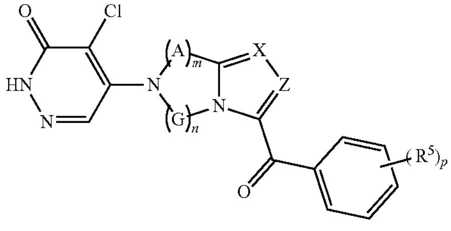

wherein, the definitions of A, X, Z, G, $R^5$, m, n and p are all as described in any one of the embodiments.

In a certain embodiment, the heterocyclic compound represented by formula I is represented by formula IV or formula V:

IV

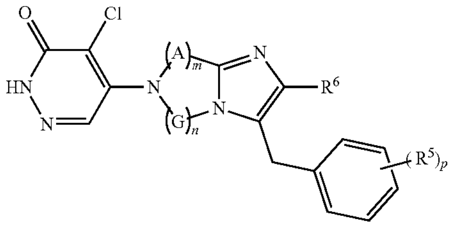

or

-continued

V

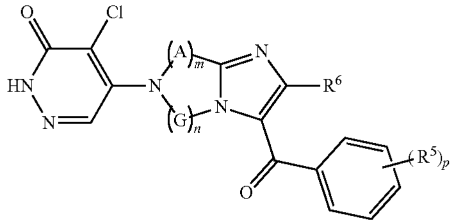

wherein, the definitions of A, G, $R^5$, $R^6$, m, n and p are all as described in any one of the embodiments.

In a certain embodiment, the heterocyclic compound represented by formula I is represented by formula VI or formula VII:

VI

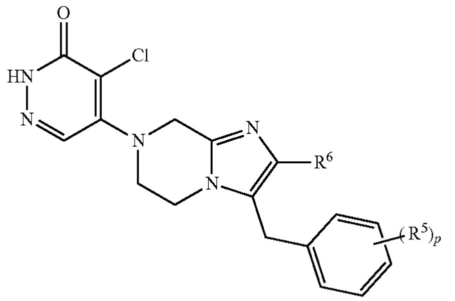

or

VII

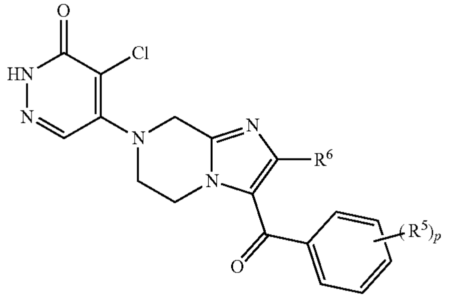

wherein, the definitions of $R^5$, $R^6$ and p are all as described in any one of the embodiments.

In a certain embodiment, some groups in the heterocyclic compound represented by formula I, the tautomer thereof, the pharmaceutically acceptable salt thereof, the solvent thereof or the solvent of the pharmaceutically acceptable salt thereof have the following definitions, and unmentioned groups are defined as described in any one of the above embodiments (this paragraph is hereinafter referred to as "in a certain embodiment"):

m is 1 or 2;

A is independently —(CR$^1$R$^2$)—;

$R^1$ is independently hydrogen or $R^{1-1}$; $R^{1-1}$ is independently $C_1$-$C_{40}$ alkyl;

$R^2$ is hydrogen;

n is 2;

G is independently —(CR$^3$R$^4$)—;

$R^3$ is independently hydrogen, $R^{3-1}$, or "$R^{3-2}$ substituted by one, two or more $R^{3-3}$"; $R^{3-1}$ and $R^{3-2}$ are independently $C_1$-$C_{40}$ alkyl; $R^{3-3}$ is —OH;

$R^4$ is hydrogen;

X is N, Z is CR$^6$; or X is CH, Z is N;

$R^6$ is hydrogen, halogen or —C(═O)—NH—$R^{6-1}$; $R^{6-1}$ is $C_1$-$C_4$ alkyl;
Y is —O—, —S—, —$NR^8$—, —$CH_2$—, —C(═O)— or —S(═O)—; $R^8$ is hydrogen;
p is 1 or 2;
$R^5$ is independently cyano, halogen, —OH, $C_1$-$C_4$ alkyl, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently $C_1$-$C_4$ alkyl.

In a certain embodiment,
m is 1 or 2;
A is independently —($CR^1R^2$)—;
$R^1$ is independently hydrogen or $R^{1-1}$; $R^{1-1}$ is independently $C_1$-$C_{40}$ alkyl;
$R^2$ is hydrogen;
n is 2;
G is independently —($CR^3R^4$)—;
$R^3$ is independently hydrogen, $R^{3-1}$, or "$R^{3-2}$ substituted by one, two or more $R^{3-3}$"; $R^{3-1}$ and $R^{3-2}$ are independently $C_1$-$C_{40}$ alkyl; $R^{3-3}$ is —OH;
$R^4$ is hydrogen;
X is N and Z is $CR^6$;
$R^6$ is hydrogen, halogen or —C(═O)—NH—$R^{6-1}$; $R^{6-1}$ is $C_1$-$C_4$ alkyl;
Y is —$NR^8$— or —$CH_2$—; $R^8$ is hydrogen;
p is 1 or 2;
$R^5$ is independently halogen, or $C_1$-$C_4$ alkyl substituted by one or more halogens.

In a certain embodiment:
m is 1 or 2;
A is —($CR^1R^2$)—;
$R^1$ is hydrogen;
$R^2$ is hydrogen;
n is 2;
G is —($CR^3R^4$)—;
$R^3$ is hydrogen;
$R^4$ is hydrogen;
X is N and Z is $CR^6$;
$R^6$ is hydrogen, halogen or —C(═O)—NH—$R^{6-1}$; $R^{6-1}$ is $C_1$-$C_4$ alkyl;
Y is —$NR^8$— or —$CH_2$—; $R^8$ is hydrogen;
p is 1 or 2;
$R^5$ is independently halogen, or $C_1$-$C_4$ alkyl substituted by one or more halogens.

In a certain embodiment:
m is 1;
A is —($CR^1R^2$)—;
$R^1$ is hydrogen;
$R^2$ is hydrogen;
n is 2;
G is —($CR^3R^4$)—;
$R^3$ is hydrogen;
$R^4$ is hydrogen;
X is N and Z is $CR^6$;
$R^6$ is hydrogen;
Y is —$CH_2$—;
p is 1 or 2;
$R^5$ is independently halogen, or $C_1$-$C_4$ alkyl substituted by one or more halogens.

In a certain embodiment:
m is 1 or 2;
A is —($CR^1R^2$)—;
$R^1$ is independently hydrogen or $R^{1-1}$; $R^{1-1}$ is independently $C_1$-$C_{40}$ alkyl;
$R^2$ is hydrogen;
n is 2;
G is —($CR^3R^4$)—;
$R^3$ is independently hydrogen, $R^{3-1}$, or "$R^{3-2}$ substituted by one, two or more $R^{3-3}$"; $R^{3-1}$ and $R^{3-2}$ are independently $C_1$-$C_{40}$ alkyl; $R^{3-3}$ is —OH;
$R^4$ is hydrogen;
X is N and Z is $CR^6$;
Re is hydrogen, halogen or —C(═O)—NH—$R^{6-1}$; $R^{6-1}$ is $C_1$-$C_4$ alkyl;
Y is —$NR^8$—, —$CH_2$—, —C(═O)— or —S(═O)—; $R^8$ is hydrogen;
p is 1 or 2;
$R^5$ is independently cyano, halogen, —OH, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently $C_1$-$C_4$ alkyl.

In a certain embodiment:
m is 1 or 2;
A is —($CR^1R^2$)—;
$R^1$ is independently hydrogen or $R^{1-1}$; $R^{1-1}$ is independently methyl or ethyl;
$R^2$ is hydrogen;
n is 2;
G is —($CR^3R^4$)—;
$R^3$ is independently hydrogen, $R^{3-1}$, or "$R^{3-2}$ substituted by one, two or more $R^{3-3}$"; $R^{3-1}$ and $R^{3-2}$ are independently methyl or ethyl; $R^{3-3}$ is —OH;
$R^4$ is hydrogen;
X is N and Z is $CR^6$; or X is CH and Z is N;
$R^6$ is hydrogen, halogen or —C(═O)—NH—$R^{6-1}$; $R^{6-1}$ is methyl or ethyl;
Y is —O—, —S—, —$NR^8$—, —$CH_2$—, —C(═O)— or —S(═O)—; $R^8$ is hydrogen;
p is 1 or 2;
$R^5$ is independently cyano, halogen, —OH, methoxy, ethoxy, —$NR^9R^{10}$, cyclopropyl, methyl, difluoromethyl or trifluoromethyl; $R^9$ and $R^{10}$ are independently methyl or ethyl.

In a certain embodiment:
m is 1 or 2;
A is —($CR^1R^2$)—;
$R^1$ is independently hydrogen or $R^{1-1}$; $R^{1-1}$ is independently methyl or ethyl;
$R^2$ is hydrogen;
n is 2;
G is —($CR^3R^4$)—;
$R^3$ is independently hydrogen, $R^{3-1}$, or "$R^{3-2}$ substituted by one, two or more $R^{3-3}$"; $R^{3-1}$ and $R^{3-2}$ are independently methyl or ethyl; $R^{3-3}$ is —OH;
$R^4$ is hydrogen;
X is N and Z is $CR^5$;
$R^6$ is hydrogen, halogen or —C(═O)—NH—$R^{6-1}$; $R^{6-1}$ is methyl or ethyl;
Y is —$NR^8$—, —$CH_2$—, —C(═O)— or —S(═O)—; $R^8$ is hydrogen;
p is 1 or 2;
$R^5$ is independently cyano, halogen, —OH, methoxy, ethoxy, —$NR^9R^{10}$, cyclopropyl or methyl substituted by one or more halogens; $R^9$ and $R^{10}$ are independently methyl or ethyl.

In a certain embodiment:
m is 1;
A is —($CR^1R^2$)—;
$R^1$ is hydrogen;
$R^2$ is hydrogen;
n is 2;
G is —($CR^3R^4$)—;
$R^3$ is hydrogen;
$R^4$ is hydrogen;

X is N and Z is $CR^6$;

$R^6$ is hydrogen;

Y is —$CH_2$—, —C(=O)— or —S(=O)—;

p is 1 or 2;

$R^5$ is independently halogen, cyano, —OH, or $C_1$-$C_4$ alkyl substituted by one or more halogens.

In a certain embodiment:

m is 1;

A is —($CR^1R^2$)—;

$R^1$ is hydrogen;

$R^2$ is hydrogen;

n is 2;

G is —($CR^3R^4$)—;

$R^3$ is hydrogen;

$R^4$ is hydrogen;

X is N and Z is $CR^6$;

$R^6$ is hydrogen;

Y is —$CH_2$—, —C(=O)— or —S(=O)—;

p is 1 or 2;

$R^5$ is independently halogen, cyano, —OH, or $C_1$-$C_4$ alkyl substituted by one or more halogens; when p is 1, $R^5$ is $C_1$-$C_4$ alkyl substituted by one or more halogens; when p is 2, the $C_1$-$C_4$ alkyl substituted by one or more halogens is $C_1$-$C_4$ alkyl substituted by 3 halogens.

In a certain embodiment, m is 1;

A is —($CR^1R^2$)—;

$R^1$ is hydrogen;

$R^2$ is hydrogen;

n is 2;

G is —($CR^3R^4$)—;

$R^3$ is hydrogen;

$R^4$ is hydrogen;

X is N and Z is $CR^6$;

$R^6$ is hydrogen;

Y is —$CH_2$— or —C(=O)—;

p is 1 or 2;

$R^5$ is independently halogen, cyano, or methyl substituted by one or more halogens;

when p is 2, the $R^5$ is located at the ortho and para positions of the Y, and the methyl substituted by one or more halogens is methyl substituted by 3 halogens;

when Y is —$CH_2$—, p is 1, $R^5$ is methyl substituted by one or more halogens.

In a certain embodiment, m is 1.

In a certain embodiment, A is —($CR^1R^2$)—.

In a certain embodiment, R' is independently hydrogen or $R^{1-1}$; $R^{1-1}$ is independently $C_1$-$C_{40}$ alkyl.

In a certain embodiment, $R^1$ is independently hydrogen or $R^{1-1}$; $R^{1-1}$ is independently methyl or ethyl.

In a certain embodiment, $R^1$ is hydrogen.

In a certain embodiment, $R^2$ is hydrogen.

In a certain embodiment, n is 2.

In a certain embodiment, G is —($CR^3R^4$)—.

In a certain embodiment, $R^3$ is independently hydrogen, $R^{3-1}$, or "$R^{3-2}$ substituted by one, two or more $R^{3-3}$"; $R^{3-1}$ and $R^{3-2}$ are independently $C_1$-$C_{40}$ alkyl; $R^{3-3}$ is —OH.

In a certain embodiment, $R^3$ is independently hydrogen, $R^{3-1}$, or "$R^{3-2}$ substituted by one, two or more $R^{3-3}$"; $R^{3-1}$ and $R^{3-2}$ are independently methyl or ethyl; $R^{3-3}$ is —OH.

In a certain embodiment, $R^3$ is hydrogen.

In a certain embodiment, $R^4$ is hydrogen.

In a certain embodiment, X is N and Z is $CR^6$; $R^6$ is hydrogen, halogen or —C(=O)—NH—$R^{6-1}$; $R^{6-1}$ is $C_1$-$C_4$ alkyl.

In a certain embodiment, X is N and Z is $CR^6$; Re is hydrogen.

In a certain embodiment, X is CH and Z is N.

In a certain embodiment, Y is —O—, —S—, —$NR^8$—, —$CH_2$—, —C(=O)— or —S(=O)—; $R^8$ is hydrogen.

In a certain embodiment, Y is —$NR^8$—, —$CH_2$—, —C(=O)— or —S(=O)—; $R^8$ is hydrogen.

In a certain embodiment, Y is —$CH_2$— or —C(=O)—.

In a certain embodiment, Y is —C(=O)—.

In a certain embodiment, p is 1 or 2.

In a certain embodiment, $R^5$ is independently cyano, halogen, —OH, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently $C_1$-$C_4$ alkyl.

In a certain embodiment, $R^5$ is independently cyano, halogen, $C_1$-$C_4$ alkoxy, —$NR^9R^{10}$, $C_3$-$C_6$ cycloalkyl, or $C_1$-$C_4$ alkyl substituted by one or more halogens.

In a certain embodiment, $R^5$ is independently cyano, halogen, —OH, methoxy, ethoxy, —$N(CH_3)_2$, cyclopropyl, methyl, difluoromethyl or trifluoromethyl.

In a certain embodiment, $R^5$ is independently cyano, halogen, or $C_1$-$C_4$ alkyl substituted by one or more halogens.

In a certain embodiment, when A is independently —($CR^1R^2$)—, wherein, the carbon atoms connected to $R^1$ and $R^2$ can be carbon atoms of R-configuration and/or carbon atoms of S-configuration.

In a certain embodiment, when $R^{1-1}$ is independently $C_1$-$C_{40}$ alkyl, the $C_1$-$C_{40}$ alkyl can be $C_1$-$C_4$ alkyl, can also be methyl or ethyl.

In a certain embodiment, when G is independently —($CR^3R^4$)—, wherein, the carbon atoms connected to $R^3$ and $R^4$ can be carbon atoms of R-configuration and/or carbon atoms of S-configuration.

In a certain embodiment, when $R^{3-1}$ is independently $C_1$-$C_{40}$ alkyl, the $C_1$-$C_{40}$ alkyl can be $C_1$-$C_4$ alkyl, can also be methyl or ethyl.

In a certain embodiment, when $R^{3-2}$ is independently $C_1$-$C_{40}$ alkyl, the $C_1$-$C_4$ alkyl can be $C_1$-$C_4$ alkyl, can also be methyl or ethyl.

In a certain embodiment, when $R^3$ is independently "$R^{3-2}$ substituted by one $R^{3-3}$", the "$R^{3-2}$ substituted by one $R^{3-3}$" can be hydroxymethyl.

In a certain embodiment, when $R^6$ is halogen, the halogen can be fluorine, chlorine or bromine, can also be bromine.

In a certain embodiment, when $R^{6-1}$ is $C_1$-$C_4$ alkyl, the $C_1$-$C_4$ alkyl can be methyl, ethyl, n-propyl, isopropyl, n-butyl, isobutyl, sec-butyl or tert-butyl; can also be methyl.

In a certain embodiment, the $R^5$ can be independently located at the ortho, meta or para position of the Y.

In a certain embodiment, when p is 1, the $R^5$ can be located at the ortho position of the Y.

In a certain embodiment, when p is 2, the $R^5$ can be located at the ortho or para position of the Y.

In a certain embodiment, when p is 2, the $R^5$ can be located at the ortho or para position of the Y, or can be located at the ortho or meta position of the Y.

In a certain embodiment, when $R^5$ is independently halogen, the halogen can be fluorine, chlorine or bromine, can also be fluorine or chlorine.

In a certain embodiment, when $R^5$ is independently $C_1$-$C_4$ alkyl substituted by one or more halogens, the number of the more halogens can be 2 or 3.

In a certain embodiment, when $R^5$ is independently $C_1$-$C_4$ alkyl substituted by one or more halogens, the halogen can be fluorine, chlorine or bromine, or fluorine.

In a certain embodiment, when $R^5$ is independently $C_1$-$C_4$ alkyl substituted by one or more halogens, the $C_1$—Ca alkyl can be methyl, ethyl, n-propyl, isopropyl, n-butyl, isobutyl, sec-butyl or tert-butyl; can also be methyl.

In a certain embodiment, when $R^5$ is independently $C_1$-$C_4$ alkyl substituted by more halogens, the $C_1$-$C_4$ alkyl substituted by more halogens can be difluoromethyl or trifluoromethyl.

In a certain embodiment, when $R^5$ is independently $C_1$-$C_4$ alkoxy, the $C_1$-$C_4$ alkoxy is methoxy, ethoxy, n-propoxy, isopropyl, n-butoxy, isobutyl, sec-butoxy or tert-butoxy.

In a certain embodiment, when $R^5$ is independently $C_3$-$C_6$ cycloalkyl, the $C_3$-$C_6$ cycloalkyl is cyclopropyl, cyclobutyl, cyclopentyl or cyclohexyl.

In a certain embodiment, when $R^5$ is independently $C_3$-$C_6$ cycloalkyl, the $C_3$-$C_6$ cycloalkyl is cyclopropyl.

In a certain embodiment, the

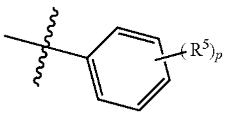

can be

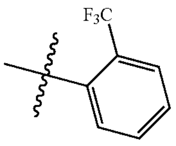,
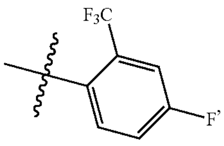
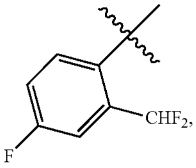,
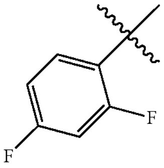,
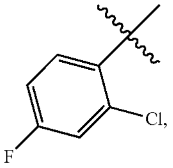,
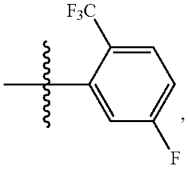,
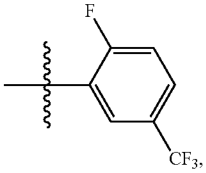,
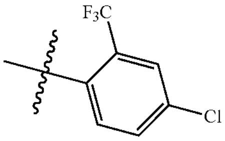,
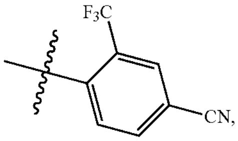,
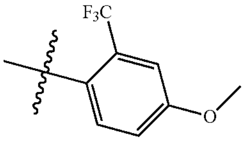,
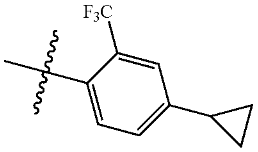,
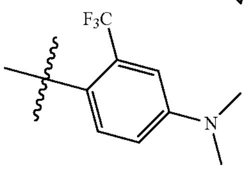,
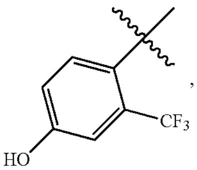, -continued

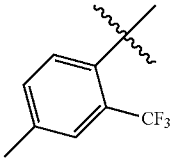 or 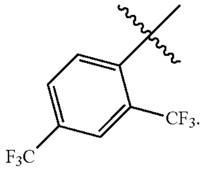.

In a certain embodiment, the

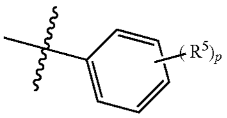

can be 2-trifluoromethylphenyl, 2-trifluoromethyl-4-fluorophenyl, 2-difluoromethyl-4-fluorophenyl, 2,4-difluorophenyl, 2-chloro-4-fluorophenyl,

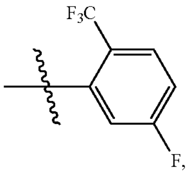,
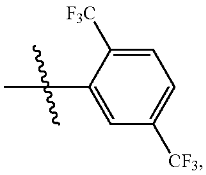,
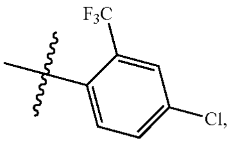,
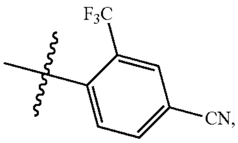,
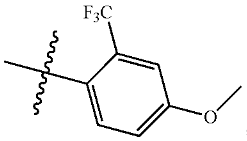,
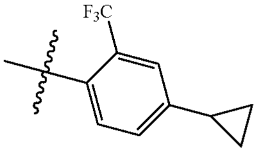 or
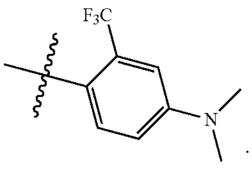.

In a certain embodiment, the

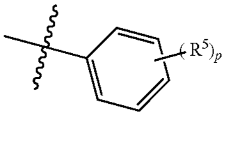

can be 2-trifluoromethylphenyl, 2-trifluoromethyl-4-fluorophenyl, 2-difluoromethyl-4-fluorophenyl, 2,4-difluorophenyl, 2-chloro-4-fluorophenyl,

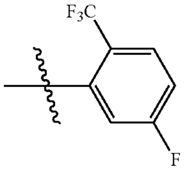
or
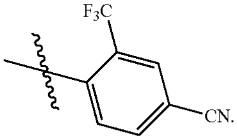
In a certain embodiment, the
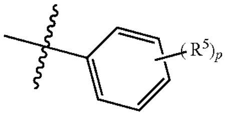
can be 2-trifluoromethylphenyl, 2-trifluoromethyl-4-fluorophenyl, 2-chloro-4-fluorophenyl,
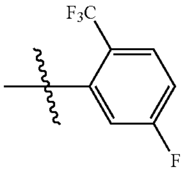
or
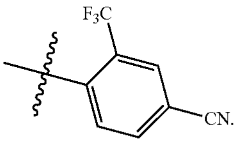
In a certain embodiment, the
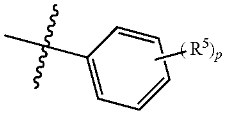
can be
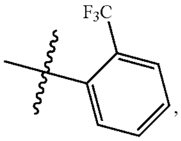
,
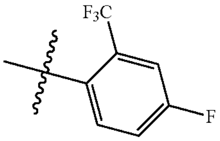
or
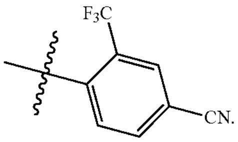
In a certain embodiment, the
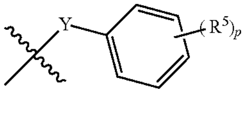
can be
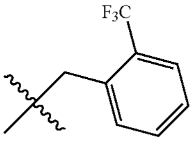
,
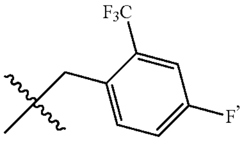
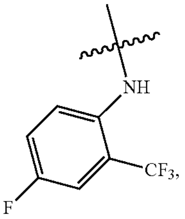
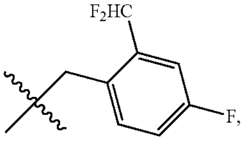
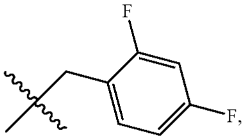
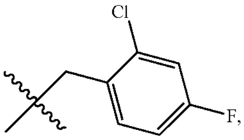
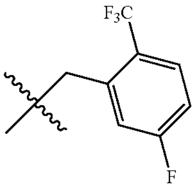
,
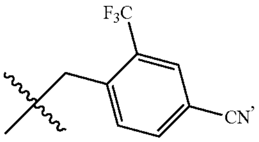
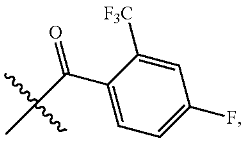
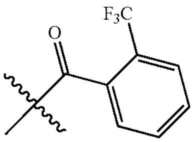
,
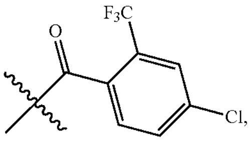
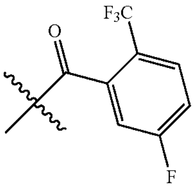
,
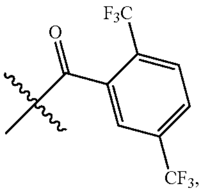
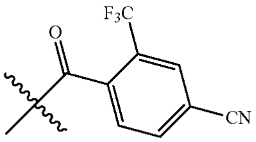
,
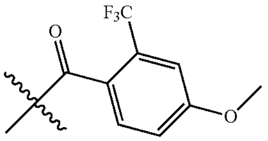
,
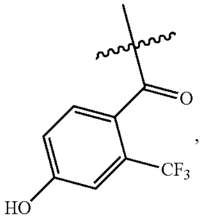
,
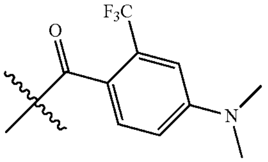
,
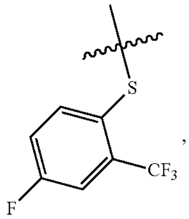
, -continued
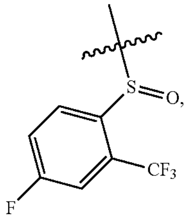
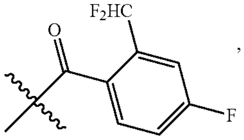
,
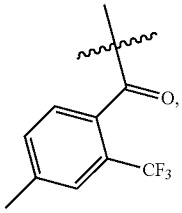
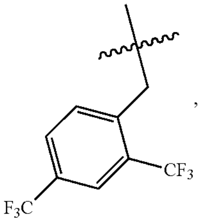
,
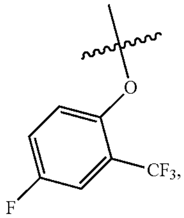
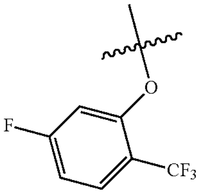
or
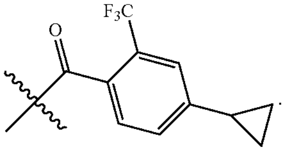
In a certain embodiment, the
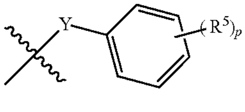
can be
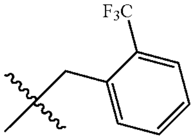
,
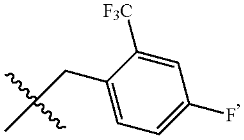
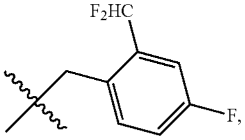
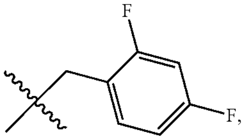
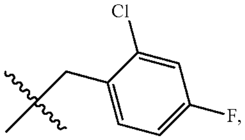
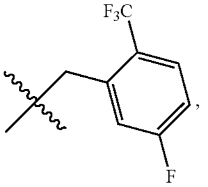
-continued
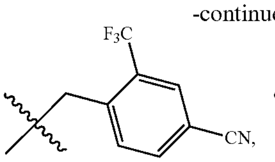
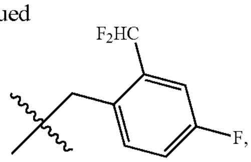
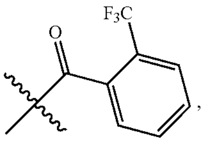
,
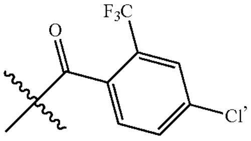
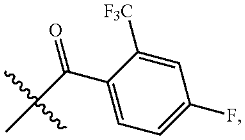
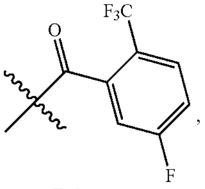
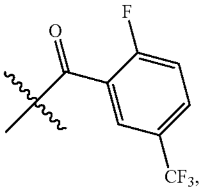
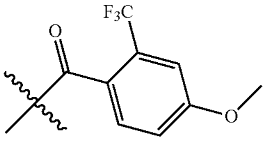
,
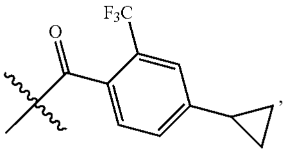
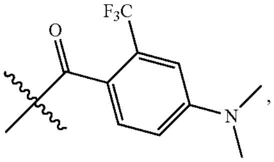
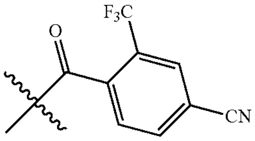
or
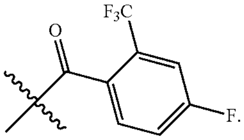
In a certain embodiment, the
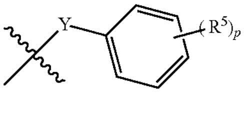
can be
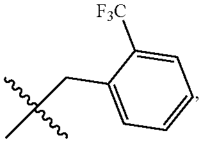
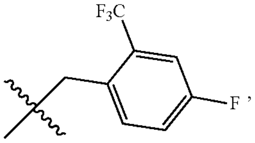

-continued

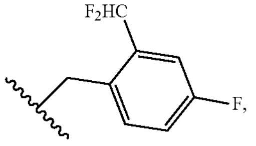

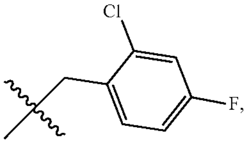

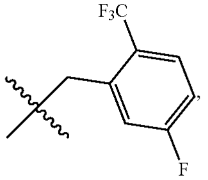

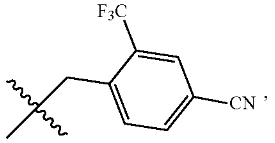

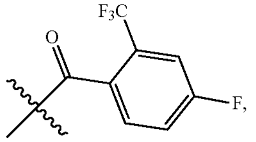

or

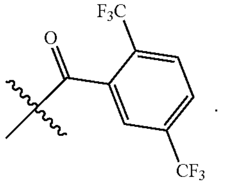

In a certain embodiment, the

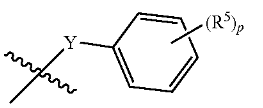

can be

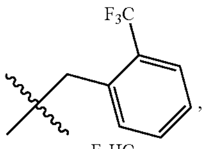

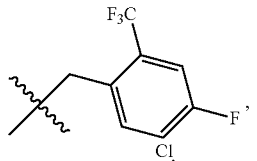

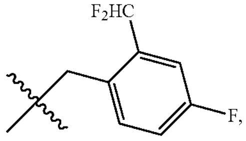

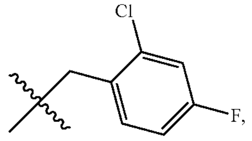

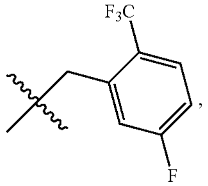

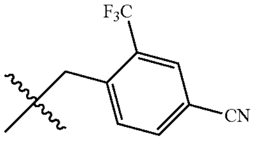

or

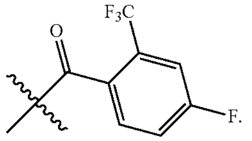

In a certain embodiment, the

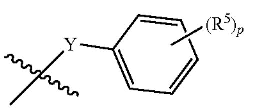

can be

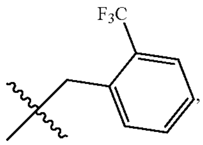

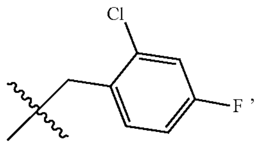

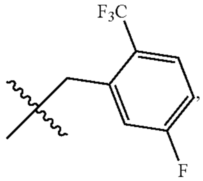

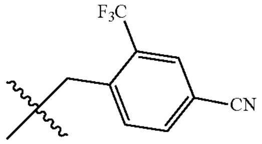

or

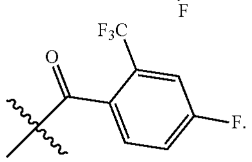

In a certain embodiment, the heterocyclic compound represented by formula I, the tautomer thereof, the pharmaceutically acceptable salt thereof, the solvate thereof or the solvate of the pharmaceutically acceptable salt thereof:

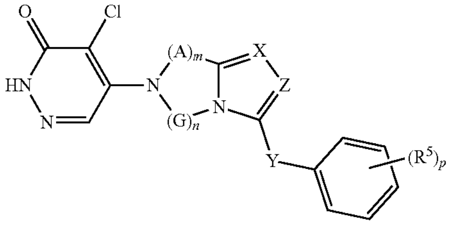

(I)

wherein, m is 1 or 2;

A is independently —$(CR^1R^2)$— or —(C═O)—;

$R^1$ is independently hydrogen, halogen, $R^{1-1}$, "$R^{1-2}$ substituted by one, two or more $R^{1-3}$". (C═O)$NHR^{1-4}$, —NH(C═O)$R^{15}$, —(C═O)$OR^{1-6}$, —S(═O)$_2R^{1-7}$, or —S(═O)$R^{1-8}$;

$R^{1-1}$ and $R^{1-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S"—$C_1$-$C_{40}$ alkyl;

$R^{1-3}$, $R^{1-4}$, $R^{1-5}$, $R^{1-6}$, $R^{1-7}$ and $R^{1-8}$ are independently —CN, halogen, —OH, —$NH_2$, —COOH, —$NO_2$, —S(═O)$_2CH_3$, —C(═O)$NHCH_2CH_3$, oxo (═O), —NHC(═O)$R^{1-3-4}$, —C(═O)$OR^{1-3-5}$, $R^{1-3-1}$, or "$R^{1-3-2}$ substituted by one, two or more $R^{1-3-3}$";

$R^{1-3-1}$ and $R^{1-3-2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{1-3-3}$ is independently —CN, halogen, —OH, —$NH_2$, oxo (═O), —S(O)$_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{1-3-4}$ is independently hydrogen, $R^{1-3-4-1}$, or "$R^{1-3-4-2}$ substituted by one, two or more $R^{1-3-4-3}$";

$R^{1-3-4-1}$ and $R^{1-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{1-3-4-3}$ is independently —CN, halogen, —OH, —$NH_2$, oxo (═O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{1-3-5}$ is independently hydrogen, $R^{1-3-5-1}$, or "$R^{1-3-5-2}$ substituted by one, two or more $R^{1-3-5-3}$";

$R^{1-3-5-1}$ and $R^{1-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{1-3-5-3}$ is independently —CN, halogen, —OH, —$NH_2$, oxo (═O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^2$ is independently hydrogen, halogen, $R^{2-1}$, "$R^{2-2}$ substituted by one, two or more $R^{2-3}$", —(C═O)$NHR^{2-4}$, —NH(C═O)$R^{2-5}$, —(C═O)$OR^{2-6}$, —S(═O)$_2R^{2-7}$, or —S(═O)$R^{2-8}$;

$R^{2-1}$ and $R^{2-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S"—$C_1$-$C_{40}$ alkyl;

$R^{2-3}$, $R^{2-4}$, $R^{2-5}$, $R^{2-6}$, $R^{2-7}$ and $R^{2-8}$ are independently —CN, halogen, —OH, —$NH_2$, —COOH, —$NO_2$, —S(═O)$_2CH_3$, —C(═O)$NHCH_2CH_3$, oxo (═O), —NHC(═O)$R^{2-3-4}$, —C(═O)$OR^{2-3-5}$, $R^{2-3-1}$, or "$R^{2-3-2}$ substituted by one, two or more $R^{2-3-3}$";

$R^{2-3-1}$ and $R^{2-3-2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{2-3-3}$ is independently —CN, halogen, —OH, —$NH_2$, oxo (═O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{2-3-4}$ is independently hydrogen, $R^{2-3-4-1}$, or "$R^{2-3-4-2}$ substituted by one, two or more $R^{2-3-4-3}$";

$R^{2-3-4-1}$ and $R^{2-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{2-3-4-3}$ is independently —CN, halogen, —OH, —$NH_2$, oxo (═O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{2-3-5}$ is independently hydrogen, $R^{2-3-5-1}$, or "$R^{2-3-5-2}$ substituted by one, two or more $R^{2-3-5-3}$";

$R^{2-3-5-1}$ and $R^{2-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{2-3-3-3}$ is independently —CN, halogen, —OH, —$NH_2$, oxo (═O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

n is 1 or 2;

G is independently —($CR^3R^4$)— or —(C═O)—;

$R^3$ is independently hydrogen, halogen, $R^{3-1}$, "$R^{3-2}$ substituted by one, two or more $R^{3-3}$", —(C═O)$NHR^{3-4}$, —NH(C═O)$R^{3-5}$, —(C═O)$OR^{3-6}$, —S(═O)$_2R^{3-7}$, or —S(═O)$R^{3-8}$;

$R^{3-1}$ and $R^{3-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S"—$C_1$-$C_{40}$ alkyl;

$R^{3-3}$, $R^{3-4}$, $R^{3-5}$, $R^{3-6}$, $R^{3-7}$ and $R^{3-8}$ are independently —CN, halogen, —OH, —$NH_2$, —COOH, —$NO_2$, —S(═O)$_2CH_3$, —C(═O)$NHCH_2CH_3$, oxo (═O), —NHC(═O)$R^{3-3-4}$, —C(═O)$OR^{3-3-5}$, $R^{3-3-1}$, or "$R^{3-3-2}$ substituted by one, two or more $R^{3-3-3}$";

$R^{3-3-1}$ and $R^{3-3-2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{3-3-3}$ is independently —CN, halogen, —OH, —$NH_2$, oxo (═O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{3-3-4}$ is independently hydrogen, $R^{3-3-4-1}$, or "$R^{3-3-4-2}$ substituted by one, two or more $R^{3-3-4-3}$".

$R^{3-3-4-1}$ and $R^{3-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{3-3-4-3}$ is independently —CN, halogen, —OH, —$NH_2$, oxo (═O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{3-3-5}$ is independently hydrogen, $R^{3-3-5-1}$, or "$R^{3-3-5-2}$ substituted by one, two or more $R^{3-3-5-3}$";

$R^{3-3-5-1}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{3-3-5-3}$ is independently —CN, halogen, —OH, —$NH_2$, oxo (=O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^4$ is independently hydrogen, halogen, $R^{4-1}$, "$R^{42}$ substituted by one, two or more $R^{4-3}$", —(C=O)$NHR^{4-4}$, —NH(C=O)$R^{4-5}$, —(C=O)$OR^{4-6}$, —S(=O)$_2R^{4-7}$, or —S(=O)$R^{4-8}$;

$R^{4-1}$ and $R^{4-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, $C_6$-$C_{20}$ aryl-$C_1$-$C_{40}$ alkyl, "5- to 20-membered heteroaryl with 1, 2 or 3 heteroatoms selected from one or more of N, O and S", or "5- to 20-membered heteroaryl with 1, 2 or 3 heteroatoms selected from one or more of N, O and S"—$C_1$-$C_{40}$ alkyl;

$R^{4-3}$, $R^{4-4}$, $R^{4-5}$, $R^{4-6}$, $R^{4-7}$ and $R^{4-8}$ are independently —CN, halogen, —OH, —$NH_2$, —COOH, —$NO_2$, —S(=O)$_2CH_3$, —C(=O)$NHCH_2CH_3$, oxo (=O), —NHC(=O)$R^{4-3-4}$, —C(=O)$OR^{4-3-5}$, $R^{4-3-1}$, or "$R^{4-3-2}$ substituted by one, two or more $R^{4-3-3}$";

$R^{4-3-1}$ and $R^{4-3-2}$ are independently $C_1$-$C_{40}$ alkyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{4-3-3}$ is independently —CN, halogen, —OH, —$NH_2$, oxo (=O), —$S(O)_2CH_3$, C:—Cao alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{4-3-4}$ is independently hydrogen, $R^{4-3-4-1}$, or "$R^{4-3-42}$ substituted by one, two or more $R^{4-3-4-3}$";

$R^{4-3-4-1}$ and $R^{4-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S"

$R^{4-3-4-3}$ is independently —CN, halogen, —OH, —$NH_2$, oxo (=O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^{4-3-5}$ is independently hydrogen, $R^{4-3-5-1}$, or "$R^{4-3-5-2}$ substituted by one, two or more $R^{4-3-5-3}$";

$R^{4-3-5-1}$ and $R^{4-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, "3- to 20-membered heterocycloalkyl with 1, 2 or 3 heteroatoms selected from one or more of N, O and S", $C_6$-$C_{20}$ aryl, or "5- to 20-membered heteroaryl with 1, 2 or 3 heteroatoms selected from one or more of N, O and S";

$R^{4-3-3-3}$ is independently —CN, halogen, —OH, —$NH_2$, oxo (=O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

X is N or CH;

when X is N, Z is $CR^6$; when X is CH, Z is N or $CR^7$;

$R^6$ is hydrogen, halogen, amino, $C_1$-$C_4$ alkyl substituted by one or more $R^{6-2}$, $C_1$-$C_4$ alkoxy or —C(=O)—NH—$R^{6-1}$; $R^{6-1}$ is $C_1$-$C_4$ alkyl; $R^{6-2}$ is independently —CN, halogen, —OH, —$NH_2$, oxo (=O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

$R^7$ is hydrogen, halogen, amino, $C_1$-$C_4$ alkyl substituted by one or more $R^{7-2}$, $C_1$-$C_4$ alkoxy or —C(=O)—NH—$R^{7-1}$; $R^{7-1}$ is $C_1$-$C_4$ alkyl; $R^{7-2}$ is independently —CN, halogen, —OH, —$NH_2$, oxo (=O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

Y is —O—, —S—, —$NR^8$— or —$CH_2$—;

$R^8$ is hydrogen, $C_1$-$C_4$ alkyl substituted by one or more $R^{8-2}$, $C_1$-$C_4$ alkoxy or —C(=O)—NH—$R^{8-1}$; $R^{8-1}$ is $C_1$-$C_4$ alkyl; $R^{8-2}$ is independently —CN, halogen, —OH, —$NH_2$, oxo (=O), —$S(O)_2CH_3$, $C_1$-$C_{40}$ alkyl, "$C_1$-$C_{40}$ alkyl substituted by one or more halogens", $C_1$-$C_{40}$ alkoxy, or "$C_1$-$C_{40}$ alkoxy substituted by one or more halogens";

p is 1, 2 or 3;

$R^5$ is independently cyano, halogen, $C_1$-$C_4$ alkyl, or $C_1$-$C_4$ alkyl substituted by one or more halogens.

In a certain embodiment, some groups in the heterocyclic compound represented by formula I, the tautomer thereof, the pharmaceutically acceptable salt thereof, the solvate thereof or the solvate of the pharmaceutically acceptable salt thereof have the following definitions, and unmentioned groups are defined as described in any one of the above embodiments (this paragraph is hereinafter referred to as "in a certain embodiment"):

m is 1 or 2;

A is independently —($CR^1R^2$)—;

$R^1$ is independently hydrogen or $R^{1-1}$; $R^{1-1}$ is independently $C_1$-$C_{40}$ alkyl;

$R^2$ is hydrogen;

n is 2;

G is independently —($CR^3R^4$)—;

$R^3$ is independently hydrogen, $R^{3-1}$, or "$R^{3-2}$ substituted by one, two or more $R^{3-3}$"; $R^{3-1}$ and $R^{3-2}$ are independently $C_1$-$C_{40}$ alkyl; $R^{3-3}$ is —OH;

$R^4$ is hydrogen;

X is N and Z is $CR^5$;

Re is hydrogen, halogen or —C(=O)—NH—$R^{6-1}$, $R^{6-1}$ is $C_1$-$C_4$ alkyl;

Y is —$NR^8$— or —$CH_2$—; $R^8$ is hydrogen;

p is 1 or 2;

$R^5$ is independently halogen, or $C_1$-$C_4$ alkyl substituted by one or more halogens.

In a certain embodiment:

m is 1 or 2;

A is —($CR^1R^2$)—;

$R^1$ is hydrogen;

$R^2$ is hydrogen;

n is 2;

G is $-(CR^3R^4)-$;
$R^3$ is hydrogen;
$R^4$ is hydrogen;
X is N and Z is $CR^6$;
$R^6$ is hydrogen, halogen or $-C(=O)-NH-R^{6-1}$; $R^{6-1}$ is $C_1$-$C_4$ alkyl;
Y is $-NR^8-$ or $-CH_2-$; $R^8$ is hydrogen;
p is 1 or 2;
$R^5$ is independently halogen, or $C_1$-$C_4$ alkyl substituted by one or more halogens.

In a certain embodiment:
m is 1;
A is $-(CR^1R^2)-$;
$R^1$ is hydrogen;
$R^2$ is hydrogen;
n is 2;
G is $-(CR^3R^4)-$;
$R^3$ is hydrogen;
$R^4$ is hydrogen;
X is N and Z is $CR^6$;
Re is hydrogen;
Y is $-CH_2-$;
p is 1 or 2;
$R^5$ is independently halogen, or $C_1$-$C_4$ alkyl substituted by one or more halogens.

In a certain embodiment, m is 1.

In a certain embodiment, A is independently $-(CR^1R^2)-$.

In a certain embodiment, $R^1$ is independently hydrogen or $R^{1-1}$; $R^{1-1}$ is independently $C_1$-$C_{40}$ alkyl.

In a certain embodiment, $R^1$ is hydrogen.

In a certain embodiment, $R^2$ is hydrogen.

In a certain embodiment, n is 2.

In a certain embodiment, G is independently $-(CR^3R^4)-$.

In a certain embodiment, $R^3$ is independently hydrogen, $R^{3-1}$, or "$R^{3-2}$ substituted by one, two or more $R^{3-3}$"; $R^{3-1}$ and $R^{3-2}$ are independently $C_1$-$C_4$ alkyl; $R^{3-3}$ is $-OH$.

In a certain embodiment, $R^3$ is hydrogen.

In a certain embodiment, $R^4$ is hydrogen.

In a certain embodiment, X is N and Z is $CR^6$; $R^6$ is hydrogen, halogen or $-C(=O)-NH-R^{6-1}$; $R^{6-1}$ is $C_1$-$C_4$ alkyl.

In a certain embodiment, X is N and Z is $CR^6$; $R^6$ is hydrogen.

In a certain embodiment, Y is $-NR^8-$ or $-CH_2-$; $R^8$ is hydrogen.

In a certain embodiment, Y is $-CH_2-$.

In a certain embodiment, p is 1 or 2.

In a certain embodiment, $R^5$ is independently halogen, or $C_1$-$C_4$ alkyl substituted by one or more halogens.

In a certain embodiment, when A is independently $-(CR^1R^2)-$, wherein, the carbon atoms connected to $R^1$ and $R^2$ can be carbon atoms of R-configuration and/or carbon atoms of S-configuration.

In a certain embodiment, when $R^{1-1}$ is independently $C_1$-$C_{40}$ alkyl, the $C_1$-$C_{40}$ alkyl can be $C_1$-$C_4$ alkyl, can also be methyl or ethyl.

In a certain embodiment, when G is independently $-(CR^3R^4)-$, wherein, the carbon atoms connected to $R^3$ and $R^4$ can be carbon atoms of R-configuration and/or carbon atoms of S-configuration.

In a certain embodiment, when $R^{3-1}$ is independently $C_1$-$C_{40}$ alkyl, the $C_1$-$C_{40}$ alkyl can be $C_1$-$C_4$ alkyl, can also be methyl or ethyl.

In a certain embodiment, when $R^{3-2}$ is independently $C_1$-$C_{40}$ alkyl, the $C_1$-$C_{40}$ alkyl can be $C_1$-$C_4$ alkyl, can also be methyl or ethyl.

In a certain embodiment, when $R^3$ is independently "$R^{3-2}$ substituted by one $R^{3-3}$", the "$R^{3-2}$ substituted by one $R^{3-3}$" can be hydroxymethyl.

In a certain embodiment, when $R^6$ is halogen, the halogen can be fluorine, chlorine or bromine, can also be bromine.

In a certain embodiment, when Re-1 is $C_1$-$C_4$ alkyl, the $C_1$-$C_4$ alkyl can be methyl, ethyl, n-propyl, isopropyl, n-butyl, isobutyl, sec-butyl or tert-butyl; can also be methyl.

In a certain embodiment, the $R^5$ can be independently located at the ortho, meta or para position of the Y.

In a certain embodiment, when p is 1, the $R^5$ can be independently located at the ortho position of the Y.

In a certain embodiment, when p is 2, the $R^5$ can be independently located at the ortho or para position of the Y.

In a certain embodiment, when $R^5$ is independently halogen, the halogen can be fluorine, chlorine or bromine, can also be fluorine or chlorine.

In a certain embodiment, when $R^5$ is independently $C_1$-$C_4$ alkyl substituted by one or more halogens, the number of the more halogens can be 2 or 3.

In a certain embodiment, when $R^5$ is independently $C_1$-$C_4$ alkyl substituted by one or more halogens, the halogen can be fluorine, chlorine or bromine, can also be fluorine.

In a certain embodiment, when $R^5$ is independently $C_1$-$C_4$ alkyl substituted by one or more halogens, the $C_1$-$C_4$ alkyl can be methyl, ethyl, n-propyl, isopropyl, n-butyl, isobutyl, sec-butyl or tert-butyl; can also be methyl.

In a certain embodiment, when $R^5$ is independently $C_1$-$C_4$ alkyl substituted by more halogens, the $C_1$-$C_4$ alkyl substituted by more halogens can be difluoromethyl or trifluoromethyl.

In a certain embodiment, the

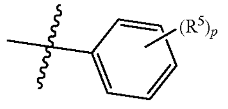

can be 2-trifluoromethylphenyl, 2-trifluoromethyl-4-fluorophenyl, 2-difluoromethyl-4-fluorophenyl, 2,4-difluorophenyl or 2-chloro-4-fluorophenyl.

In a certain embodiment, in the heterocyclic compound represented by formula I, the tautomer thereof, the pharmaceutically acceptable salt thereof, the solvate thereof or the solvate of the pharmaceutically acceptable salt thereof, the heterocyclic compound represented by formula I is any one of the following compounds:

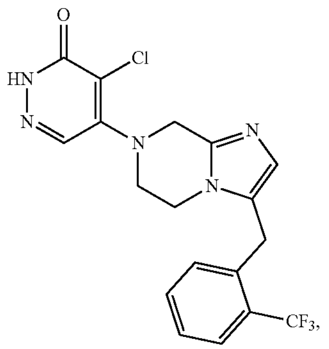

-continued
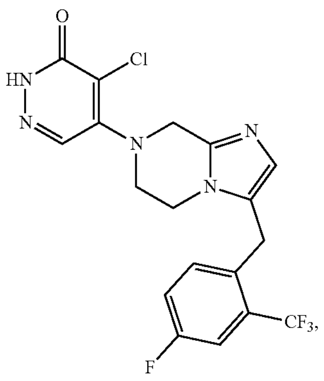
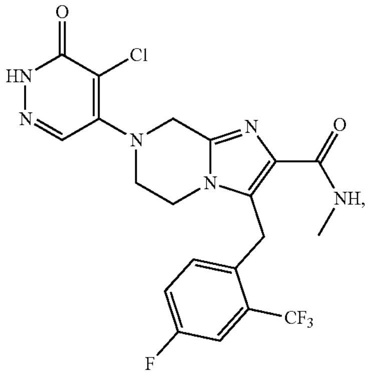
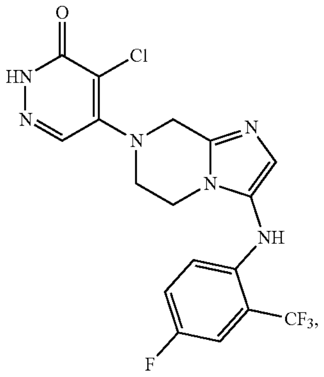
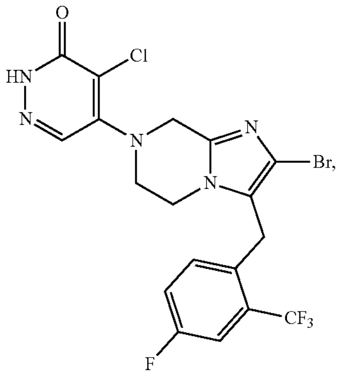
-continued
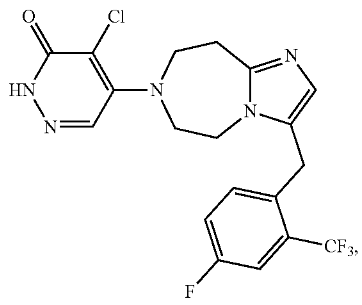
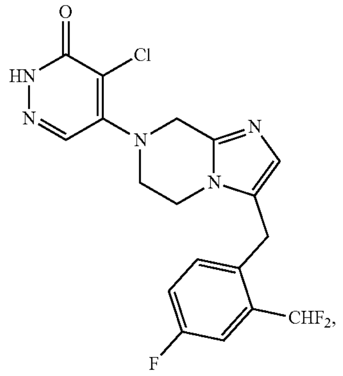
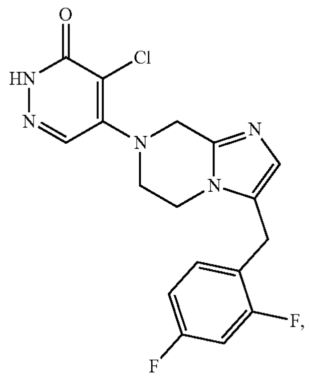
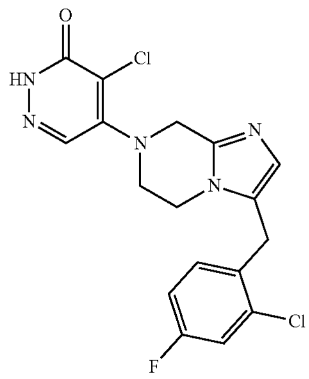

-continued
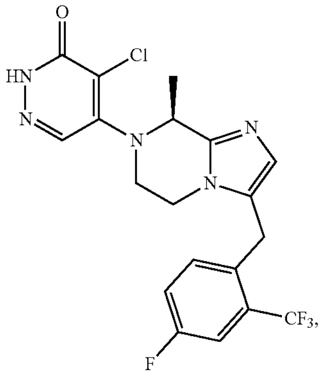
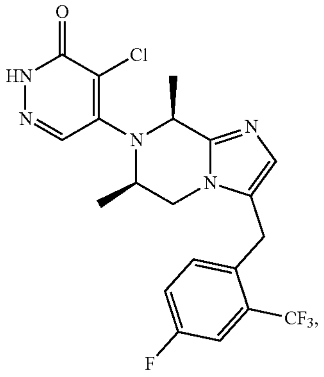
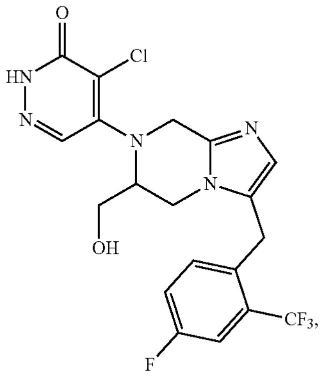
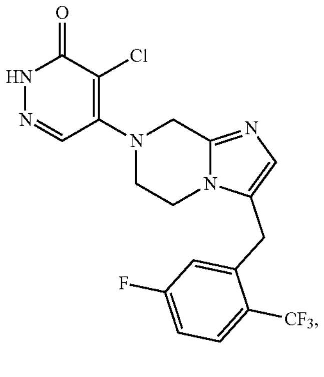
-continued
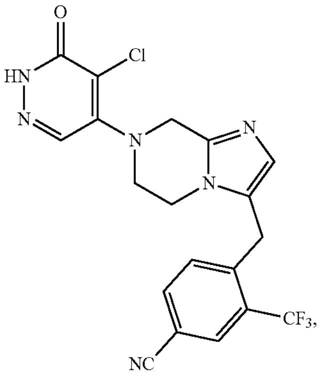
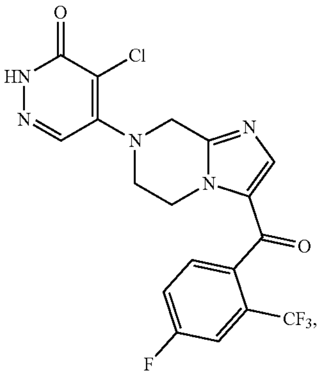
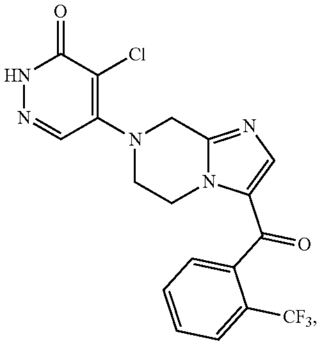
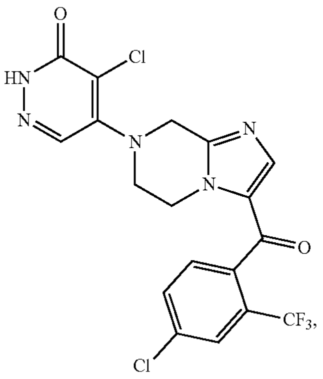

-continued
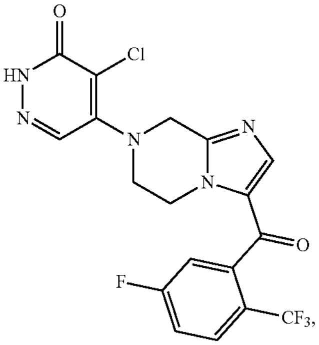
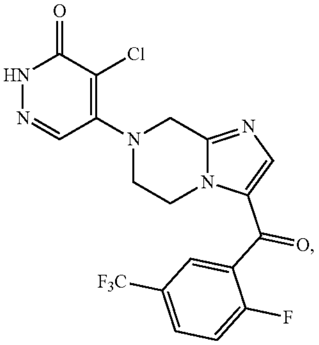
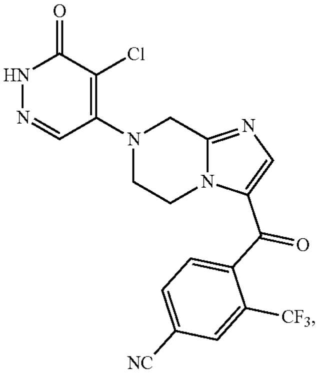
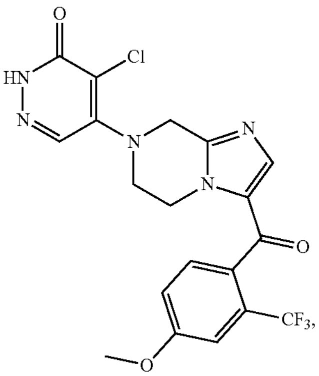
-continued
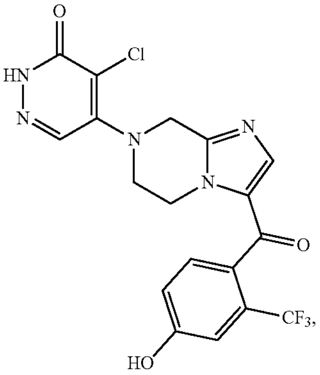
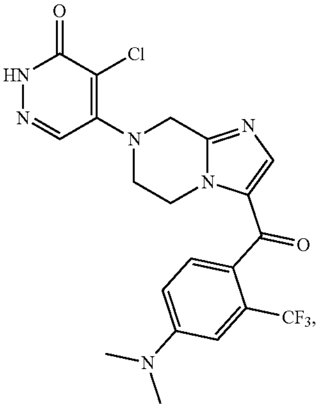
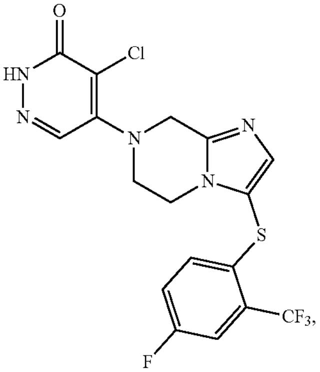
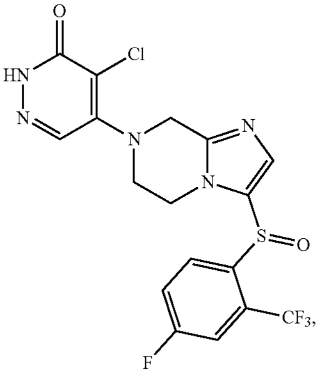

-continued

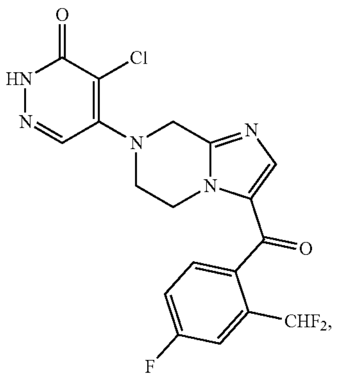

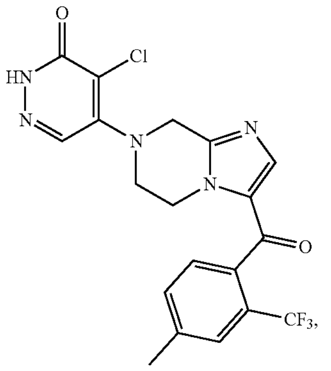

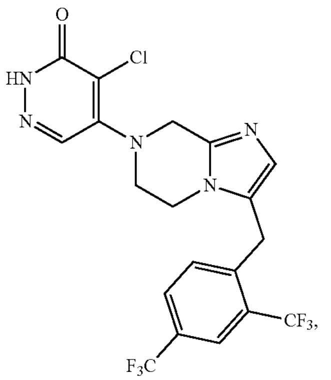

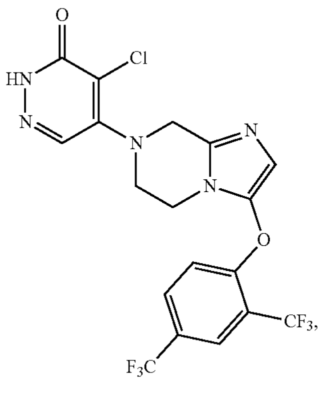

-continued

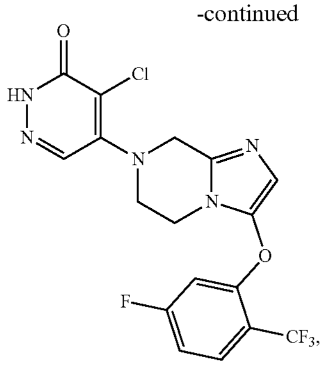

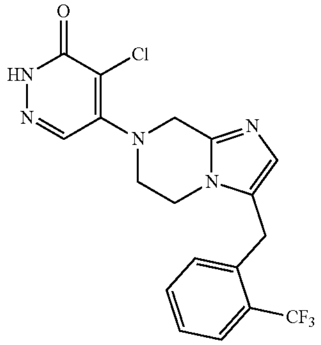

and

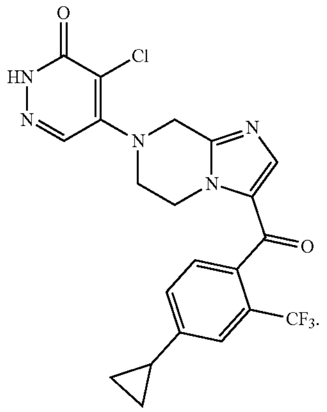 [SMILES: O=C(c1ccc(C2CC2)cc1C(F)(F)F)c1cnc2n1CCN(c1cn[nH]c(=O)c1Cl)C2]

The present disclosure also provides a pharmaceutical composition, comprising substance Y and pharmaceutical excipients; the substance Y is the heterocyclic compound represented by formula I, the tautomer thereof, the pharmaceutically acceptable salt thereof, the solvent thereof or the solvent of the pharmaceutically acceptable salt thereof.

The present disclosure also provides a use of substance Y in the manufacture of a TRPC5 inhibitor, the substance Y is the heterocyclic compound represented by formula I, the tautomer thereof, the pharmaceutically acceptable salt thereof, the solvate thereof or the solvent of the pharmaceutically acceptable salt thereof.

The present disclosure also provides a use of the substance Y in the manufacture of a medicament, the substance Y is the heterocyclic compound represented by formula I, the tautomer thereof, the pharmaceutically acceptable salt thereof, the solvate thereof or the solvent of the pharmaceutically acceptable salt thereof, the medicament is a medicament for the treatment and/or prevention of a TRPC5-mediated disease.

In the use, the TRPC5-mediated disease can be psychiatric condition, neurological condition, neurodegenerative condition or nephropathy.

The psychiatric condition, neurological condition or neurodegenerative condition can be selected from: diseases associated with dysregulated emotional processing (for example, borderline personality disorder or depression, such as major depression, major depressive disorder, psychiatric depression, dysthymia and postpartum depression, and bipolar disorder), disorders associated with anxiety and fear (for example, post-traumatic stress disorder, panic disorder, agoraphobia, social phobia, generalized anxiety disorder, panic disorder, social anxiety disorder, obsessive-compulsive disorder and separation anxiety), memory disorders (for example, Alzheimer's disease, amnesia, aphasia, brain injury, brain tumor, chronic fatigue syndrome, Creutzfeldt-Jakob disease, dissociative amnesia, fugue amnesia, Huntington's disease, learning disorder, sleeping disorder, multiple personality disorder, pain, post-traumatic stress disorder, schizophrenia, sports injury, stroke and Wernicke-Korsakoff Syndrome), disorders associated with impaired impulse control and addiction, Alzheimer's disease, Parkinson's disease, Huntington's disease, amyotrophic lateral sclerosis, epilepsy, and other brain disease caused by trauma or other insults including aging.

The nephropathy can be focal segmental glomerulosclerosis (FSGS), minimal change nephropathy or diabetic nephropathy.

The present disclosure also provides a use of the substance Y in the manufacture of a medicament, the substance Y is the heterocyclic compound represented by formula I, the tautomer thereof, the pharmaceutically acceptable salt thereof, the solvent thereof, or the solvent of the pharmaceutically acceptable salt thereof, the medicament is a medicament for the treatment and/or prevention of psychiatric condition, neurological condition, neurodegenerative condition or nephropathy.

In the use, the TRPC5-mediated disease can be psychiatric condition, neurological condition, neurodegenerative condition or nephropathy.

The psychiatric condition, neurological condition or neurodegenerative condition can be selected from: diseases associated with dysregulated emotional processing (for example, borderline personality disorder or depression, such as major depression, major depressive disorder, psychiatric depression, dysthymia and postpartum depression, and bipolar disorder), disorders associated with anxiety and fear (for example, post-traumatic stress disorder, panic disorder, agoraphobia, social phobia, generalized anxiety disorder, panic disorder, social anxiety disorder, obsessive-compulsive disorder and separation anxiety), memory disorders (for example, Alzheimer's disease, amnesia, aphasia, brain injury, brain tumor, chronic fatigue syndrome, Creutzfeldt-Jakob disease, dissociative amnesia, fugue amnesia, Huntington's disease, learning disorder, sleeping disorder, multiple personality disorder, pain, post-traumatic stress disorder, schizophrenia, sports injury, stroke and Wernicke-Korsakoff Syndrome), disorders associated with impaired impulse control and addiction, Alzheimer's disease, Parkinson's disease, Huntington's disease, amyotrophic lateral sclerosis, epilepsy, and other brain disease caused by trauma or other insults including aging.

In the use, the nephropathy can be focal segmental glomerulosclerosis (FSGS), minimal change nephropathy or diabetic nephropathy.

The present disclosure also provides a method for treating and/or preventing a TRPC5-mediated disease, comprising administering a therapeutic effective amount of substance Y to a subject in need thereof; the substance Y is the heterocyclic compound represented by formula I, the tautomer thereof, the pharmaceutically acceptable salt thereof, the solvent thereof or the solvent of the pharmaceutically acceptable salt thereof.

In the method, the TRPC5-mediated disease can be psychiatric condition, neurological condition, neurodegenerative condition or nephropathy.

The psychiatric condition, neurological condition or neurodegenerative condition can be selected from: diseases associated with dysregulated emotional processing (for example, borderline personality disorder or depression, such as major depression, major depressive disorder, psychiatric depression, dysthymia and postpartum depression, and bipolar disorder), disorders associated with anxiety and fear (for example, post-traumatic stress disorder, panic disorder, agoraphobia, social phobia, generalized anxiety disorder, panic disorder, social anxiety disorder, obsessive-compulsive disorder and separation anxiety), memory disorders (for example, Alzheimer's disease, amnesia, aphasia, brain injury, brain tumor, chronic fatigue syndrome, Creutzfeldt-Jakob disease, dissociative amnesia, fugue amnesia, Huntington's disease, learning disorder, sleeping disorder, multiple personality disorder, pain, post-traumatic stress disorder, schizophrenia, sports injury, stroke and Wernicke-Korsakoff Syndrome), disorders associated with impaired impulse control and addiction, Alzheimer's disease, Parkinson's disease, Huntington's disease, amyotrophic lateral sclerosis, epilepsy, and other brain disease caused by trauma or other insults including aging.

The nephropathy can be focal segmental glomerulosclerosis (FSGS), minimal change nephropathy or diabetic nephropathy.

The present disclosure also provides a method for treating and/or preventing psychiatric condition, neurological condition, neurodegenerative condition or nephropathy, comprising administering a therapeutic effective amount of substance Y to a subject in need thereof; the substance Y is the heterocyclic compound represented by formula I, the tautomer thereof, the pharmaceutically acceptable salt thereof, the solvent thereof or the solvent of the pharmaceutically acceptable salt thereof.

In the method, the psychiatric condition, neurological condition or neurodegenerative condition can be selected from: diseases associated with dysregulated emotional processing (for example, borderline personality disorder or depression, such as major depression, major depressive disorder, psychiatric depression, dysthymia and postpartum depression, and bipolar disorder), disorders associated with anxiety and fear (for example, post-traumatic stress disorder, panic disorder, agoraphobia, social phobia, generalized anxiety disorder, panic disorder, social anxiety disorder, obsessive-compulsive disorder and separation anxiety), memory disorders (for example, Alzheimer's disease, amnesia, aphasia, brain injury, brain tumor, chronic fatigue syndrome, Creutzfeldt-Jakob disease, dissociative amnesia, fugue amnesia, Huntington's disease, learning disorder, sleeping disorder, multiple personality disorder, pain, post-traumatic stress disorder, schizophrenia, sports injury, stroke and Wernicke-Korsakoff Syndrome), disorders associated with impaired impulse control and addiction, Alzheimer's disease, Parkinson's disease, Huntington's disease, amyotrophic lateral sclerosis, epilepsy, and other brain disease caused by trauma or other insults including aging.

In the method, the nephropathy can be focal segmental glomerulosclerosis (FSGS), minimal change nephropathy or diabetic nephropathy.

Unless otherwise stated, the terms used in the description and claims of the present disclosure have the following meanings:

The term "pharmaceutically acceptable salt" refers to the salt prepared by the compound of the present disclosure and a relatively nontoxic and pharmaceutically acceptable acid or base. When the compound of the present disclosure contains a relatively acidic functional group, a base addition salt can be obtained by bringing the prototype form of the compound into contact with a sufficient amount of pharmaceutically acceptable base in a pure solution or a suitable inert solvent. Pharmaceutically acceptable base addition salts include, but are not limited to, lithium salt, sodium salt, potassium salt, calcium salt, aluminum salt, magnesium salt, zinc salt, bismuth salt, ammonium salt, diethanolamine salt. When the compound of the present disclosure contains a relatively basic functional group, an acid addition salt can be obtained by bringing the prototype form of the compound into contact with a sufficient amount of pharmaceutically acceptable acid in a pure solution or a suitable inert solvent. The pharmaceutically acceptable acids include inorganic acids, including but not limited to: hydrochloric acid, hydrobromic acid, hydroiodic acid, nitric acid, carbonic acid, phosphoric acid, phosphorous acid, sulfuric acid, ect. The pharmaceutically acceptable acid includes organic acid, the organic acid includes but is not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, hydrogen tartrate, ascorbic acid, gentisic acid, fumaric acid, gluconic acid, sugar acid, formic acid, ethanesulfonic acid, pamoic acid (i.e., 4,4'-methylene-bis(3-hydroxy-2-naphthoic acid), amino acids (such as glutamic acid, arginine), etc. When the compounds of the present disclosure contain relatively acidic and relatively basic functional groups, they can be converted into base addition salts or acid addition salts. For details, see Berge et al., "Pharmaceutical Salts", Journal of Pharmaceutical Science 66:1-19 (1977), or, Handbook of Pharmaceutical Salts: Properties, Selection, and Use (P. Heinrich Stahl and Camille G. Wermuth, ed., Wiley-VCH, 2002).

The term "solvate" refers to a substance formed by combining a compound of the present disclosure with a stoichiometric or non-stoichiometric solvent. Solvent molecules in solvates can exist in an ordered or unordered arrangement. The solvent includes, but is not limited to, water, methanol, ethanol, etc.

As mentioned above, the terms "pharmaceutically acceptable salt" and "solvate" in the term "solvate of pharmaceutically acceptable salt" refer to a substance formed by combining the compounds of the present disclosure: 1, with relatively nontoxic and pharmaceutically acceptable acids or bases, and, 2, with stoichiometric or non-stoichiometric solvents. The "solvate of pharmaceutically acceptable salt" includes but is not limited to hydrochloric acid monohydrate of the compound of the present disclosure.

When an arbitrary variable (e.g., $R^{1-3}$) appears many times in the definition of a compound, the definition of each occurrence of the variable has nothing to do with the definitions of other occurrences, and their meanings are independent of each other and have no influence on each other. Therefore, if a group is substituted by 1, 2 or 3 $R^{1-3}$, that is, the group may be replaced by up to 3 $R^{1-3}$, and the definition of $R^{1-3}$ of this position and the definition of $R^{1-3}$ of the remaining positions are independent of each other. Additionally, combinations of substituents and/or variables are permissible only if such combinations result in stable compounds.

The term "halogen" refers to fluorine, chlorine, bromine or iodine.

The term "alkyl" refers to a saturated straight or branched monovalent hydrocarbon group having one to forty carbon atoms (e.g., $C_1$-$C_6$ alkyl, $C_1$-$C_4$ alkyl, $C_1$-$C_3$ alkyl, etc.). Examples of alkyl include, but are not limited to: methyl, ethyl, 1-propyl, 2-propyl, 1-butyl, 2-methyl-1-butyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl and 1-octyl.

The term "alkenyl" refers to a straight or branched monovalent hydrocarbon group having two to forty carbon atoms with at least one carbon-carbon $sp^2$ double bond (e.g., $C_2$-$C_6$ alkenyl, $C_2$-$C_4$ alkenyl), and includes groups with "cis" and "trans" orientations or "E" and "Z" orientations. Examples of alkenyl include, but are not limited to, vinyl and allyl.

The term "alkynyl" refers to a straight or branched monovalent hydrocarbon group having two to forty carbon atoms with at least one carbon-carbon sp triple bond (e.g., $C_2$-$C_6$ alkynyl, $C_2$-$C_4$ alkynyl). Examples of alkynyl include, but are not limited to ethynyl and propynyl.

The term "alkoxy" refers to an alkyl connected by an oxygen bridge; the alkyl is as defined above. Examples of alkoxy include, but are not limited to, methoxy and ethoxy.

The term "cycloalkyl" refers to a saturated, cyclic hydrocarbon group having three to twenty carbon atoms, preferably three to twelve carbon atoms, more preferably three to six carbon atoms. Examples of cycloalkyl include, but are not limited to, cyclopropyl, cyclobutyl, cyclopentyl and cyclohexyl.

The term "heterocycloalkyl" refers to a saturated cyclic group having 3 to 20 ring atoms, wherein at least one ring atom is a heteroatom independently selected from oxygen, sulfur, and nitrogen, and the remaining ring atoms are C. The group can be a carbon group or a heteroatom group (that is, it may be a C-linked or N-linked group as long as it is possible). Examples of heterocycloalkyl include, but are not limited to, pyrrolidinyl, tetrahydrofuryl, tetrahydrothienyl, tetrahydropyranyl, tetrahydrothiopyranyl, piperidinyl, morpholinyl, 4-thiomorpholinyl, thioxanyl and piperazinyl.

The term "aryl" refers to a monocyclic, bicyclic or polycyclic carbocycle having six to twenty carbon atoms, at least one of which is an aromatic ring. When one of the rings is a non-aromatic ring, the group can be connected to other groups through an aromatic ring or a non-aromatic ring. Examples of aryl include, but are not limited to, phenyl, naphthyl, tetrahydronaphthyl, 2,3-dihydroindanyl, biphenyl, phenanthrenyl, anthracenyl, and acenaphthylenyl.

The term "heteroaryl" refers to a monocyclic, bicyclic or polycyclic group having 3 to 20 ring atoms, wherein at least one ring atom is a heteroatom independently selected from oxygen, sulfur, and nitrogen, and the remaining ring atoms are C. The group can be a carbon group or a heteroatom group (that is, it may be a C-linked or N-linked group as long as it is possible). When one of the rings is a non-aromatic ring, the group can be connected to other groups through an aromatic ring or a non-aromatic ring. Examples of heteroaryl includes, but is not limited to: acridinyl, carbazolyl, cinnolinyl, quinoxalinyl, pyrazolyl, indolyl, benzotriazolyl, furyl, thienyl, benzothienyl, benzofuryl, quinolinyl, isoquinolyl, oxazolyl, isoxazolyl, indolyl, pyrazinyl, pyridazinyl, pyridyl, pyrimidinyl, pyrrolyl and tetrahydroquinolinyl.

The term "pharmaceutical excipients" refers to the excipients and additives used in the manufacture of drugs and the formulation of prescriptions, which are all substances contained in pharmaceutical preparations except active ingredients. Available in the Pharmacopoeia of the People's Republic of China (2020 Edition) Part IV, or, Handbook of Pharmaceutical Excipients (Raymond C Rowe, 2009 Sixth Edition).

The term "treatment" refers to therapeutic therapy. In relation to a specific disorder, treatment refers to: (1) ameliorating one or more biological manifestations of the disease or disorder, (2) interfering with (a) one or more points in the biological cascade leading to or causing the disorder or (b) one or more biological manifestations of the disorder, (3) ameliorating one or more symptoms, effects or side effects associated with the disorder, or one or more symptoms, effects or side effects associated with the disorder or its treatment, or (4) slowing the progression of the disorder or one or more biological manifestations of the disorder.

The term "prevention" refers to the reduction of the risk of acquiring or developing diseases or disorders.

The term "patient" refers to any animal that will or has received the compound or composition according to the embodiment of the present disclosure, preferably mammals. The term "mammal" includes any mammal. Examples of mammals include, but are not limited to, cows, horses, sheep, pigs, cats, dogs, mice, rats, rabbits, guinea pigs, monkeys, humans, etc., preferably humans.

The term "therapeutically effective amount" refers to the amount of a compound that is sufficient to effectively treat the diseases or disorders described herein when administered to a patient. The "therapeutically effective amount" will vary according to the compound, the disease and its severity, and the age of the patient to be treated, but it can be adjusted by those skilled in the art as needed.

On the basis of not violating the common sense in the field, the preferred conditions above can be arbitrarily combined to obtain the preferred examples of the present disclosure.

The reagents and raw materials used in the present disclosure are commercially available.

The positive progressive effect of the present disclosure is: the compound has better inhibitory activity on TRPC5, has good metabolic stability in liver microsomes, and has good clinical pharmacokinetic properties.

BRIEF DESCRIPTION OF THE DRAWING

The FIGURE shows the distribution of plasma concentration in the tissues of CD-1 mice with single intragastric administration.

DETAILED DESCRIPTION OF THE PREFERRED EMBODIMENT

The present disclosure is further described below by the way of examples, but the present disclosure is not thereby limited to the scope of the described examples. The experimental methods not specified in the specific conditions in the following examples are selected according to the conventional methods and conditions, or according to the commodity instructions.

Terms and Representative Reagents

The terms used in the following specific experimental descriptions refer to (unless otherwise stated) the following reagents:

NBS: N-bromosuccinimide; DIEA: N,N-diisopropylethylamine; EA: ethyl acetate; DCM: dichloromethane; DMF: N,N-dimethylformamide; THF: tetrahydrofuran; i.v.: intravenous injection; p.o.: oral administration.

Example 1 Preparation of Compound 4-chloro-5-(3-(2-(trifluoromethyl)benzyl)-5,6-dihydroimidazo[1,2-a]pyrazin-7(8H)-yl)pyridazin-3(2H)-one (L001)

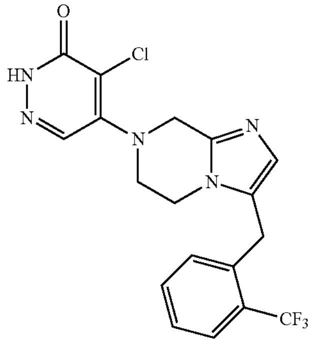

L001

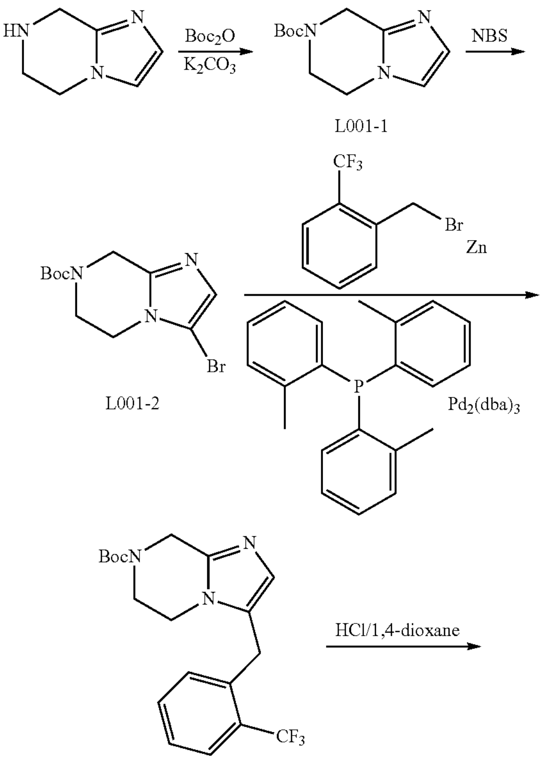

L001-1

L001-2

L001-3

-continued

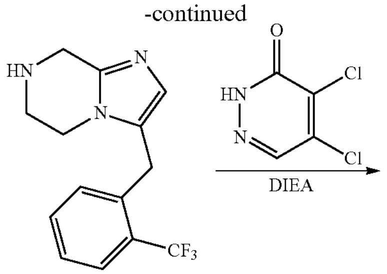

L001-4

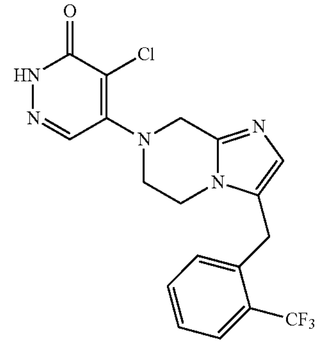

L001

1.1 Preparation of Compound tert-butyl 5,6-dihydroimidazo[1,2-a]pyrazine-7(8H)-carboxylate (L001-1)

5,6,7,8-Tetrahydroimidazo[1,2-a]pyrazine (700 mg, 5.68 mmol) and $K_2CO_3$ (1.57 g, 11.37 mmol) were added to a single-necked flask, and $H_2O$ (8 mL) and THF (8 mL) were added thereto, and then (Boc) 20 was added dropwise after the dissolution was completed, and the reaction solution was reacted overnight at room temperature after the addition was completed. TLC (DCM/MeOH=10/1) showed that the reaction was completed. The reaction solution was added with NaCl to saturate, and extracted with EA, and then the organic phase was dried over anhydrous sodium sulfate and concentrated to obtain compound L001-1 (1.2 g) as a brown solid.

1.2 Preparation of Compound tert-butyl 3-bromo-5,6-dihydroimidazo[1,2-a]pyrazine-7(8H)-carboxylate (L001-2)

tert-Butyl 5,6-dihydroimidazo[1,2-a]pyrazine-7(8H)-carboxylate (1.2 g, 5.37 mmol) was added to a single-necked flask, and DMF (10 mL) was added thereto, and then NBS (1.15 g, 6.45 mmol) was slowly added after the dissolution was completed and the reaction solution was reacted overnight at room temperature. TLC (DCM/MeOH=10/1) showed that the reaction was completed, and the reaction solution was subjected to preparative separation (MeCN, $H_2O$, 0.05% TFA) to obtain compound L001-2 (700 mg) as a light-yellow solid.

1.3 Preparation of Compound tert-butyl 3-(2-(trifluoromethyl)benzyl)-5,6-dihydroimidazo[1,2-a]pyrazine-7(8H)-carboxylate (L001-3)

2-(Trifluoromethyl)benzyl bromide (791.1 mg, 3.31 mmol) and Zn (8.27 mmol) were added to a single-necked flask, and anhydrous THF (5 mL) was added thereto, and the mixture was reacted overnight at room temperature under the protection of nitrogen, and then Pd2 (dba); (91.6 mg), tris(o-methylphenyl)phosphine (50.3 mg) and tert-butyl 3-bromo-5,6-dihydroimidazo[1,2-a]pyrazine-7(8H)-carboxylate (500 mg, 1.65 mmol) were added to the single-necked flask. The mixture was reacted at 70° C. for 2 hours under the protection of nitrogen, and TLC (pure EA) showed that the reaction was completed, and then the mixture was extracted with EA. The organic phase was washed with saturated brine and then concentrated, and the crude product was purified by silica gel column chromatography to obtain compound L001-3 (80 mg) as a colorless liquid.

1.4 Preparation of Compound 3-(2-(trifluoromethyl)benzyl)-5,6,7,8-tetrahydroimidazo[1,2-a]pyrazine (L001-4)

tert-Butyl 3-(2-(trifluoromethyl)benzyl)-5,6-dihydroimidazo[1,2-a]pyrazine-7(8H)-carboxylate (60 mg, 157.3 μmol) was dissolved in DCM (2 mL), and after the dissolution was completed, HCl/1,4-dioxane (2 mL, 4 N) was added with stirring, and the reaction solution was reacted at room temperature for 3 hours after the addition was completed. TLC (pure EA with 1 drop of ammonia water) showed that the reaction was completed. The reaction solution was concentrated to obtain compound L001-4 (45 mg) as a white solid.

1.5 Preparation of Compound 4-chloro-5-(3-(2-(trifluoromethyl)benzyl)-5,6-dihydroimidazo[1,2-a]pyrazin-7(8H)-yl)pyridazin-3(2H)-one (L001)

3-(2-(Trifluoromethyl)benzyl)-5,6,7,8-tetrahydroimidazo[1,2-a]pyrazine (43 mg, 152.9 μmol) was added to a single necked flask, and 4,5-dichloropyridazin-3(2H)-one (211.1 mg, 1.28 mmol), DIEA (59.2 mg, 458.6 μmol) and DMF (2 mL) were added thereto, and the mixture was reacted overnight at 100° C. under the protection of nitrogen. TLC (DCM/MeOH=10/1) showed that the reaction was completed. The crude product was subjected to preparative separation by preparative HPLC ($H_2O$, MeCN, 0.05% TFA), and lyophilized to obtain compound L001 as a white solid (6.1 mg, purity of 97.71%).

LC-MS $[M+H]^+$=410.05.

$^1H$ NMR (400 MHz, DMSO-$d_6$) δ 13.08 (s, $^1H$), 7.97 (s, $^1H$), 7.80 (d, J=7.9 Hz, $^1H$), 7.65 (t, J=7.7 Hz, $^1H$), 7.53 (t, J=7.6 Hz, $^1H$), 7.33 (d, J=7.6 Hz, $^1H$), 7.18 (s, $^1H$), 4.96 (s, 2H), 4.24 (s, 2H), 4.12 (d, J=4.9 Hz, 2H), 3.93 (d, J=5.0 Hz, 2H).

Example 2 Preparation of 4-chloro-5-(3-(4-fluoro-2-(trifluoromethyl)benzyl)-5,6-dihydroimidazo[1,2-a]pyrazin-7(8H)-yl)pyridazin-3(2H)-one (L002)
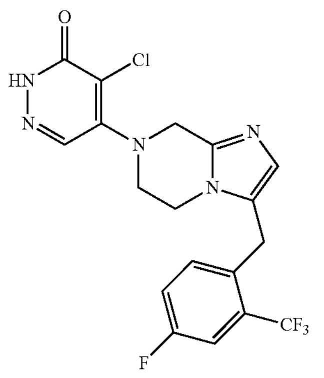
L002
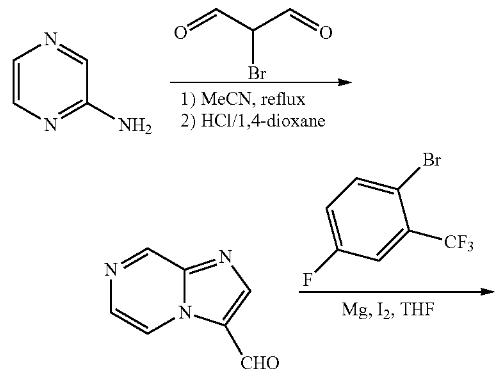
L002-1
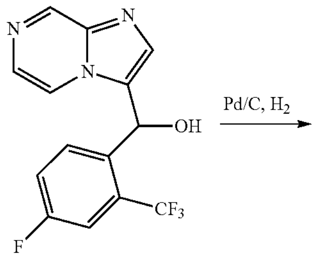
L002-2
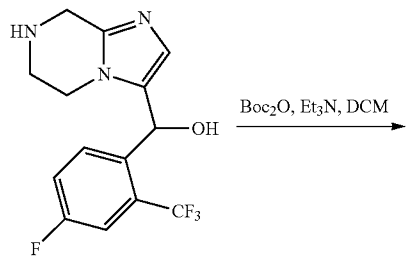
L002-3
-continued
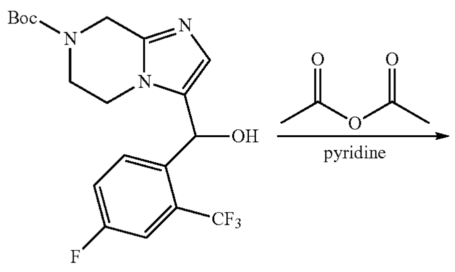
L002-4
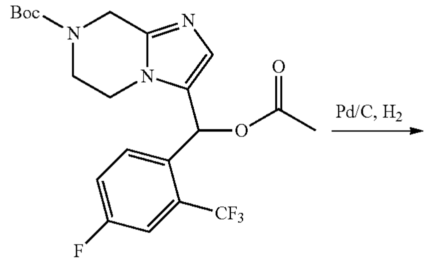
L002-5
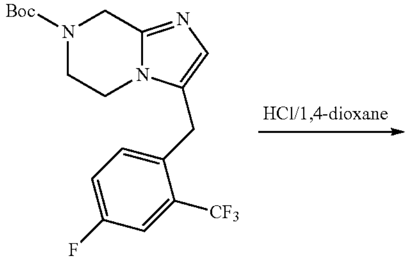
L002-6
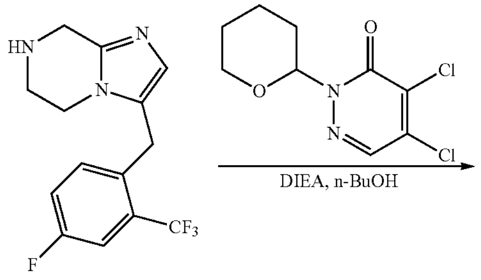
L002-7
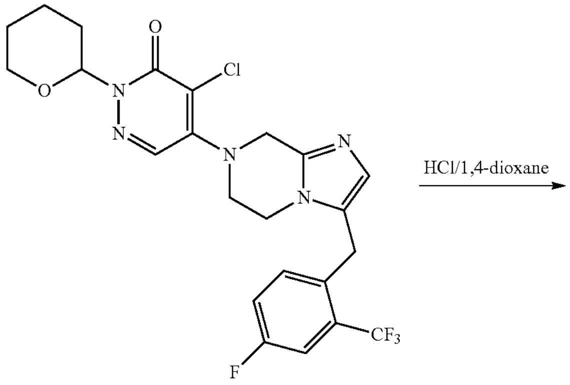
L002-8

-continued

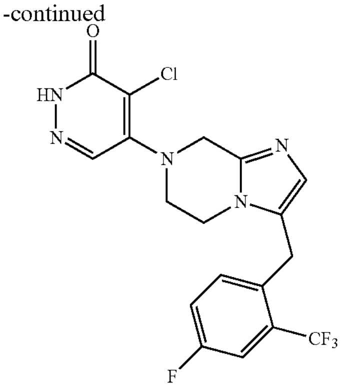

L002

2.1 Preparation of Compound imidazo[1,2-a]pyrazine-3-carbaldehyde (L002-1)

Aminopyrazine (10.0 g, 0.11 mol) was dissolved in anhydrous ethanol (100 mL), and 2-bromomalondialdehyde (15.8 g, 0.11 mmol) was added thereto, and the mixture was stirred at 90° C. for 2 hours. After the reaction was completed, the mixture was cooled to room temperature, and evaporated to dryness by rotary evaporation to remove the solvent to obtain a black viscous substance, and then a solution of hydrogen chloride in 1,4-dioxane (4 mmol/L, 30 mL) was added, and the resulting mixture was stirred at 25° C. for 12 hours. After the reaction was completed, 50 mL of water was added. The pH of the mixture was adjusted to about 8 with sodium carbonate solution, and then extracted with ethyl acetate (50 mL*4). The organic phase was washed with saturated brine (30 mL*2), dried over anhydrous sodium sulfate, and then evaporated to dryness by rotary evaporation to remove the solvent and the residue was recrystallized for three times to obtain 3.5 g of yellow solid with a yield of 22%. LC-MS [M+H]+=148.0.

2.2 Preparation of Compound (4-fluoro-2-(trifluoromethyl)phenyl)(imidazo[1,2-a]pyrazin-3-yl) methanol (L002-2)

2-Bromo-5-fluorobenzotrifluoride (7.47 g, 30.6 mmol) was dissolved in tetrahydrofuran (50 mL), and 2 mL of the solution was added dropwise to a solution of magnesium chips (1.47 g, 61.2 mmol) and iodine (50 mg, 2 mmol) in tetrahydrofuran (20 mL) under the protection of nitrogen, and the solution was heated with a hair dryer until the solution was clear and transparent, then the remaining solution of 2-bromo-5-fluorobenzotrifluoride in tetrahydrofuran was added dropwise to the reaction system. The mixture was stirred at 70° C. for 1 hour and then cooled to room temperature. The resulting mixture was then added dropwise to a solution of imidazo[1,2-a]pyrazine-3-carbaldehyde (3.00 g, 20.4 mmol) in tetrahydrofuran at −70° C. under the protection of nitrogen. The mixed system was stirred at −70° C. for 2 hours. After the reaction was completed, ammonium chloride solution (50 mL) was added, and the mixture was extracted with ethyl acetate (50 mL*3), and then the organic phase was washed with saturated brine (30 mL*2), dried over anhydrous sodium sulfate, filtered, and the filtrate was concentrated, and the crude product was separated by silica gel column chromatography (DCM/MeOH=100/1) to obtain 3.20 g of yellow solid with a yield of 41%. LC-MS $[M+H]^+$=312.07.

2.3 Preparation of Compound (4-fluoro-2-(trifluoromethyl)phenyl) (5,6,7,8-tetrahydroimidazo[1,2-a] pyrazin-3-yl) methanol (L002-3)

(4-Fluoro-2-(trifluoromethyl)phenyl) (imidazo[1,2-a] pyrazin-3-yl) methanol (1.10 g, 3.50 mmol) was dissolved in tetrahydrofuran (25 mL), Wet Pd/C (10%, 400 mg) was added and the mixture was stirred for 12 hours at room temperature under hydrogen atmosphere. After the reaction was completed, the mixture was filtered, and the filtrate was evaporated to dryness by rotary evaporation to remove the solvent to obtain 1.00 g of white solid with a yield of 90%, LC-MS $[M+H]^+$=316.2.

2.4 Preparation of Compound tert-butyl 3-((4-fluoro-2-(trifluoromethyl)phenyl) (hydroxy)methyl)-5,6-dihydroimidazo[1,2-a]pyrazine-7(8H)-carboxylate (L002-4)

(4-Fluoro-2-(trifluoromethyl)phenyl) (5,6,7,8-tetrahydroimidazo[1,2-a]pyrazin-3-yl) methanol (1.00 g, 3.16 mmol) was dissolved in tetrahydrofuran (10 mL)/water (5 mL), and sodium carbonate (1.00 g, 9.48 mmol) and di-tert-butyl dicarbonate (0.83 g, 3.79 mmol) were added thereto, and the mixture was stirred at 25° C. for 2 hours. After the reaction was completed, water (50 mL) was added, and the mixture was extracted with ethyl acetate (20 mL*3), and then the organic phase was washed with saturated brine (20 mL*2), dried over anhydrous sodium sulfate and evaporated to dryness by rotary evaporation to remove the solvent to obtain 1.00 g of yellow solid with a yield of 71%. LC-MS $[M+H]^+$=416.4.

2.5 Preparation of Compound tert-butyl 3-(acetoxy (4-fluoro-2-(trifluoromethyl)phenyl)methyl)-5,6-dihydroimidazo[1,2-a]pyrazine-7(8H)-carboxylate (L002-5)

tert-Butyl 3-((4-fluoro-2-(trifluoromethyl)phenyl) (hydroxy)methyl)-5,6-dihydroimidazo[1,2-a]pyrazine-7(8H)-carboxylate (1.00 g, 2.40 mmol) was dissolved in pyridine (10 mL), and acetic anhydride (300 mg, 2.89 mmol) was added thereto, and the mixture was stirred at 25° C. for 2 hours. After the reaction was completed, the mixture was evaporated to dryness by rotary evaporation to remove the solvent to obtain 1.10 g of light-yellow oil (90% product), LC-MS $[M+H]^+$=457.9.

2.6 Preparation of Compound tert-butyl 3-(4-fluoro-2-(trifluoromethyl)benzyl)-5,6-dihydroimidazo[1,2-a]pyrazine-7(8H)-carboxylate (L002-6)

tert-Butyl 3-(acetoxy (4-fluoro-2-(trifluoromethyl)phenyl)methyl)-5,6-dihydroimidazo[1,2-a]pyrazine-7(8H)-carboxylate (1.10 g, 2.40 mmol) was dissolved in tetrahydrofuran (10 mL), and wet palladium/carbon (10%, 100 mg) was added thereto. The reaction system was introduced with hydrogen and stirred at 25° C. for 2 hours. After the reaction was completed, the mixture was filtered to remove palladium/carbon, and evaporated to dryness by rotary evaporation to remove the solvent to obtain 800 mg of white solid with a yield of 85%.

LC-MS $[M+H]^+$=400.1.

2.7 Preparation of Compound 3-(4-fluoro-2-(trifluoromethyl)benzyl)-5,6,7,8-tetrahydroimidazo[1,2-a]pyrazine hydrochloride (L002-7)

tert-Butyl 3-(4-fluoro-2-(trifluoromethyl)benzyl)-5,6-dihydroimidazo[1,2-a]pyrazine-7(8H)-carboxylate (500 mg, 1.25 mmol) was dissolved in a solution of hydrogen chloride in 1,4-dioxane (4 mmol/L, 5 mL), and the mixture was stirred at 25° C. for 2 hours. After the reaction was completed, the mixture was evaporated to dryness by rotary evaporation to remove the solvent to obtain 450 mg of light-yellow substance as a crude product. LC-MS $[M+H]^+$ =300.1.

2.8 Preparation of Compound 4-chloro-5-(3-(4-fluoro-2-(trifluoromethyl)benzyl)-5,6-dihydroimidazo[1,2-a]pyrazin-7(8H)-yl)-2-(tetrahydro-2H-pyran-2-yl)pyridazin-3(2H)-one (L002-8)

3-(4-Fluoro-2-(trifluoromethyl)benzyl)-5,6,7,8-tetrahydroimidazo[1,2-a]pyrazine hydrochloride (336 mg, 1.0 mmol) was dissolved in n-butanol (1.5 mL), and then 4,5-dichloro-2-(tetrahydro-2H-pyran-2-yl)pyridazin-3(2H)-one (374 mg, 1.5 mmol) and N,N-diisopropylethanamine (388 mg, 3.0 mmol) were added, and the mixture was stirred at 120° C. for 3 hours under the protection of nitrogen. After the reaction was completed, the mixture was evaporated to dryness by rotary evaporation to remove the n-butanol solvent, and the crude product was separated by silica gel column chromatography (DCM/MeOH=30:1) to obtain 200 mg of yellow solid. The yield was 71%, LC-MS $[M+H]^+$ =512.1.

2.9 Preparation of Compound 4-chloro-5-(3-(4-fluoro-2-(trifluoromethyl)benzyl)-5,6-dihydroimidazo[1,2-a]pyrazin-7(8H)-yl)pyridazin-3(2H)-one (L002)

4-Chloro-5-(3-(4-fluoro-2-(trifluoromethyl)benzyl)-5,6-dihydroimidazo[1,2-a]pyrazin-7(8H)-yl)-2-(tetrahydro-2H-pyran-2-yl)pyridazin-3(2H)-one (200 mg, 0.39 mmol) was dissolved in a solution of hydrogen chloride in 1,4-dioxane (2 mL, 4 mmol/L), and the mixture was stirred at 25° C. for 1 hour. After the reaction was completed, the mixture was evaporated to dryness by rotary evaporation to remove the solvent, and the residue was dissolved in dichloromethane (40 mL). The resulting solution was washed with saturated sodium bicarbonate solution (20 mL), dried over anhydrous sodium sulfate, filtered, and the filtrate was concentrated, and the crude product was purified by preparative chromatography to obtain 94.0 mg of white solid with a yield of 57%. LC-MS $[M+H]^+$=427.9.

$^1$H NMR (400 MHz, DMSO-$d_6$) δ 13.13 (s, $^1$H), 7.99 (s, $^1$H), 7.73 (dd, J=9.3, 2.7 Hz, $^1$H), 7.57 (td, J=8.5, 2.7 Hz, $^1$H), 7.44 (dd, J=8.6, 5.5 Hz, $^1$H), 7.22 (s, $^1$H), 5.00 (s, 2H), 4.23 (s, 2H), 4.17 (d, J=5.1 Hz, 2H), 3.96 (d, J=5.0 Hz, 2H).

Example 3 Preparation of Compound 7-(5-chloro-6-oxo-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (L003)

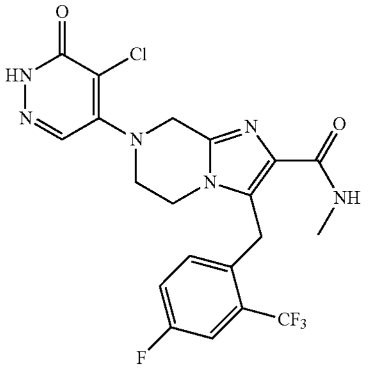

L003

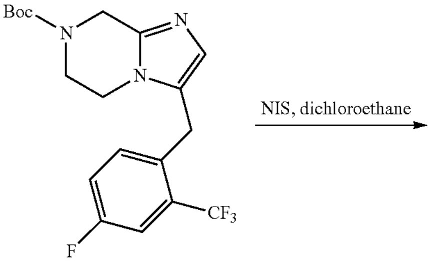

L002-6

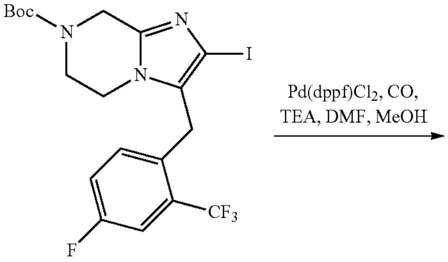

L003-1

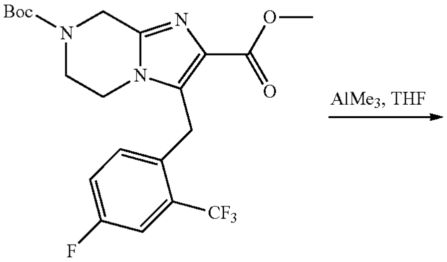

L003-2

-continued

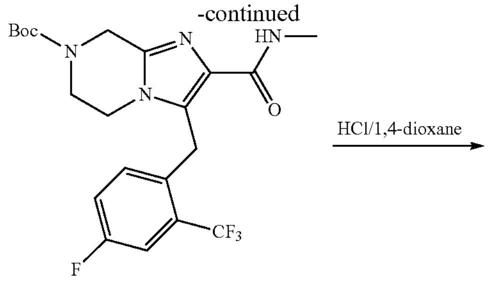

L003-3

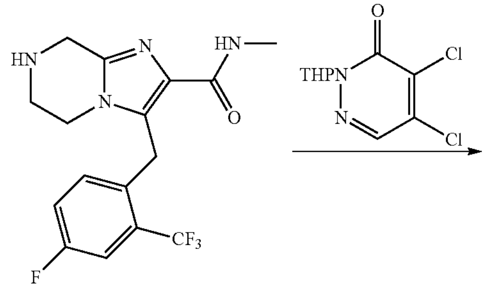

L003-4

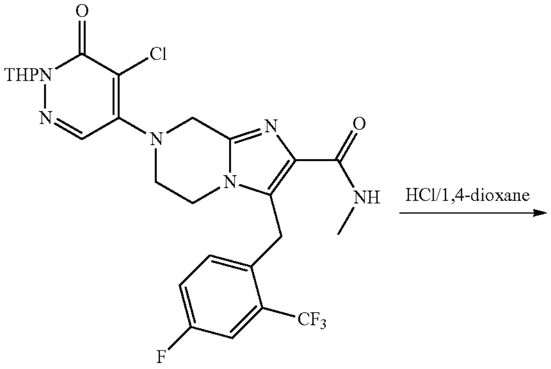

L003-5

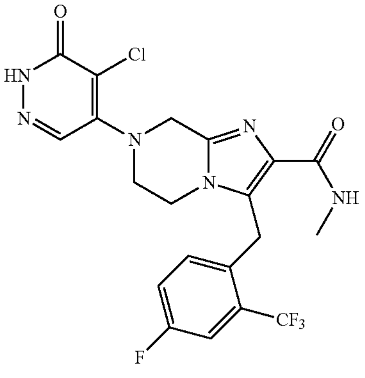

L003

3.1 Preparation of Compound tert-butyl 3-(4-fluoro-2-(trifluoromethyl)benzyl)-2-iodo-5,6-dihydroimidazo[1,2-@] pyrazine-7(8H)-carboxylate (L003-1)

tert-Butyl 3-(4-fluoro-2-(trifluoromethyl)benzyl)-5,6-dihydroimidazo[1,2-a]pyrazine-7(8H)-carboxylate (L002-6, 0.50 g, 1.25 mmol) was dissolved in dichloroethane (6 mL), and N-iodosuccinimide (0.42 g, 1.87 mmol) was added thereto. The reaction solution was stirred at 90° C. for 1 hour under the protection of nitrogen. After the reaction was completed, the mixture was cooled to room temperature, and sodium thiosulfate aqueous solution (10 mL) was added and stirred for five minutes, and then extracted with dichloromethane (10 mL*3). The organic phase was dried over anhydrous sodium sulfate, filtered, and the filtrate was concentrated to give the crude product, which was separated by silica gel column chromatography (dichloromethane/methanol=100:1) to obtain 200 mg of yellow oil with a yield of 27%. LC-MS $[M+H]^{+}$=525.8.

3.2 Preparation of Compound methyl 7-(tert-butoxycarbonyl)-3-(4-fluoro-2-(trifluoromethyl)benzyl)-5,6-dihydroimidazo[1,2-a]pyrazine-2,7(8H)-2-carboxylate (L003-2)

tert-Butyl 3-(4-fluoro-2-(trifluoromethyl)benzyl)-2-iodo-5,6-dihydroimidazo[1,2-a]pyrazine-7(8H)-carboxylate (170 mg, 0.32 mmol), 1,1'-bis(diphenylphosphino) ferrocenepalladium dichloride (24 mg, 0.032 mmol) and triethylamine (162 mg, 1.6 mmol) were dissolved in methanol/N,N-dimethylformamide (3 mL/3 mL), and the reaction system was replaced with nitrogen, and then carbon monoxide was introduced and the mixture was stirred at 70° C. for 16 hours. The reaction solution was filtered, and the filtrate was evaporated to dryness by rotary evaporation. The crude product was purified by silica gel column chromatography (dichloromethane/methanol=40/1) to obtain 126 mg of yellow solid product with a yield of 85%. LC-MS $[M+H]^{+}$=458.

3.3 Preparation of Compound tert-butyl 3-(4-fluoro-2-(trifluoromethyl)benzyl)-2-(methylcarbamoyl)-5,6-dihydroimidazo[1,2-a]pyrazine-7(8H)-carboxylate (L003-3)

At 0° C., methylamine (2 M of THF solution, 0.75 mL, 1.5 mmol) was added to trimethylaluminum (2 M of hexane solution, 0.75 mL, 1.5 mmol), and the mixture was reacted for 0.25 hours, and then methyl 7-(tert-butoxycarbonyl)-3-(4-fluoro-2-(trifluoromethyl)benzyl)-5,6-dihydroimidazo[1,2-a]pyrazine-2,7(8H)-2-carboxylate (126 mg, 0.28 mmol) was added to the above reaction solution, and after the addition was completed, the mixture was raised to 25° C. and stirred for 10 hours. The pH of the mixture was adjusted to neutral with hydrochloric acid (1 N), and the mixture was evaporated to dryness by rotary evaporation, and then the crude product was purified by silica gel column chromatography (dichloromethane/methanol=30/1) to obtain 80 mg of yellow solid product with a yield of 63%.

LC-MS $[M+H]^{+}$=457.

3.4 Preparation of Compound 3-(4-fluoro-2-(trifluoromethyl)benzyl)-N-methyl-5,6,7,8-tetrahydroimidazo[1,2-a]pyrazine-2-carboxamide hydrochloride (L003-4)

tert-Butyl 3-(4-fluoro-2-(trifluoromethyl)benzyl)-2-(methylcarbamoyl)-5,6-dihydroimidazo[1,2-a]pyrazine-7(8H)-carboxylate (80 mg, 0.175 mmol) was dissolved in dichloromethane (3 mL), and a solution of hydrogen chloride in 1,4-dioxane (3 mL, 4N) was added thereto, and the mixture was stirred at room temperature for 1 hour. The reaction solution was evaporated to dryness by rotary evaporation to obtain 70 mg of yellow solid. LC-MS $[M+H]^{+}$=357.

3.5 Preparation of Compound 7-(5-chloro-6-oxo-1-(tetrahydro-2H-pyran-2-yl)-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (L003-5)

3-(4-Fluoro-2-(trifluoromethyl)benzyl)-N-methyl-5,6,7,8-tetrahydroimidazo[1,2-a]pyrazine-2-carboxamide hydrochloride (70 mg, 0.175 mmol), 4,5-dichloro-2-(tetrahydro-2H-pyran-2-yl)pyridazin-3(2H)-one (50 mg, 0.192 mmol) and N,N-diisopropylethanamine (68 mg, 0.525 mmol) were dissolved in n-butanol (1 mL), and the reaction solution was stirred at 120° C. for 4 hours. After the reaction was completed, the mixture was evaporated to dryness by rotary evaporation, and then the crude product was purified by thin-layer chromatography silica gel plate (the mobile phase was ethyl acetate) to obtain 60 mg of white solid with a yield of 59%. LC-MS $[M+H]^+$=569.

3.6 Preparation of Compound 7-(5-chloro-6-oxo-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (L003)

7-(5-Chloro-6-oxo-1-(tetrahydro-2H-pyran-2-yl)-1,6-dihydropyridazin-4-yl)-3-(4-fluoro-2-(trifluoromethyl)benzyl)-N-methyl-5,6,7,8-tetrahydroimidazo[1,2-a]pyrazine-2-carboxamide (60 mg, 0.11 mmol) was dissolved in dichloromethane (2 mL), and a solution of hydrogen chloride in 1,4-dioxane (2 mL, 4N) was added, and the mixture was stirred at room temperature for 1 hour. The reaction solution was evaporated to dryness by rotary evaporation, the crude product was dissolved in methanol/dichloromethane solution (10 mL, 1/15), and solid sodium bicarbonate was added thereto. The mixture was stirred for 5 minutes, filtered, and the filtrate was evaporated to dryness by rotary evaporation, and then the crude product was purified by thin-layer chromatography silica gel plate (methanol/dichloromethane=1/20) to obtain 30 mg of white solid with a yield of 59%.

LC-MS $[M+H]^+$=485.

$^1H$ NMR (400 MHz, $CD_3OD$) δ 7.94 (s, $^1H$), 7.51 (dd, J=9.1, 2.8 Hz, $^1H$), 7.25 (t, J=8.5 Hz, $^1H$), 6.96 (dd, J=8.6, 5.2 Hz, $^1H$), 4.75 (s, 2H), 4.67 (s, 2H), 3.87 (d, J=5.0 Hz, 2H), 3.83 (d, J=5.0 Hz, 2H), 2.87 (s, 3H).

Example 4 Preparation of Compound 4-chloro-5-(3-((4-fluoro-2-(trifluoromethyl)phenyl)amino)-5,6-dihydroimidazo[1,2-a]pyrazin-7(8H)-yl)pyridazin-3(2H)-one (L004)

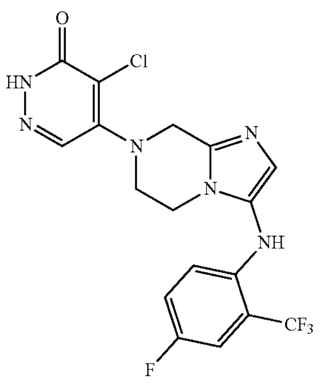

L004

-continued

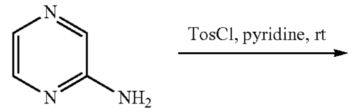

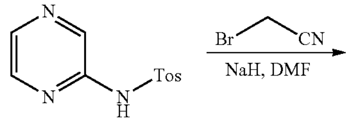

L004-1

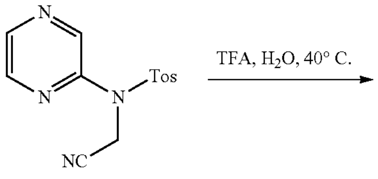

L004-2

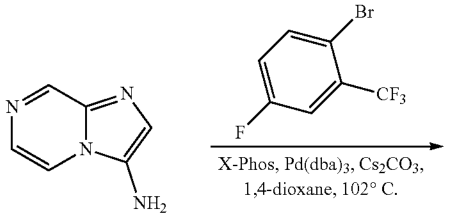

L004-3

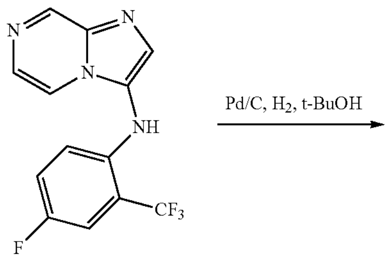

L004-4

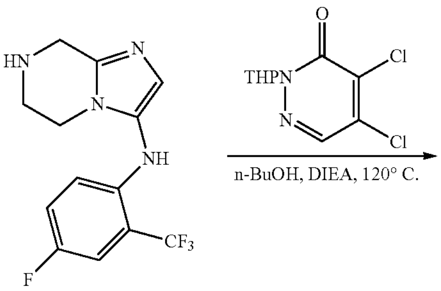

L004-5

-continued

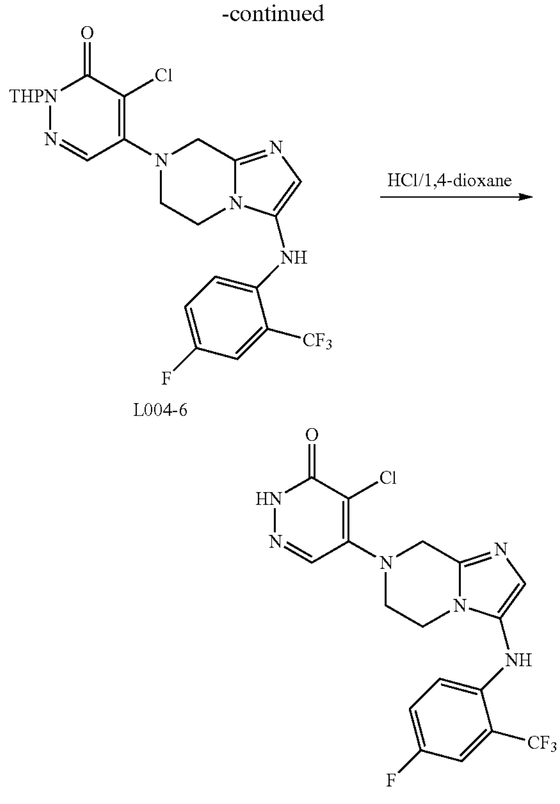

L004-6

L004

4.1 Preparation of 4-methyl-N-(pyrazin-2-yl)benzenesulfonamide (L004-1)

At room temperature, pyrazin-2-amine (6.4 g, 67.30 mmol) was added to pyridine (100 mL), and p-toluenesulfonyl chloride (15.4 g, 8.07 mmol) was added thereto, and the mixture was stirred at room temperature for 18 hours. After the mixture was concentrated under reduced pressure, the crude product was washed with methanol (30 mL) and filtered to obtain 6.80 g of 4-methyl-N-(pyrazin-2-yl)benzenesulfonamide (L004-1) as a gray solid with a yield of 36%. LC-MS $[M+H]^+$=249.9.

4.2 Preparation of Compound N-(cyanomethyl)-4-methyl-N-(pyrazin-2-yl)benzenesulfonamide (L004-2)

4-Methyl-N-(pyrazin-2-yl)benzenesulfonamide (6.8 g, 27.20 mmol) was added to DMF (30 mL), and sodium hydride (1.6 g, 40.80 mmol, 60%) was added thereto, and then the reaction solution was stirred for 30 minutes at room temperature, then bromoacetonitrile (4.9 g, 40.80 mmol) was added and the mixture was continued to stir for 30 minutes and then heated to 60° C. and reacted for 3 hours. After the temperature was returned to room temperature, the mixture was continued to stir for 14 hours. The reaction solution was poured into saturated ammonium chloride (200 mL), then extracted with ethyl acetate (3*50 mL), and the organic phase was dried over anhydrous sodium sulfate, and then filtered, and the filtrate was concentrated. The crude product was purified by silica gel column chromatography (ethyl acetate) to obtain N-(cyanomethyl)-4-methyl-N-(pyrazin-2-yl)benzenesulfonamide (L004-2, 3.5 g, yield of 45%) as a brown solid.

LC-MS $[M+H]^+$=288.9.

4.3 Preparation of Compound imidazo[1,2-a]pyrazin-3-amine (L004-3)

N-(Cyanomethyl)-4-methyl-N-(pyrazin-2-yl)benzenesulfonamide (1.8 g, 6.20 mmol) was added to a mixed solvent of trifluoroacetic acid (9.0 mL) and water (1.0 mL), and the mixture was heated to 40° C. and reacted for 2.5 hours. The mixture was concentrated under reduced pressure, and the concentrated solid was added to saturated sodium acetate (40 mL), and then the mixture was stirred for 1 hour, extracted with ethyl acetate (30 mL*6), and the organic phases were combined, concentrated under reduced pressure, and the crude product was purified by silica gel column chromatography (dichloromethane:methanol=10:1), to obtain 0.5 g of imidazo[1,2-a]pyrazin-3-amine (L004-3) as a yellow solid with a yield of 60%. LC-MS $[M+H]^+$=315.1.

4.4 Preparation of Compound N-(4-fluoro-2-(trifluoromethyl)phenyl) imidazo[1,2-a]pyrazin-3-amine (L004-4)

Imidazo[1,2-a]pyrazin-3-amine (400 mg, 2.98 mmol), 1-bromo-4-fluoro-2-(trifluoromethyl)benzene (1.45 g, 5.96 mmol), 2-dicyclohexylphosphino-2',4',6'-triisopropylbiphenyl (142 mg, 0.30 mmol) and $Cs_2CO_3$ (1.94 g, 5.96 mmol) were added to 1,4-dioxane (20 mL), under the protection of nitrogen, and tris(dibenzylideneacetone) dipalladium (273 mg, 0.30 mmol) was added thereto, and then the resulting reaction solution was heated to 120° C. and stirred for 15 hours. The reaction system was cooled down to room temperature, quenched by adding 30 mL of water, extracted with ethyl acetate (20 mL*3). The organic phases were combined, washed with saturated brine (20 mL), and dried over anhydrous sodium sulfate, filtered, and then the filtrate was concentrated under reduced pressure, and the crude product was purified by silica gel column chromatography (ethyl acetate) to obtain 250 mg of N-(4-fluoro-2-(trifluoromethyl)phenyl) imidazo[1,2-a]pyrazin-3-amine (L004-4) as a brown solid with a yield of 23%. LC-MS $[M+H]^+$=296.9.

4.5 Preparation of Compound N-(4-fluoro-2-(trifluoromethyl)phenyl)-5,6,7,8-tetrahydroimidazo[1,2-a]pyrazin-3-amine (L004-5)

N-(4-Fluoro-2-(trifluoromethyl)phenyl) imidazo[1,2-a]pyrazin-3-amine (150 mg, 0.50 mmol) was dissolved in t-BuOH (40 mL), and Pd/C (50 mg) was added thereto, and then the mixture was stirred under hydrogen atmosphere for 72 hours, and the mixture was filtered, and the filtrate was concentrated to obtain 150 mg of N-(4-fluoro-2-(trifluoromethyl)phenyl)-5,6,7,8-tetrahydroimidazo[1,2-a]pyrazin-3-amine (L004-5) as a brown solid (crude product). LC-MS $[M+H]^+$=300.9

4.6 Preparation of Compound 4-chloro-5-(3-((4-fluoro-2-(trifluoromethyl)phenyl)amino)-5,6-dihydroimidazo[1,2-a]pyrazin-7(8H)-yl)-2-(tetrahydro-2H-pyran-2-yl)pyridazin-3(2H)-one (L004-6)

N-(4-Fluoro-2-(trifluoromethyl)phenyl)-5,6,7,8-tetrahydroimidazo[1,2-a]pyrazin-3-amine (140 mg, 0.46 mmol)

and 4,5-dichloro-2-(tetrahydro-2H-pyran-2-yl)pyridazin-3(2H)-one (172 mg, 0.68 mmol) were dissolved in n-BuOH (0.7 mL), and DIEA (178 mg, 1.40 mmol) was added thereto, then the mixture was heated to 120° C. and reacted for 3 hours. The reaction solution was cooled to room temperature, concentrated under reduced pressure, and the crude product was purified by thin-layer chromatography silica gel plate (ethyl acetate) to obtain 50 mg of 4-chloro-5-(3-((4-fluoro-2-(trifluoromethyl)phenyl)amino)-5,6-dihydroimidazo[1,2-a]pyrazin-7(8H)-yl)-2-(tetrahydro-2H-pyran-2-yl)pyridazin-3(2H)-one (L004-6) as a brown solid with a yield of 21%.

LC-MS $[M+H]^+$=512.8.

4.7 Preparation of Compound 4-chloro-5-(3-((4-fluoro-2-(trifluoromethyl)phenyl)amino)-5,6-dihydroimidazo[1,2-a]pyrazin-7(8H)-yl)pyridazin-3(2H)-one (L004)

At room temperature, 4-chloro-5-(3-((4-fluoro-2-(trifluoromethyl)phenyl)amino)-5,6-dihydroimidazo[1,2-a]pyrazin-7(8H)-yl)-2-(tetrahydro-2H-pyran-2-yl)pyridazin-3(2H)-one (50 mg, 0.06 mmol) was added to DCM (3 mL), and a solution of HCl in 1,4-dioxane (4N, IN) was added thereto, and the mixture was stirred for 3 hours. The reaction solution was concentrated under reduced pressure, and the residue was dissolved in dichloromethane (30 mL), then washed with saturated sodium bicarbonate (10 mL), dried over anhydrous sodium sulfate, filtered, and the filtrate was concentrated. The crude product was purified by preparative chromatography to obtain 12.5 mg of 4-chloro-5-(3-((4-fluoro-2-(trifluoromethyl)phenyl)amino)-5,6-dihydroimidazo[1,2-a]pyrazin-7(8H)-yl)pyridazin-3 (2H)-one (L004) as a white solid with a yield of 47%.

LC-MS $[M+H]^+$=428.8.

$^1H$ NMR (400 MHz, DMSO-$d_6$) 13.04 (s, $^1H$), 7.96 (s, $^1H$), 7.42 (dd, J=8.9, 2.8 Hz, $^1H$), 7.29 (d, J=10.8 Hz, 2H), 6.83 (s, $^1H$), 6.60 (dd, J=9.1, 4.6 Hz, $^1H$), 4.65 (s, 2H), 3.78 (d, J=5.4 Hz, 4H).

Example 5 Preparation of Compound 5-(2-bromo-3-(4-fluoro-2-(trifluoromethyl)benzyl)-5,6-dihydroimidazo[1,2-a]pyrazin-7(8H)-yl)-4-chloropyridazin-3(2H)-one (L005)

L005

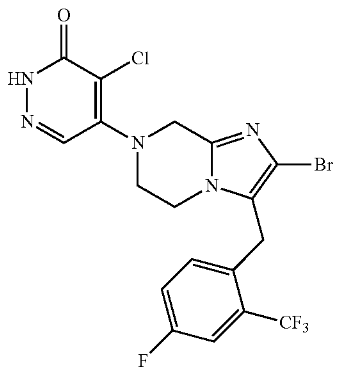

-continued

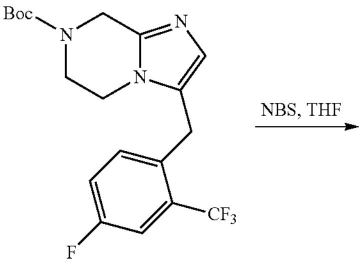

L002-6

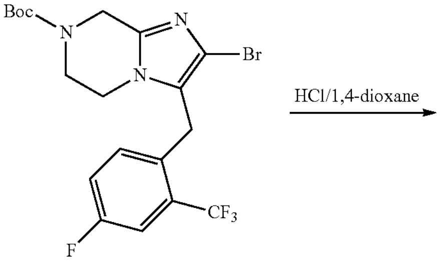

L005-1

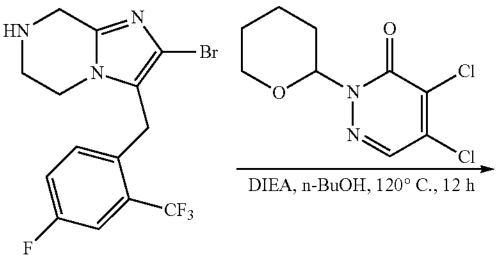

L005-2

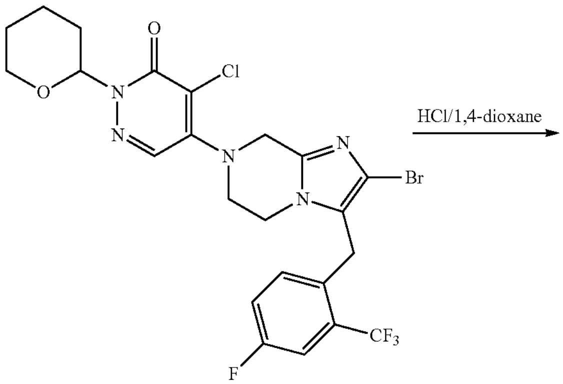

L005-3

-continued

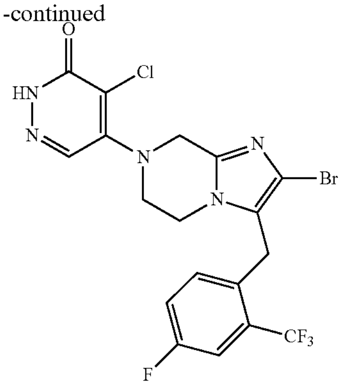

L005

5.1 Preparation of Compound tert-butyl 2-bromo-3-(4-fluoro-2-(trifluoromethyl)benzyl)-5,6-dihydroimidazo[1,2-a]pyrazine-7(8H)-carboxylate (L005-1)

tert-Butyl 3-(4-fluoro-2-(trifluoromethyl)benzyl)-5,6-dihydroimidazo[1,2-a]pyrazine-7(8H)-carboxylate (L002-6) (800 mg, 1.92 mmol) was dissolved in tetrahydrofuran (10 mL), N-bromosuccinimide (513 mg, 2.88 mmol) was added thereto in batches at −70° C. under the protection of nitrogen, and the mixture was stirred at −70° C. for 1 hour. After the reaction was completed, the mixture was quenched with water (20 mL), extracted with ethyl acetate (20 mL*4), and then the combined organic phases were washed with saturated brine (10 mL*2), dried over anhydrous sodium sulfate and filtered, and then the filtrate was concentrated. The crude product was separated by silica gel column chromatography (DCM/EA=8:1) to obtain 300 mg of yellow solid. The yield was 32%, LC-MS $[M+H]^+$=478.5.

5.2 Preparation of Compound 2-bromo-3-(4-fluoro-2-(trifluoromethyl)benzyl)-5,6,7,8-tetrahydroimidazo[1,2-a]pyrazine (L005-2) hydrochloride tert-Butyl 2-bromo-3-(4-fluoro-2-(trifluoromethyl)benzyl)-5,6-dihydroimidazo[1,2-a]pyrazine-7(8H)-carboxylate (300 mg, 0.63 mmol) was dissolved in a solution of hydrogen chloride in 1,4-dioxane (3 mL, 4 mmol/L) and the resulting solution was stirred at 25° C. for 2 hours. After the reaction was completed, the reaction solution was was concentrated under reduced pressure to obtain 260 mg of light-yellow solid as a crude product. LC-MS $[M+H]^+$ =377.8.

5.3 Preparation of Compound 5-(2-bromo-3-(4-fluoro-2-(trifluoromethyl)benzyl)-5,6-dihydroimidazo[1,2-a]pyrazin-7(8H)-yl)-4-chloro-2-(tetrahydro-2H-pyran-2-yl)pyridazin-3(2H)-one (L005-3)

2-Bromo-3-(4-fluoro-2-(trifluoromethyl)benzyl)-5,6,7,8-tetrahydroimidazo[1,2-a]pyrazine hydrochloride (207 mg, 0.50 mmol) was dissolved in n-butanol (1 mL), and 4,5-dichloro-2-(tetrahydro-2H-pyran-2-yl)pyridazin-3(2H)-one (187 mg, 0.70 mmol) and N,N-diisopropylethanamine (256 mg, 2.00 mmol) were added thereto, the reaction solution was stirred at 120° C. under the protection of nitrogen for 3 hours. After the reaction was completed, the reaction solution was concentrated under reduced pressure. The crude product was separated by silica gel column chromatography (DCM/MeOH=30:1) to obtain 200 mg of yellow solid with a yield of 67%, LC-MS $[M+H]^+$=590.4.

5.4 Preparation of Compound 5-(2-bromo-3-(4-fluoro-2-(trifluoromethyl)benzyl)-5,6-dihydroimidazo[1,2-a]pyrazin-7(8H)-yl)-4-chloropyridazin-3(2H)-one (L005)

5-(2-Bromo-3-(4-fluoro-2-(trifluoromethyl)benzyl)-5,6-dihydroimidazo[1,2-a]pyrazin-7(8H)-yl)-4-chloro-2-(tetrahydro-2H-pyran-2-yl)pyridazin-3(2H)-one (150 mg, 0.25 mmol) was dissolved in HCl/1,4-dioxane (2 mL, 4 mmol/L), and the mixture was stirred at 25° C. for 1 hour. After the mixture was concentrated under reduced pressure, saturated sodium bicarbonate solution (25 mL) was added, and the mixture was extracted with ethyl acetate (20 mL*3), and then the organic phase was dried over anhydrous sodium sulfate, filtered, and the filtrate was concentrated. The crude product was recrystallized twice with ethyl acetate to obtain 33.8 mg of white solid with a yield of 25%. LC-MS $[M+H]^+$=505.7.

$^1$H NMR (400 MHz, DMSO-$d_6$) δ 13.05 (s, $^1$H), 7.94 (s, $^1$H), 7.68 (dd, J=9.2, 2.7 Hz, $^1$H), 7.48 (td, J=8.4, 2.6 Hz, $^1$H), 7.01 (dd, J=8.7, 5.5 Hz, $^1$H), 4.66 (s, 2H), 4.10 (s, 2H), 3.86-3.77 (m, 4H).

Example 6 Preparation of Compound 4-chloro-5-(3-(4-fluoro-2-(trifluoromethyl)benzyl)-5,6,8,9-tetrahydro-7H-imidazo[1,2-d][1,4]diazepin-7-yl)pyridazin-3(2H)-one (L006)

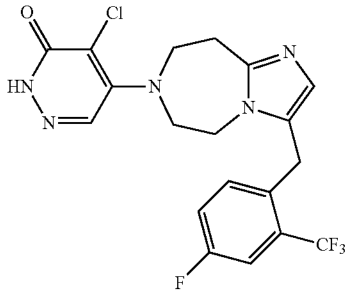

L006

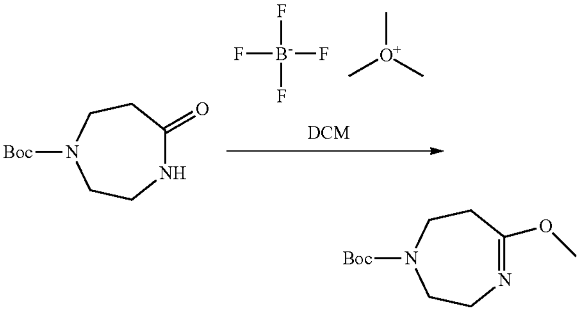

L006-1

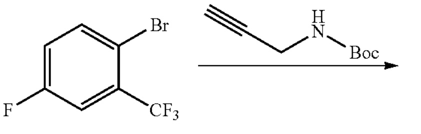

-continued

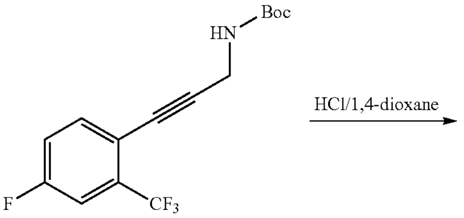

L006-2

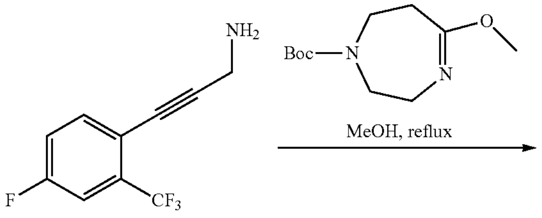

L006-3

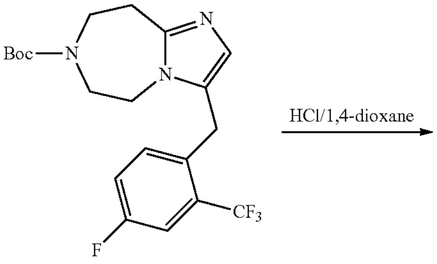

L006-4

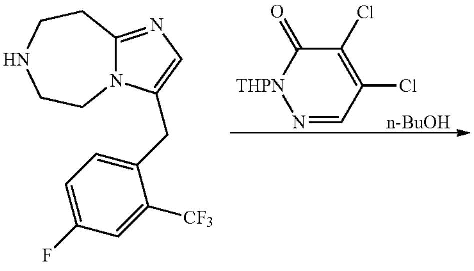

L006-5

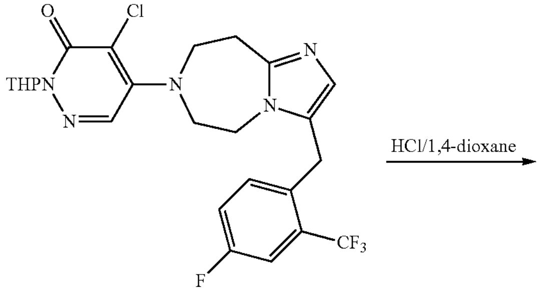

L006-6

-continued

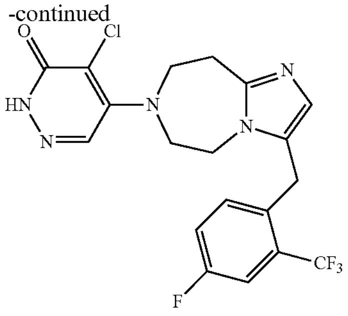

L006

6.1 Preparation of Compound tert-butyl 5-methoxy-2,3,6,7-tetrahydro-$^{1}$H-1,4-diazepine-1-carboxylate (L006-1)

1-Boc-1,4-diaza-5-cycloheptanone (500 mg, 2.32 mmol) was dissolved in dichloromethane (5 mL), and trimethyloxonium tetrafluoroborate (377 mg, 2.552 mmol) was added thereto at 0° C., and the reaction solution was stirred at 25° C. for 14 hours under nitrogen atmosphere. After the reaction was completed, saturated sodium bicarbonate solution (15 mL) was added, and the mixture was extract with ethyl acetate (20 mL*2). The organic phases were combined, washed with water (20 mL*2), dried over anhydrous sodium sulfate, filtered, and the filtrate was concentrated to obtain 400 mg of compound L006-1 as a crude product with a yield of 67.6%, which was used directly in the next reaction without purification.

$^{1}$H NMR (300 MHz, $CDCl_3$) δ 3.60 (s, 3H), 3.53-3.49 (m, 6H), 2.57-2.56 (m, 2H), 1.46 (s, 9H).

6.2 Preparation of Compound tert-butyl (3-(4-fluoro-2-(trifluoromethyl)phenyl) prop-2-yn-1-yl) carbamate (L006-2)

2-Bromo-5-fluorobenzotrifluoride (2.00 g, 8.2 mmol) was dissolved in 1,4-dioxane (20 mL), and N-Boc-aminopropyne (4.66 g, 32.8 mmol), cuprous iodide (15 mg, 0.082 mmol), diisopropylamine (960 mg, 9.51 mmol), bis-(triphenylphosphine)-palladium dichloride (230 mg, 0.33 mmol) and a solution of 10% tri-tert-butylphosphine in n-hexane (960 mg, 0.48 mmol) were added to the resulting solution. The reaction solution was stirred at 45° C. for 15 hours under nitrogen atmosphere. After the reaction was completed, the mixture was evaporated to dryness by rotary evaporation to remove the solvent, and the crude product was separated by silica gel column chromatography (PE/EA=10:1) to obtain 1.2 g of light-yellow solid containing impurity N-Boc-aminopropyne (which could be removed in the next step), with a purity of about 30% and yield of 14.6%. LC-MS $[M+H]^+$=261.9.

6.3 Preparation of Compound 3-(4-fluoro-2-(trifluoromethyl)phenyl) prop-2-yn-1-amine (L006-3)

tert-Butyl (3-(4-fluoro-2-(trifluoromethyl)phenyl) prop-2-yn-1-yl) carbamate (1.2 g, 1.1 mmol) was dissolved in dichloromethane (8 mL), and HCl/1,4-dioxane (4N, 4.5 mL) was added thereto at 0° C., and the mixture was stirred for 15 hours at 25° C. under the protection of nitrogen. After the reaction was completed, the mixture was evaporated to dryness by rotary evaporation to remove the solvent to obtain a crude product, and saturated sodium bicarbonate solution (10 mL) was added to the crude product, and then resulting mixture was extracted with ethyl acetate (10 mL*2). The organic phases were combined, dried over anhydrous sodium sulfate, filtered, and then the filtrate was concentrated to obtain 0.2 g of light-yellow liquid with a yield of 72.7%. LC-MS $[M+H]^+$=218.0.

6.4 Preparation of Compound tert-butyl 3-(4-fluoro-2-(trifluoromethyl)benzyl)-5,6,8,9-tetrahydro-7H-imidazo[1,2-d][1,4]diazepine-7-carboxylate (L006-4)

3-(4-Fluoro-2-(trifluoromethyl)phenyl) prop-2-yn-1-amine (200 mg, 0.92 mmol) was dissolved in anhydrous methanol (4 mL), and tert-butyl 5-methoxy-2,3,6,7-tetrahydro-$^1$H-1,4-diazepine-1-carboxylate (316 mg, 1.38 mmol) was added thereto, and the mixture was stirred for 5 hours at 66° C. under the protection of nitrogen. After the reaction was completed, the mixture was evaporated to dryness by rotary evaporation to remove the solvent, and the crude product was separated by silica gel column chromatography (DCM/MeOH=50:1) to obtain 200 mg of light-yellow oil with a yield of 44.5%. LC-MS $[M+H]^+$=414.0.

6.5 Preparation of Compound 3-(4-fluoro-2-(trifluoromethyl)benzyl)-6,7,8,9-tetrahydro-5H-imidazo[1,2-d][1,4]diazepine (L006-5)

tert-Butyl 3-(4-fluoro-2-(trifluoromethyl)benzyl)-5,6,8,9-tetrahydro-7H-imidazo[1,2-d][1,4]diazepine-7-carboxylate (200 mg, 0.48 mmol) was dissolved in dichloromethane (3 mL), and HCl/1,4-dioxane (4N, 2 mL) was added thereto at 0° C., and the mixture was stirred for 15 hours at 25° C. under the protection of nitrogen. The reaction solution was concentrated under reduced pressure to obtain 200 mg of crude product which was directly used in the next step without further purification.

LC-MS $[M+H]^+$=314.0.

6.6 Preparation of Compound 4-chloro-5-(3-(4-fluoro-2-(trifluoromethyl)benzyl)-5,6,8,9-tetrahydro-7H-imidazo[1,2-d][1,4]diazepin-7-yl)-2-(tetrahydro-2H-pyran-2-yl)pyridazin-3 (2H)-one (L006-6)

The crude product 3-(4-fluoro-2-(trifluoromethyl)benzyl)-6,7,8,9-tetrahydro-5H-imidazo[1,2-d][1,4]diazepine (200 mg, 0.48 mmol) was dissolved in n-butanol (0.8 mL), and 4,5-dichloro-2-(tetrahydro-2H-pyran-2-yl)pyridazin-3 (2H)-one (142 mg, 0.57 mmol) and N,N-diisopropylethanamine (186 mg, 1.44 mmol) were added thereto. The reaction solution was stirred at 120° C. for 6 hours under the protection of nitrogen. After the reaction was completed, the mixture was evaporated to dryness by rotary evaporation to remove the solvent, and the crude product was separated by preparative TLC (DCM/MeOH=20:1) to obtain 75 mg of yellow oil with a yield of 31.8%.

LC-MS $[M+H]^+$=525.8.

6.7 Preparation of Compound 4-chloro-5-(3-(4-fluoro-2-(trifluoromethyl)benzyl)-5,6,8,9-tetrahydro-7H-imidazo[1,2-d][1,4]diazepin-7-yl)pyridazin-3 (2H)-one (L006)

4-Chloro-5-(3-(4-fluoro-2-(trifluoromethyl)benzyl)-5,6,8,9-tetrahydro-7H-imidazo[1,2-d][1,4]diazepin-7-yl)-2-(tetrahydro-2H-pyran-2-yl)pyridazin-3(2H)-one (75 mg, 0.15 mmol) was dissolved in dichloromethane (2 mL), then HCl/1,4-dioxane (4N, 1 mL) was added thereto at 0° C., and the mixture was stirred at 25° C. for 4 hours under the protection of nitrogen. The mixture was evaporated to dryness by rotary evaporation to remove the solvent, and the crude product was dissolved with a small amount of dichloromethane and methanol, and solid sodium bicarbonate was added to neutralize, then the mixture was filtered, and the filtrate was concentrated, and the crude product was separated by preparative TLC (DCM/MeOH=15:1) to obtain 25.5 mg of light-yellow solid with a yield of 37.9%.

LC-MS $[M+H]^+$=441.9.

$^1$H NMR (400 MHz, $CD_3OD$) δ 7.89 (s, $^1$H), 7.52 (dd, J=8.8, 2.4 Hz, $^1$H), 7.36-7.31 (m, $^1$H), 7.21 (dd, J=8.8, 5.2 Hz, $^1$H), 6.53 (s, $^1$H), 4.16-4.13 (m, 4H), 3.70-3.65 (m, 4H), 3.28-3.25 (m, 2H).

Examples 7 to 12

The following compounds were prepared referred to the preparation method of example 6:

| Example number | Compound number | Structural formula | LC-MS $[M + H]^+$ |
|---|---|---|---|
| 7 | L007 | 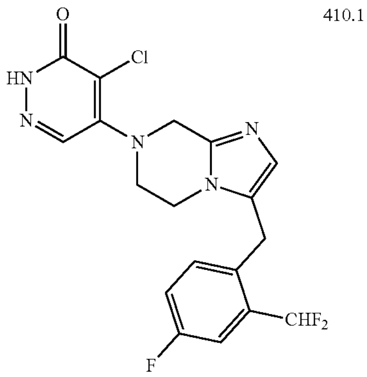 | 410.1 |
| 8 | L008 | 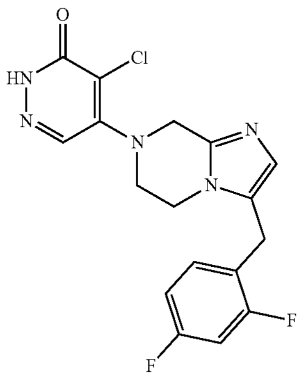 [SMILES: O=c1[nH]ncc(N2CCn3c(Cc4ccc(F)cc4F)cnc3C2)c1Cl] | 378.1 |

-continued
| Example number | Compound number | Structural formula | LC-MS [M + H]+ |
| --- | --- | --- | --- |
| 9 | L009 | 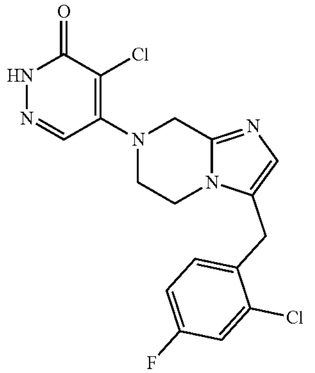 [SMILES: O=c1[nH]ncc(N2CCn3c(Cc4ccc(F)cc4Cl)cnc3C2)c1Cl] | 394.2 |
| 10 | L010 | 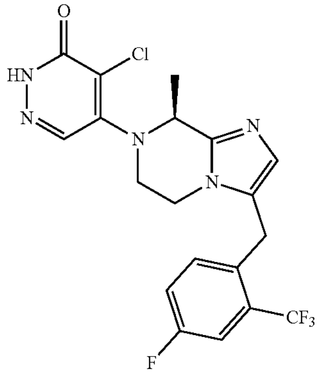 [SMILES: C[C@H]1c2ncc(Cc3ccc(F)cc3C(F)(F)F)n2CCN1c1cn[nH]c(=O)c1Cl] | 442.1 |
| 11 | L011 | 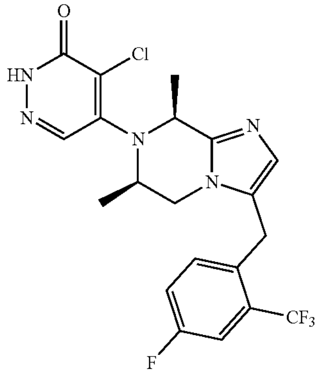 [SMILES: C[C@@H]1Cn2c(Cc3ccc(F)cc3C(F)(F)F)cnc2[C@H](C)N1c1cn[nH]c(=O)c1Cl] | 456.2 |
| 12 | L012 | 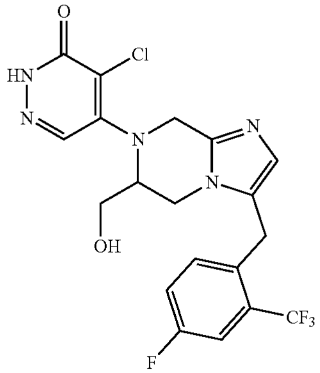 [SMILES: O=c1[nH]ncc(N2Cc3ncc(Cc4ccc(F)cc4C(F)(F)F)n3CC2CO)c1Cl] | 458.1 |
Example 13 Preparation of Compound 4-chloro-5-(3-(5-fluoro-2-(trifluoromethyl)benzyl)-5,6-dihydro-imidazo[1,2-a]pyrazin-7(8H)-yl)pyridazin-3(2H)-one (L013)
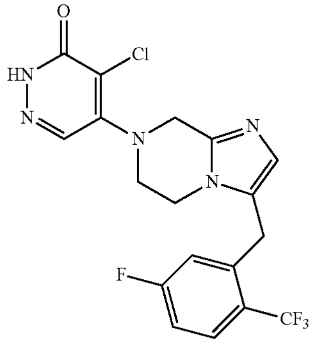
L013
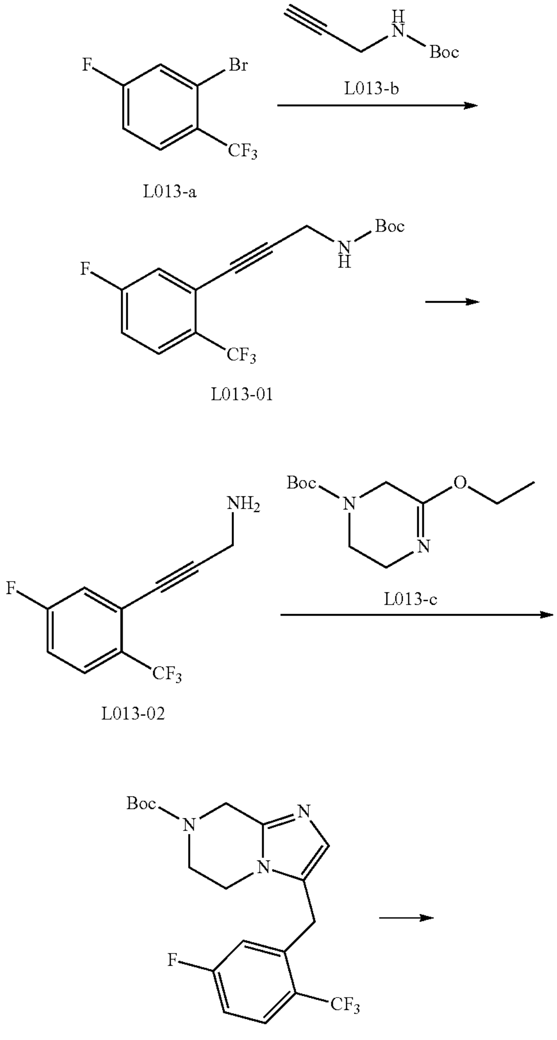
L013-03

-continued

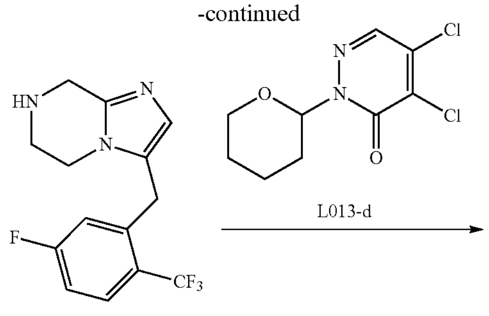

L013-d

L013-04

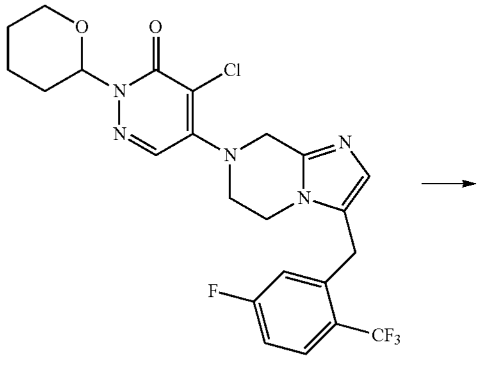

L013-05

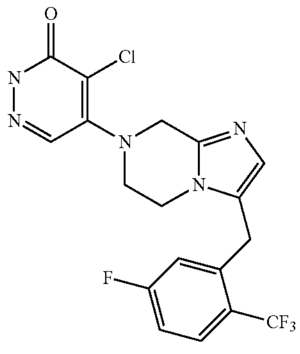

L013

13.1 Preparation of Compound L013-01

Compound L013-a (2.5 g, 10.2 mmol) was dissolved in 1,4-dioxane (25 mL), and compound L013-b (4.66 g, 32.8 mmol), bis-(triphenylphosphine)-palladium dichloride (230 mg, 0.328 mmol), cuprous iodide (15.6 mg, 0.082 mmol), triethylamine (962 mg, 9.512 mmol) and tri-tert-butylphosphine (10%) (1.20 g, 0.05 mmol) were added thereto. The mixture was stirred at 45° C. for 12 hours under the protection of nitrogen. After the reaction was completed, water (20 mL) was added thereto, and the resulting mixture was extracted with ethyl acetate (20 mL*3), and then the organic phase was washed with saturated brine (10 mL*2), dried over anhydrous sodium sulfate, and the crude product was separated by silica gel column chromatography (petroleum ether/ethyl acetate=10/1) to obtain 1.90 g of compound L013-01. LC-MS $[M-55]^+$=262.1.

13.2 Preparation of Compound L013-02

Compound L013-01 (1.90 g, 6.2 mmol) was dissolved in a solution of hydrogen chloride in 1,4-dioxane (10 mL, 4 mol/L). The mixture was stirred at 25° C. for 1 hour. After the reaction was completed, the pH of the mixture was adjusted to about 8 with sodium carbonate aqueous solution (20 mL), and then the mixture was extracted with ethyl acetate (20 mL*3), and the organic phase was washed with saturated brine (10 mL*2), dried over anhydrous sodium sulfate and concentrated to obtain 450 mg of compound L013-02. LC-MS $[M+H]^+$=218.0.

13.3 Preparation of Compound L013-03

Compound L013-02 (450 mg, 2.06 mmol) was dissolved in anhydrous methanol (4.5 mL.), and L013-c (567 mg, 2.48 mmol) was added thereto, and the mixture was stirred at 70° C. for 2 hours under the protection of nitrogen. After the reaction was completed, the reaction solution was concentrated, and the crude product was separated by silica gel column chromatography (dichloromethane/methanol=100/1) to obtain 160 mg of compound L013-03. LC-MS $[M+H]^+$=399.8.

13.4 Preparation of Compound L013-04

Compound L013-03 (160 mg, 0.324 mmol) was dissolved in a solution of hydrogen chloride in 1,4-dioxane (4 mol/L, 2 mL). The mixture was stirred at 25° C. for 1 hour. After the reaction was completed, the pH of the mixture was adjusted to about 8 with sodium carbonate aqueous solution (10 mL), then the mixture was extracted with ethyl acetate (20 mL*3), and the organic phase was washed with saturated brine (10 mL*2), dried over anhydrous sodium sulfate and concentrated to obtain compound L013-04 (100 mg).

LC-MS $[M+H]^+$=299.7.

13.5 Preparation of Compound L013-05

Compound L013-04 (100 mg, 0.33 mmol) was dissolved in n-butanol (0.5 mL), then N,N-diisopropylethylamine (129 mg, 0.1 mmol) and compound L013-d (100 mg, 0.40 mmol) were added thereto. The mixture was stirred at 120° C. for 3 hours under the protection of nitrogen. After the reaction was completed, the reaction solution was concentrated, and the crude product was separated by silica gel column chromatography (dichloromethane/methanol=30/1) to obtain 60 mg of compound L013-05.

LC-MS $[M+H]^+$=512.1.

13.6 Preparation of Compound 4-chloro-5-(3-(5-fluoro-2-(trifluoromethyl)benzyl)-5,6-dihydroimidazo[1,2-a]pyrazin-7(8H)-yl)pyridazin-3(2H)-one (L013)

Compound L013-05 (40 mg, 0.078 mmol) was dissolved in a solution of hydrogen chloride in 1,4-dioxane (4 mmol/L, 1 mL). The mixture was stirred at 25° C. for 1 hour. After the reaction was completed, the mixture was evaporated to dryness by rotary evaporation to remove the solvent, and the crude product was purified by preparative high-performance liquid chromatography (acetonitrile-water (0.1% formic acid)) to obtain 15.8 mg of compound L013. LC-MS $[M+H]^+$=427.7.

$^1$H NMR (400 MHz, DMSO-$d_6$) δ 7.95 (s, $^1$H), 7.85 (dd, J=8.8, 5.6 Hz, $^1$H), 7.34 (t, J=6.8 Hz, $^1$H), 7.05 (d, J=9.5 Hz, $^1$H), 6.54 (s, $^1$H), 4.64 (s, 2H), 4.12 (s, 2H), 3.91 (d, J=5.1 Hz, 2H), 3.83 (d, J=5.0 Hz, 2H).

Example 14 Preparation of Compound 4-((7-(5-chloro-6-oxo-1,6-dihydropyridazin-4-yl)-5,6,7,8-tetrahydroimidazo[1,2-a]pyrazin-3-yl)methyl)-3-(trifluoromethyl)benzonitrile (L014)

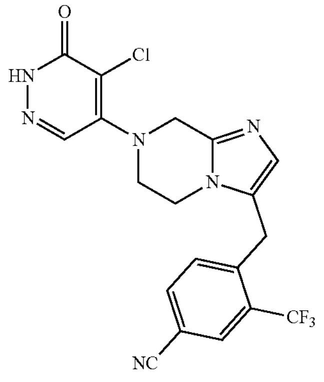

L014

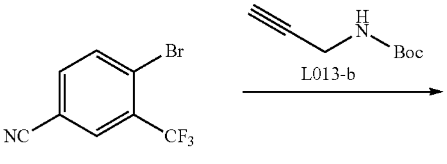

L013-b

L014-a

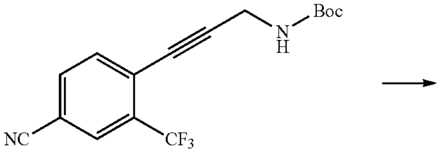

L014-01

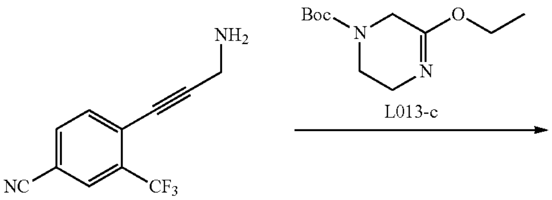

L013-c

L014-02

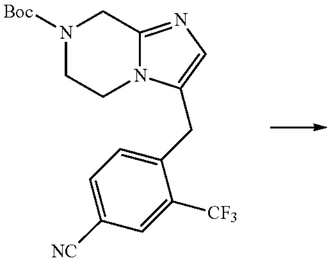

L014-03

-continued

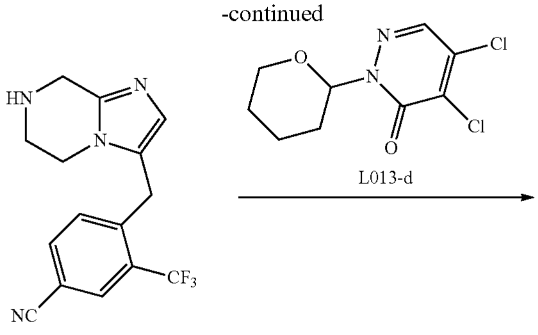

L013-d

L014-04

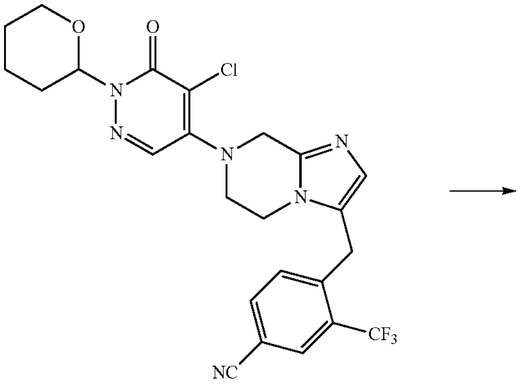

L014-05

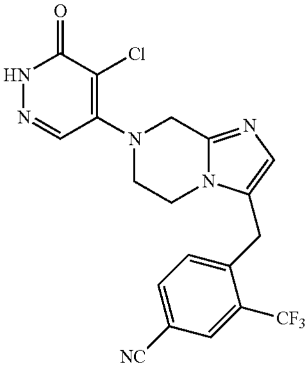

L014

14.1 Preparation of Compound L014-01

Compound L014-a (3.0 g, 12.0 mmol) was dissolved in 1,4-dioxane (30 mL), and compound L013-b (6.82 g, 48 mmol), bis-(triphenylphosphine)-palladium dichloride (340 mg, 0.04 mmol), cuprous iodide (20 mg, 0.01 mmol), triethylamine (1.41 g, 13.9 mmol) and tri-tert-butylphosphine (10%) (1.40 g, 0.06 mmol) were added thereto. The mixture was stirred at 45° C. for 12 hours under the protection of nitrogen. After the reaction was completed, water (20 mL) was added thereto, and the mixture was extracted with ethyl acetate (20 mL*3), and then the organic phase was washed with saturated brine (10 mL*2), dried over anhydrous sodium sulfate, and the crude product was separated by silica gel column chromatography (petroleum ether/ethyl acetate=10/1) to obtain 4.0 g of compound L014-01.

LC-MS $[M-55]^+=269$.

14.2 Preparation of Compound L014-02

Compound L014-01 (1.90 g, 6.2 mmol) was dissolved in a solution of hydrogen chloride in 1,4-dioxane (20 mL, 4 mol/L). The mixture was stirred at 25° C. for 1 hour. After the reaction was completed, the pH of the mixture was adjusted to about 8 with sodium carbonate aqueous solution (20 mL), and the mixture was extracted with ethyl acetate (20 mL*3), and the organic phase was washed with saturated brine (10 mL*2), dried over anhydrous sodium sulfate and concentrated to obtain 1.0 g of compound L014-02. LC-MS $[M+H]^+$=225.0.

14.3 Preparation of Compound L014-03

Compound L014-02 (1.0 g, 4.4 mmol) was dissolved in anhydrous methanol (10 mL), and compound L013-c (1.21 g, 5.28 mmol) was added thereto, and the mixture was stirred at 70° C. for 2 hours under the protection of nitrogen. After the reaction was completed, the reaction solution was concentrated, and the crude product was separated by silica gel column chromatography (dichloromethane/methanol=100/1) to obtain 500 mg of compound L014-03. LC-MS $[M+H]^+$=407.2.

14.4 Preparation of Compound L014-04

Compound L014-03 (300 mg, 0.735 mmol) was dissolved in a solution of hydrogen chloride in 1,4-dioxane (4 mol/L, 3 mL). The mixture was stirred at 25° C. for 1 hour. After the reaction was completed, the pH of the mixture was adjusted to about 8 with sodium carbonate aqueous solution (20 mL), and the mixture was extracted with ethyl acetate (30 mL*3), and the organic phase was washed with saturated brine (10 mL*2), dried over anhydrous sodium sulfate and concentrated to obtain 200 mg of compound L014-04. LC-MS $[M+H]^+$=306.8.

14.5 Preparation of Compound L014-05

Compound L014-04 (100 mg, 0.325 mmol) was dissolved in n-butanol (0.5 mL), then N,N-diisopropylethylamine (126 mg, 0,976 mmol) and compound L013-d (97 mg, 0.390 mmol) were added thereto. The mixture was stirred at 120° C. for 3 hours under the protection of nitrogen. After the reaction was completed, the reaction solution was concentrated, and the crude product was separated by silica gel column chromatography (dichloromethane/methanol=30/1) to obtain 50 mg of compound L014-05. LC-MS $[M+H]^+$=519.2.

14.6 Preparation of Compound 4-((7-(5-chloro-6-oxo-1,6-dihydropyridazin-4-yl)-5,6,7,8-tetrahydroimidazo[1,2-a]pyrazin-3-yl)methyl)-3-(trifluoromethyl)benzonitrile (L014)

Compound L014-05 (50 mg, 0.10 mmol) was dissolved in a solution of hydrogen chloride in 1,4-dioxane (4 mmol/L, 1 mL). The mixture was stirred at 25° C. for 1 hour. After the reaction was completed, the pH of the mixture was adjusted to about 8 with sodium carbonate aqueous solution (10 mL), and the mixture was extracted with ethyl acetate (10 mL*3), and the organic phase was washed with saturated brine (10 mL*2), dried over anhydrous sodium sulfate and concentrated. The crude product was washed with ethyl acetate, filtered, and the filter cake was dried to obtain 22 mg of compound L014.

LC-MS $[M+H]^+$=435.1.

$^1H$ NMR (400 MHz, DMSO-$d_6$) δ 7.95 (s, $^1H$), 7.48 (dd, J=8.8, 2.6 Hz, $^1H$), 7.27 (dd, J=8.6, 6.3 Hz, $^1H$), 7.20 (td, J=8.5, 2.6 Hz, $^1H$), 6.52 (s, $^1H$), 4.62 (s, 2H), 4.01 (s, 2H), 3.96 (t, J=5.2 Hz, 2H), 3.82 (t, J=5.2 Hz, 2H).

Example 15 Preparation of Compound 4-chloro-5-(3-(4-fluoro-2-(trifluoromethyl)benzoyl)-5,6-dihydroimidazo[1,2-a]pyrazin-7(8H)-yl)pyridazin-3(2H)-one (L015)

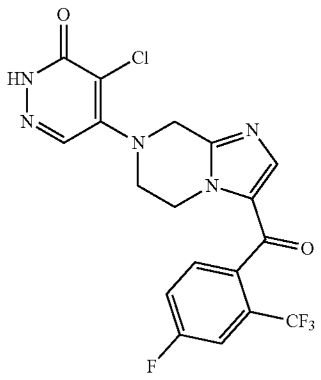

L015

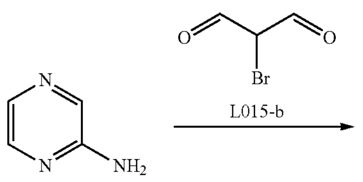

L015-a

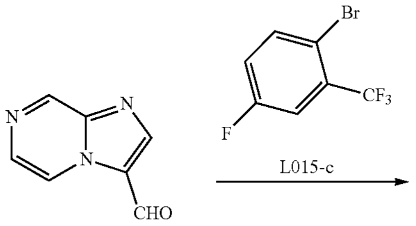

L015-01

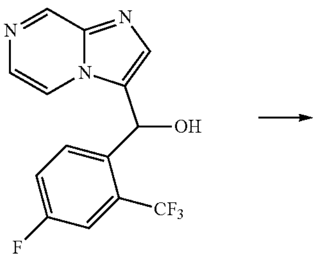

L015-02

-continued

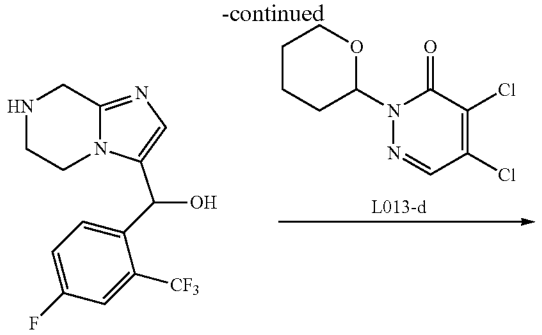

L015-03

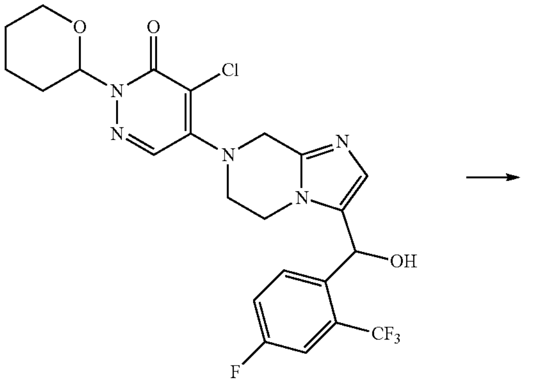

L015-04

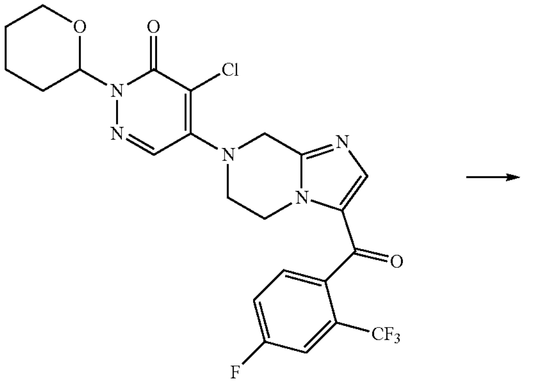

L015-05

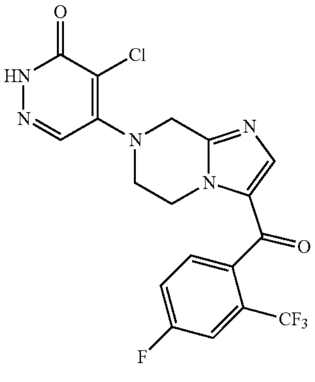

L015

15.1 Preparation of Compound L015-01

Compound L015-a (10.0 g, 0.11 mol) was dissolved in anhydrous ethanol (100 mL), and compound L015-b (15.8 g, 0.11 mmol) was added thereto, and the mixture was stirred at 90° C. for 2 hours. After the reaction was completed, the mixture was cooled to room temperature, and evaporated to dryness by rotary evaporation to remove the solvent to obtain a black viscous substance, and then 30 mL of a solution of hydrogen chloride (4 mmol/L) in 1,4-dioxane was added thereto, and the mixture was stirred at 25° C. for 12 hours. After the reaction was completed, 50 mL of water was added thereto, and the pH of the mixture was adjusted to about 8 with sodium carbonate solution, and then the mixture was extracted with ethyl acetate (50 mL*4), and the organic phase was washed with saturated brine (30 mL*2), dried over anhydrous sodium sulfate, filtered, and the filtrate was evaporated to dryness by rotary evaporation to remove the solvent and then the residue was recrystallized for three times to obtain 3.5 g of compound L015-01.

LC-MS $[M+H]^+$=148.0.

15.2 Preparation of Compound L015-02

Compound L015-c (7.47 g, 30.6 mmol) was dissolved in tetrahydrofuran (50 mL), and 2 mL of the solution was added dropwise to a solution of magnesium chips (1.47 g, 61.2 mmol) and iodine (50 mg, 2 mmol) in tetrahydrofuran (20 mL) under the protection of nitrogen, and the solution was heated with a hair dryer until the solution was clear and transparent, then the remaining solution of compound L015-c in tetrahydrofuran was added dropwise to the reaction system. The mixture was stirred at 70° C. for 1 hour, then cooled to room temperature, and added dropwise to the solution of compound L015-01 (3.00 g, 20.4 mmol) in tetrahydrofuran at −70° C. under the protection of nitrogen. The reaction mixture was stirred at −70° C. for 2 hours. After the reaction was completed, ammonium chloride solution (50 mL) was added, and the mixture was extracted with ethyl acetate (50 mL*3), and then the organic phase was washed with saturated brine (30 mL*2), dried over anhydrous sodium sulfate, filtered, and the filtrate was concentrated, and then the crude product was separated by silica gel column chromatography (dichloromethane/methanol=100/1) to obtain 3.20 g of compound L015-02. LC-MS $[M+H]^+$=312.07.

15.3 Preparation of Compound L015-03

Compound L015-02 (1.10 g, 3.50 mmol) was dissolved in tetrahydrofuran (25 mL). Wet Pd/C (10%, 400 mg) was added thereto and the resulting mixture was stirred for 12 hours at room temperature under hydrogen atmosphere. After the reaction was completed, the mixture was filtered and the filtrate was evaporated to dryness by rotary evaporation to obtain 1.00 g of compound L015-03. LC-MS $[M+H]^+$=316.2.

15.4 Preparation of Compound L015-04

Compound L015-03 (200 mg, 0.63 mmol) was dissolved in anhydrous butanol (1 mL), and L013-d (189 mg, 0.76 mmol) and N,N-diisopropylethylamine (245 mg, 1.90 mmol) were added thereto, and the mixture was stirred at 120° C. for 2 hours under the protection of nitrogen. The reaction solution was concentrated, and the crude product was separated by silica gel column chromatography (dichloromethane/methanol=100/1) to obtain 160 mg of compound L015-04.

LC-MS $[M+H]^+$=528.2.

15.5 Preparation of Compound L015-05

L015-04 (200 mg, 0.297 mmol) was dissolved in anhydrous dichloromethane (20 mL.), then Dess-Martin periodinane (630 mg, 1.485 mmol) was added thereto. The mixture was stirred at 40° C. for 8 hours under the protection of nitrogen. After the reaction was completed, the pH of the mixture was adjusted to about 9 with sodium hydroxide solution, and the mixture was extracted with dichloromethane (10 mL*3), and then the organic phase was dried over anhydrous sodium sulfate, filtered, and the filtrate was concentrated. The crude product was separated by silica gel column chromatography (dichloromethane/methanol=100/1) to obtain 150 mg of compound L015-05.

LC-MS $[M+H]^+$=526.2.

15.6 Preparation of Compound 4-chloro-5-(3-(4-fluoro-2-(trifluoromethyl)benzoyl)-5,6-dihydroimidazo[1,2-a]pyrazin-7(8H)-yl)pyridazin-3(2H)-one (L015)

L015-05 (150 mg, 0.28 mmol) was dissolved in a solution of hydrogen chloride in 1,4-dioxane (2 mL, 4 mol/L), and the mixture was stirred at 25° C. for 1 hour. The mixture was evaporated to dryness by rotary evaporation to remove the solvent to obtain a crude product, and the crude product was purified by preparative high-performance liquid chromatography to obtain 21.6 mg of compound L015.

LC-MS $[M+H]^+$=441.8.

$^1H$ NMR (400 MHz, DMSO-$d_6$) δ 13.08 (s, $^1H$), 8.02 (s, $^1H$), 7.85 (dd, J=9.3, 2.5 Hz, $^1H$), 7.79 (dd, J=8.5, 5.5 Hz, $^1H$), 7.68 (td, J=8.5, 2.5 Hz, $^1H$), 7.35 (s, $^1H$), 4.83 (s, 2H), 4.52 (t, J=5.2 Hz, 2H), 3.91 (t, J=5.3 Hz, 2H).

Example 16 Preparation of Compound 4-chloro-5-(3-(2-(trifluoromethyl)benzoyl)-5,6-dihydroimidazo[1,2-a]pyrazin-7(8H)-yl)pyridazin-3(2H)-one (L016)

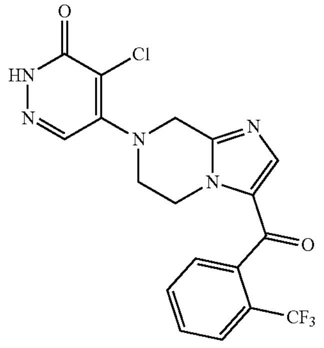

L016

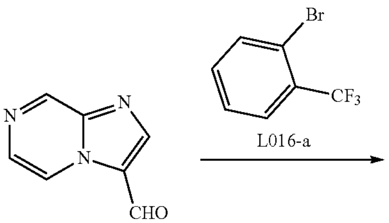

L016-a

L015-01

-continued

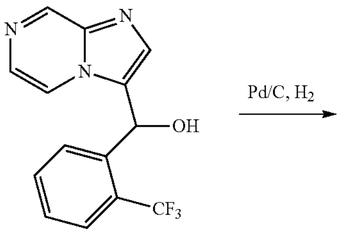

L016-01

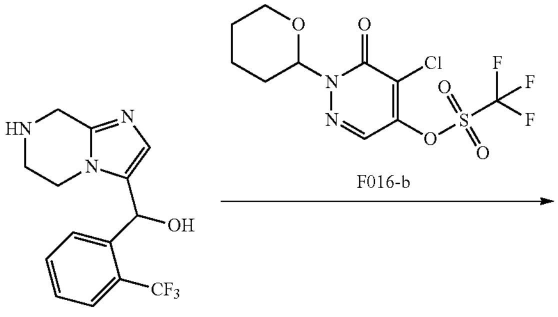

F016-b

L016-02

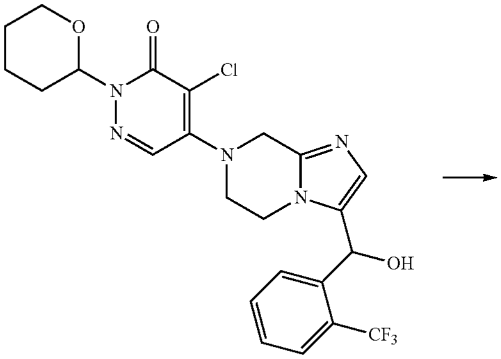

L016-03

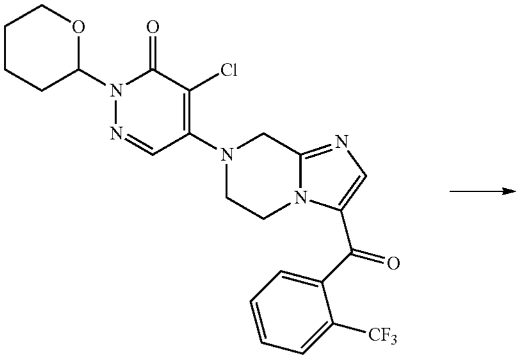

L016-04

-continued

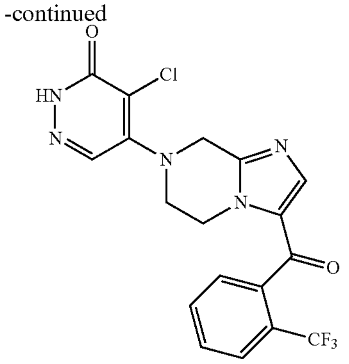

L016

16.1 Preparation of Compound L016-01

L016-a (2.55 g, 11.3 mmol) was dissolved in anhydrous tetrahydrofuran (40 mL), then the system was replaced with nitrogen for 3 times, and isopropyl magnesium bromide (2.8 M, 8.09 mL, 22.65 mmol) was added to the reaction solution at room temperature, and the reaction solution was stirred for 2 hours. Then L015-01 (2.0 g, 13.6 mmol) was added to the reaction solution, and the reaction was heated to 60° C. and reacted with stirring for 2 hours. After the reaction was completed, the reaction solution was quenched with saturated sodium chloride aqueous solution (20 mL), and then extracted with ethyl acetate (30 mL*3). The organic phases were combined, washed with saturated brine (50 mL), dried over anhydrous sodium sulfate, filtered, and the filtrate was concentrated under reduced pressure, and the crude product was purified by silica gel column chromatography (petroleum ether/ethyl acetate=3/1) to obtain 650 mg of compound L016-01.

LC-MS $[M+H]^+$=294.0.

16.2 Preparation of Compound L016-02

Compound L016-01 (600 mg, 2.05 mmol) was dissolved in tetrahydrofuran (10 mL). Then palladium/carbon (10%, 60 mg) was added thereto, and the reaction solution was reacted at 40° C. for 12 hours under hydrogen atmosphere, and the reaction was completed. The reaction solution was filtered, and the filtrate was concentrated to obtain 540 mg of compound L016-02.

LC-MS $[M+H]^+$=298.0.

16.3 Preparation of Compound L016-03

L016-02 (500 mg, 1.68 mmol), L016-b (915.05 mg, 2.52 mmol), N,N-diisopropylethylamine (652 mg, 5.05 mol) were dissolved in dimethyl sulfoxide (10 mL), and the reaction solution was heated to 60° C. and reacted for 2 hours, and the reaction was completed. The reaction solution was quenched with 20 mL of water, extracted with ethyl acetate (30 mL+3), and the organic phases were combined, washed with saturated brine (50 mL), dried over anhydrous sodium sulfate, and filtered, and the filtrate was concentrated under reduced pressure and the crude product was purified by silica gel column chromatography (petroleum ether/ethyl acetate=3/1) to obtain 510 mg of compound L016-03. LC-MS $[M+H]^+$=510.1.

16.4 Preparation of Compound L016-04

L016-03 (500 mg, 0.98 mmol) was dissolved in dichloromethane (10 mL). Dess-Martin periodinane (831.8 mg, 1.96 mmol) was added in batches and the mixture was stirred for 1 hour at room temperature. After the reaction was completed, the reaction solution was filtered, and the filtrate was concentrated under reduced pressure and the crude product was purified by silica gel column chromatography (petroleum ether/ethyl acetate=3/1) to obtain 210 mg of compound L016-04.

LC-MS $[M+H]^+$=508.0.

16.5 Preparation of Compound 4-chloro-5-(3-(2-(trifluoromethyl)benzoyl)-5,6-dihydroimidazo[1,2-a]pyrazin-7(8H)-yl)pyridazin-3(2H)-one (L016)

L016-04 (200 mg, 0.39 mmol) was dissolved in a solution of hydrogen chloride in 1,4-dioxane (2 mL, 4 mol/L), and the mixture was stirred at 25° C. for 1 hour. After the reaction was completed, the mixture was evaporated to dryness by rotary evaporation to remove the solvent to obtain a crude product, and the crude product was purified by preparative high-performance liquid chromatography to obtain 16.1 mg of compound L016.

LC-MS $[M+H]^+$=424.0;

$^1H$ NMR (400 MHz, DMSO-$d_6$) δ 13.05 (s, $^1H$), 8.00 (s, $^1H$), 7.90-7.86 (m, $^1H$), 7.82-7.74 (m, 2H), 7.67 (d, J=7.2 Hz, $^1H$), 7.25 (s, $^1H$), 4.81 (s, 2H), 4.51 (t, J=5.6 Hz, 2H), 3.92-3.88 (m, 2H).

Example 17 Preparation of Compound 4-chloro-5-(3-(4-chloro-2-(trifluoromethyl)benzoyl)-5,6-dihydroimidazo[1,2-a]pyrazin-7(8H)-yl)pyridazin-3(2H)-one (L017)

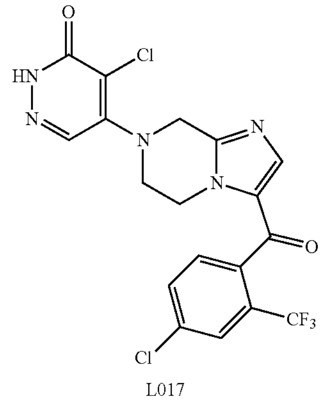

L017

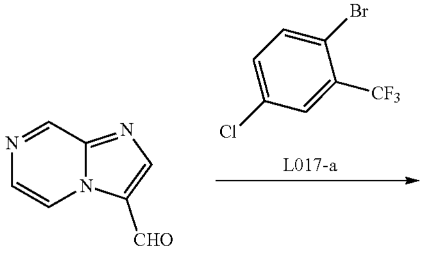

L015-01

-continued

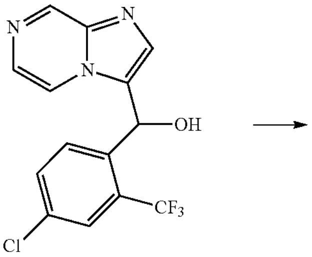

L017-01

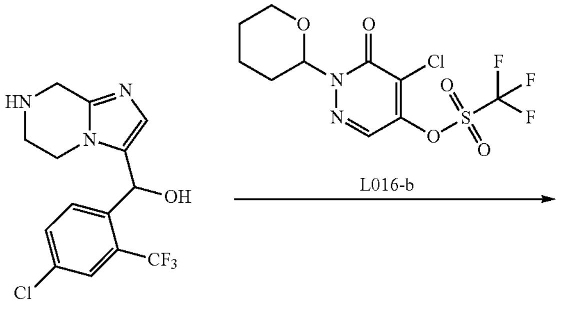

L017-02

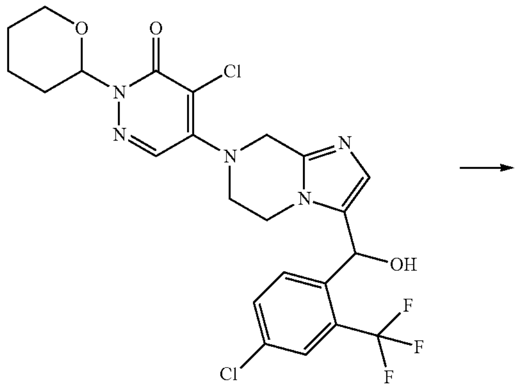

L017-03

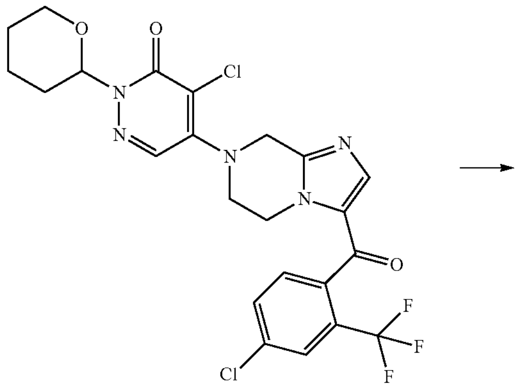

L017-04

-continued

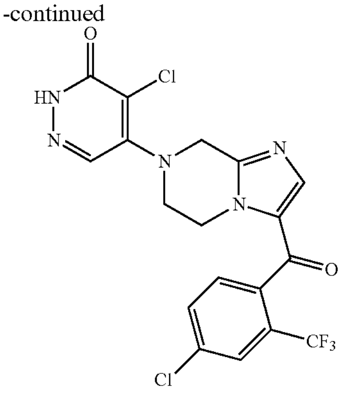

L017

17.1 Preparation of Compound L017-01

Compound L017-a (4.36 g, 16.80 mmol) was weighed and added to anhydrous tetrahydrofuran (80 mL), then the system was replaced with nitrogen for three times, and isopropyl magnesium bromide (2.8 M, 5 mL, 14.00 mmol) was slowly added dropwise thereto at room temperature, and the reaction solution was reacted at room temperature for 2 hours after the dropwise addition was completed. Then L015-01 (1.85 g, 12.60 mmol) solid was added to the reaction system, and the mixture was heated to 40° C. and reacted at this temperature for 4 hours, and then the reaction was completed. Saturated ammonium chloride aqueous solution (100 mL) was added slowly to the reaction to quench the reaction, and the mixture was extracted with dichloromethane (100 mL*3), then the organic phase was washed with saturated brine (50 mL*3), dried over anhydrous sodium sulfate, filtered and concentrated, and then the crude product was separated by silica gel column chromatography (dichloromethane/methanol=10/1) to obtain 2.5 g of compound L017-01.

LC-MS $[M+H]^+$=328.0.

17.2 Preparation of Compound L017-02

Compound L017-01 (2.4 g, 7.32 mmol) was dissolved in tetrahydrofuran (30 mL), then palladium/carbon (10%, 1.0 g) was added thereto, and the system was replaced with nitrogen for three times, and the reaction solution was reacted at 40° C. for 16 hours under hydrogen atmosphere. After the reaction was completed, the reaction solution was filtered, and the filtrate was concentrated to dryness, and the crude product was purified by silica gel column chromatography (dichloromethane/methanol=10/1) to obtain 1.0 g of compound L017-02. LC-MS $[M+H]^+$=332.0.

17.3 Preparation of Compound L017-03

Compound L017-02 (0.5 g, 1.06 mmol) and compound L016-b (0.54 g, 1.48 mmol) were weighed and dissolved in dimethyl sulfoxide (5.0 mL), and diisopropylethylamine (0.41 g, 3.17 mmol) was added thereto, then the reaction solution was stirred at 80° C. for 16 hours, and the reaction was completed. After the reaction solution was lowered to 30° C., ethyl acetate (30 mL) and water (20 mL) were added, and the mixture was stirred and the phases were separated. The aqueous phase was extracted with ethyl acetate (20 mL*2), and then the organic phases were combined, washed with saturated brine (50 mL), dried over anhydrous sodium sulfate, and concentrated to obtain a crude product, which was then purified by silica gel column chromatography (dichloromethane/methanol=10/1) to obtain 0.4 g of compound F017-03. LC-MS $[M+H]^+$=544.0.

17.4 Preparation of Compound L017-04

L017-03 (0.4 g, 734.81 mmol) was weighed and dissolved in dichloromethane (8.0 mL), and Dess-Martin periodinane (0.94 g, 2.2 mol) was added thereto, then the mixture was stirred at room temperature for 16 hours. The reaction was completed. The reaction solution was filtered, and the filtrate was concentrated, and the crude product was purified by silica gel column chromatography (dichloromethane/methanol=10/1) to obtain 0.35 g of compound L017-04.

LC-MS $[M+H]^+$=542.0.

17.5 Preparation of Compound 4-chloro-5-(3-(4-chloro-2-(trifluoromethyl)benzoyl)-5,6-dihydroimidazo[1,2-a]pyrazin-7(8H)-yl)pyridazin-3(2H)-one (L017)

L017-04 (0.35 g, 645.35 μmol) was weighed into a reaction flask, and a solution of hydrogen chloride in 1,4-dioxide (4 M, 4 mL) was added thereto, and the mixture was reacted at room temperature for 3 hours. The reaction was completed. The reaction solution was concentrated, and the crude product was purified by preparative high-performance liquid chromatography to obtain 42.8 mg of compound L017.

LC-MS $[M+H]^+$=458.0;

$^{1}H$ NMR (400 MHz, DMSO-$d_6$) § 13.06 (s, $^{1}H$), 8.01 (d, J=3.4 Hz, 2H), 7.90 (dd, J=8.2, 1.8 Hz, $^{1}H$), 7.74 (d, J=8.4 Hz, $^{1}H$), 7.37 (s, $^{1}H$), 4.83 (s, 2H), 4.51 (t, J=5.2 Hz, 2H), 3.91 (t, J=5.2 Hz, 2H), 2.07 (s, $^{1}H$).

Example 18 Preparation of Compound 4-chloro-5-(3-(5-fluoro-2-(trifluoromethyl)benzoyl)-5,6-dihydroimidazo[1,2-a]pyrazin-7(8H)-yl)pyridazin-3(2H)-one (L018A) and compound 4-chloro-5-(3-(2-fluoro-5-(trifluoromethyl)benzoyl)-5,6-dihydroimidazo[1,2-a]pyrazin-7(8H)-yl)pyridazin-3(2H)-one (L018B)

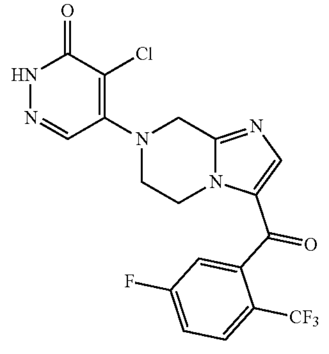

L018A

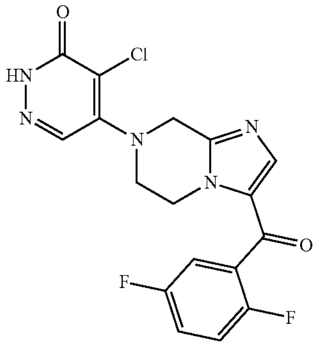

L018B

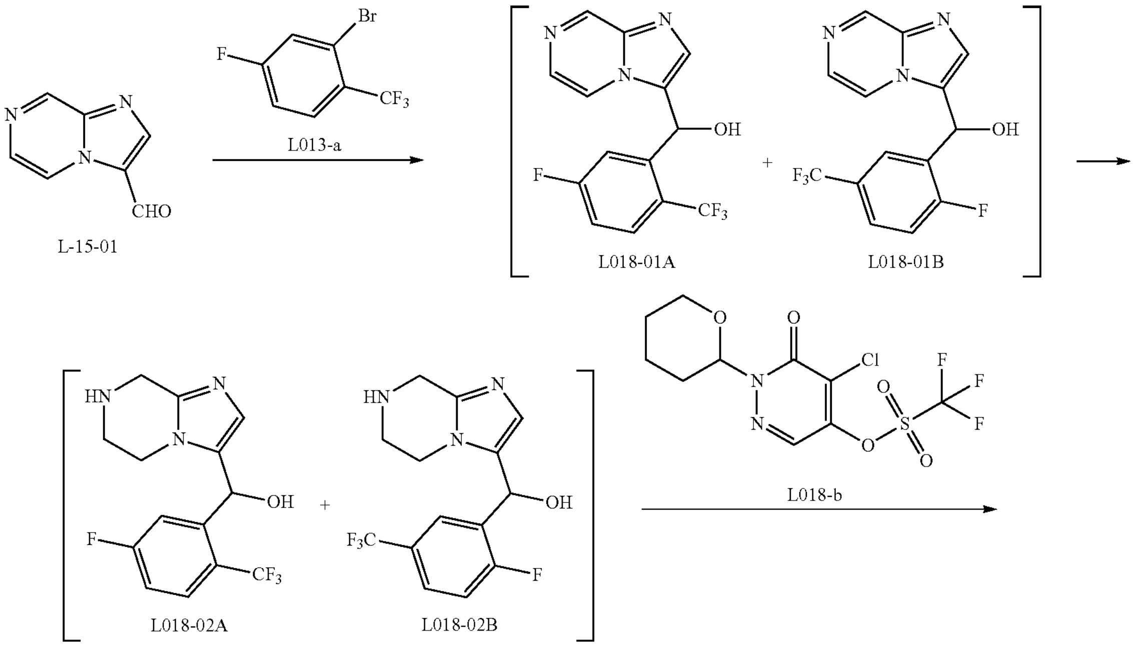

-continued

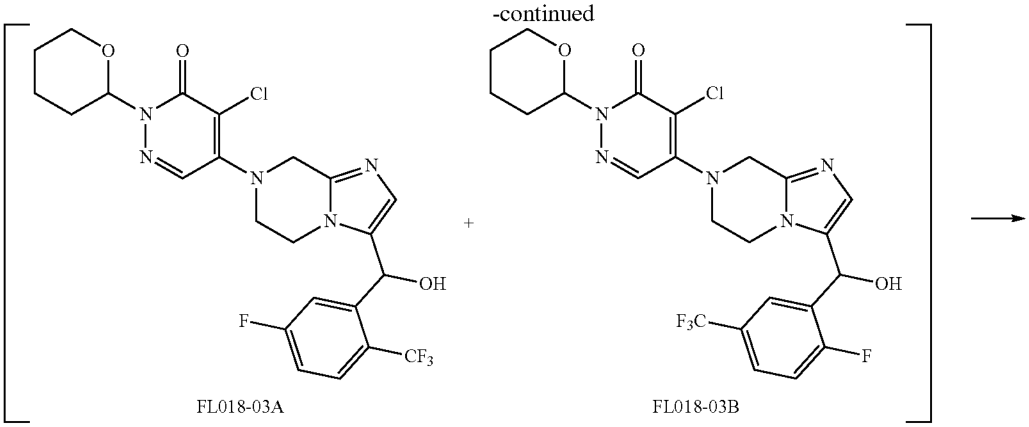

FL018-03A FL018-03B

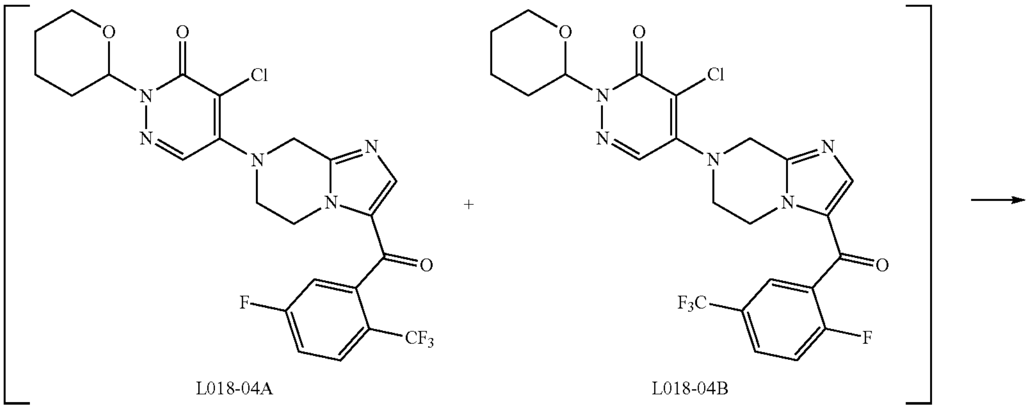

L018-04A L018-04B

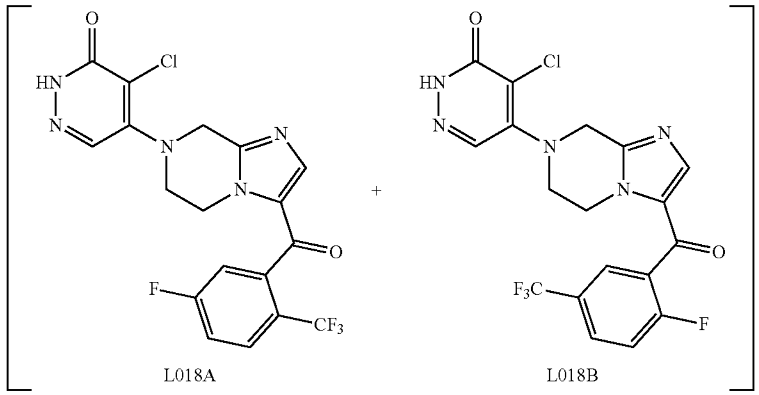

L018A L018B 18.1 Preparation of Compounds L018-01A and L018-01B

Compound L013-a (1 g, 4.11 mmol) was dissolved in tetrahydrofuran (15 mL), and after the system was replaced with nitrogen and the temperature was reduced to −78° C., and a solution of 2.5M n-butyl lithium (1.8 mL, 4.52 mmol) in hexane was added thereto, and the reaction solution was reacted at −78° C. for 1 hour. L015-01 (605 mg, 4.11 mmol) was added to the reaction system, and after the addition was completed, the reaction system was naturally raised to room temperature and reacted overnight, then the reaction was completed. The reaction solution was diluted with water (80 mL) slowly, and then extracted with ethyl acetate (30 mL*3). The organic phases were combined, washed with saturated brine (50 mL), dried over anhydrous sodium sulfate, filtered, and the filtrate was concentrated under reduced pressure to obtain a crude product. The crude product was purified by silica gel column chromatography (dichloromethane/methanol=50/1 to 15/1) to obtain compounds L018-01A and L018-01B (600 mg). LC-MS $[M+H]^+$ =312.0.

18.2 Preparation of Compounds L018-02A and L018-02B

Compounds L018-01A and L018-01B (270 mg, 0.87 mmol) was dissolved in methanol (20 mL), and anhydrous palladium/carbon (10%) was added thereto, and the system was replaced with nitrogen, then the reaction was stirred at room temperature for 3 hours, and the reaction was completed. The reaction solution was filtered, washed with methanol (3 mL) for three times, and the filtrate was concentrated under reduced pressure to obtain a product, which could be directly used in the next step without purification. Compounds L018-02A and L018-02B (230 mg) were obtained. LC-MS $[M+H]^+$=316.0.

18.3 Preparation of L018-03A and L018-03B

L018-02A, L018-02B (230 mg, 0.73 mmol) and L016-b (291 mg, 0.80 mmol) were dissolved in dimethyl sulfoxide (6 mL), and then N,N-diisopropylethanamine (283 mg, 2.19 mmol) were added thereto, and the mixture was reacted at 60° C. overnight and the reaction was completed. The reaction solution was poured into water (50 mL), and extracted with ethyl acetate (20 mL*3). The organic phases were combined, washed with saturated brine (50 mL), dried over anhydrous sodium sulfate, filtered, and the filtrate was concentrated under reduced pressure to obtain a crude product. The crude product was purified by silica gel column chromatography (DCM/MeOH=50/1 to 20/1) to obtain L018-03A and L018-03B (270 mg).

LC-MS $[M+H]^+$=528.0.

18.4 Preparation of Compounds L018-04A and L018-04B

L018-03A and L018-03B (270 mg, 0.51 mmol) were dissolved in dichloromethane (10 mL), and Dess-Martin periodinane (434 mg, 1.02 mmol) was added thereto in batches at 0° C., and the mixture was raised to room temperature and reacted for 30 minutes. The reaction solution was added with saturated sodium thiosulfate aqueous solution (30 mL), and then extracted with dichloromethane (20 mL*3). The organic phases were combined, washed with saturated brine (50 mL), dried over anhydrous sodium sulfate, filtered, and the filtrate was concentrated under reduced pressure to obtain a crude product. The crude product was purified by silica gel column chromatography (dichloromethane/methanol=50/1 to 20/1) to obtain L018-04A and L018-04B (230 mg). LC-MS $[M+H]^+$=526.0.

18.5 Preparation of Compound 4-chloro-5-(3-(5-fluoro-2-(trifluoromethyl)benzoyl)-5,6-dihydroimidazo[1,2-a]pyrazin-7(8H)-yl)pyridazin-3(2H)-one (L018A) and compound 4-chloro-5-(3-(2-fluoro-S-(trifluoromethyl)benzoyl)-5,6-dihydroimidazo[1,2-a]pyrazin-7(8H)-yl)pyridazin-3(2H)-one (L018B)

Compounds L018-04A and L018-04B (230 mg, 0.44 mmol) was placed in a 25 mL single-necked flask, and a solution of 4M hydrogen chloride in dioxane (5 mL) was added thereto, and the reaction was stirred at room temperature for 30 minutes, and the reaction was completed. The reaction solution was concentrated under reduced pressure to obtain a crude product, and the crude product was purified by preparative high-performance liquid chromatography in a water/acetonitrile system to obtain compound L018A (26.8 mg) and compound L018B (37.0 mg) after lyophilization.

L018A: LC-MS $[M+H]^+$=442.0; 1H NMR (400 MHz, DMSO-$d_6$) δ 13.07 (s, $^1$H), 8.01 (s, $^1$H), 7.98 (s, $^1$H), 7.62 (t, J=8.4 Hz, 2H), 7.41 (s, $^1$H), 4.83 (s, 2H), 4.51 (t, J=5.2 Hz, 2H), 3.91 (t, J=5.2 Hz, 2H).

L018B: LC-MS $[M+H]^+$=442.0; 1H NMR (400 MHz, DMSO-$d_6$) & 13.07 (s, $^1$H), 8.10-7.90 (m, 3H), 7.64 (t, J=9.2 Hz, $^1$H), 7.55 (s, $^1$H), 4.83 (s, 2H), 4.52 (t, J=4.8 Hz, 2H), 3.91 (t, J=4.8 Hz, 2H).

Example 19 Preparation of Compound 4-(7-(5-chloro-6-oxo-1,6-dihydropyridazin-4-yl)-5,6,7,8-tetrahydroimidazo[1,2-a]pyrazine-3-carbonyl)-3-(trifluoromethyl)benzonitrile (L019)

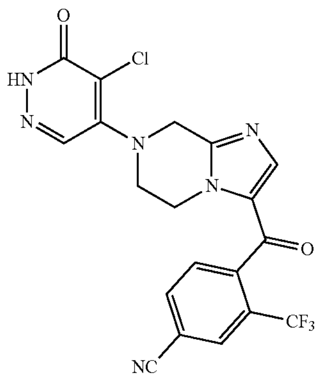

L019

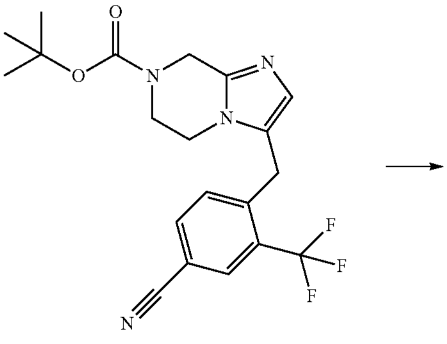

L014-03

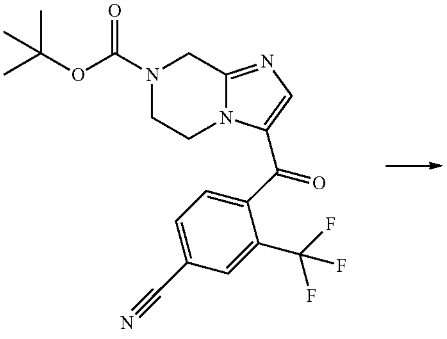

L019-01

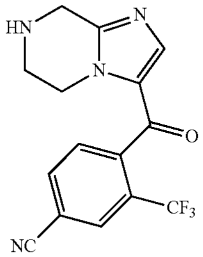

L019-02

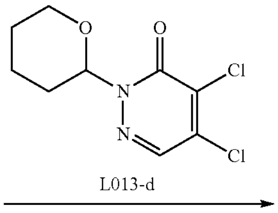

-continued

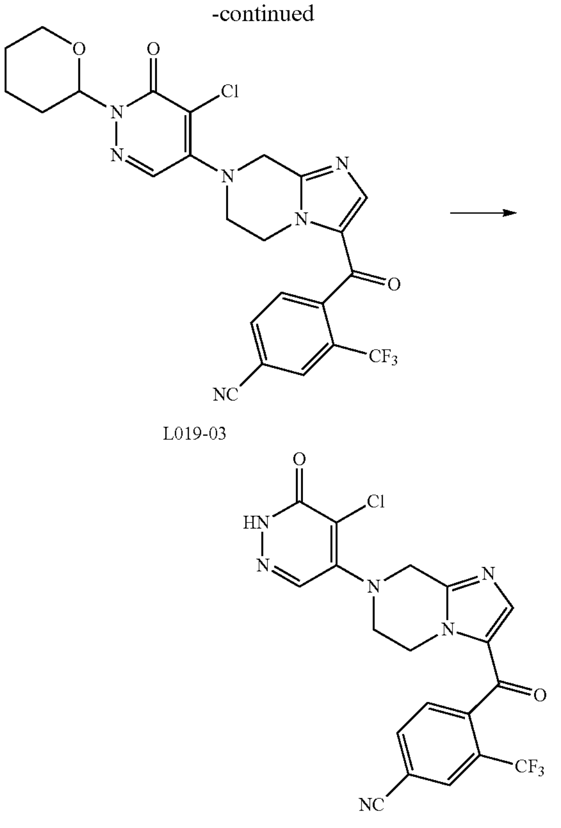

L019-03

L019

19.1 Preparation of Compound L019-01

Compound L014-03 (2 g, 4.92 mmol), acetic acid (295.52 mg, 4.92 mmol) and ferrous chloride tetrahydrate (97.83 mg, 0.492 mmol) were dissolved in dimethyl sulfoxide (20 mL), and the system was replaced with nitrogen for 3 times, and then the reaction solution was reacted at 100° C. for 24 hours. After the reaction was completed, the reaction solution was quenched with water (20 mL), and extracted with ethyl acetate (30 mL*3). The organic phases were combined, washed with saturated brine (50 mL), and dried over anhydrous sodium sulfate, and then filtered, and the filtrate was concentrated under reduced pressure, and the crude product was purified by silica gel column chromatography (petroleum ether/ethyl acetate=100/5) to obtain compound L019-01 (600 mg).

LC-MS $[M+H]^+$=421.10.

19.2 Preparation of Compound L019-02

L019-01 (600 mg, 1.43 mmol) was dissolved in hydrochloric acid/dioxane (4 M, 10 mL) and the reaction solution was reacted at room temperature for 2 hours. After the reaction was completed, the reaction solution was filtered, and the filter cake was compound L019-02 (500 mg). LC-MS $[M+H]^+$=321.05.

19.3 Preparation of Compound L019-03

Compound L019-02 (250 mg, 0.78 mmol), L013-d (233 mg, 0.94 mmol) and N,N-diisopropylethylamine (504 mg, 3.9 mmol) were dissolved in dimethylsulfoxide (3 mL). The reaction was reacted at 80° C. for 4 hours, and the reaction was completed. The reaction solution was quenched with water (20 mL), extracted with ethyl acetate (30 mL*3), and the organic phases were combined, washed with saturated brine (50 mL), dried over anhydrous sodium sulfate, and filtered, and the filtrate was concentrated under reduced pressure, and the crude product was purified by silica gel column chromatography (dichloromethane/methanol=10/1) to obtain compound L019-03 (200 mg). LC-MS $[M+H]^+$=533.10.

19.4 Preparation of Compound 4-(7-(5-chloro-6-oxo-1,6-dihydropyridazin-4-yl)-5,6,7,8-tetrahydroimidazo[1,2-a]pyrazine-3-carbonyl)-3-(trifluoromethyl)benzonitrile (L019)

L019-03 (200 mg, 0.37 mmol) was dissolved in hydrochloric acid/dioxane (4 M, 10 mL) and the reaction solution was reacted at room temperature for 2 hours, and the reaction was completed. After the reaction solution was evaporated to dryness by rotary evaporation to remove the solvent to obtain a crude product, and the crude product was purified by preparative high-performance liquid chromatography to obtain 31 mg of compound L019. LC-MS $[M+H]^+$=449.00;

$^1H$ NMR (400 MHz, DMSO-$d_6$) δ 13.06 (s, $^1H$), 8.50 (s, $^1H$), 8.31 (d, J=8.0 Hz, $^1H$), 8.01 (s, $^1H$), 7.91 (d, J=8.0 Hz, $^1H$), 7.39 (s, $^1H$), 4.83 (s, 2H), 4.52 (t, J=5.2 Hz, 2H), 3.92 (t, J=5.2 Hz, 2H).

Example 20 Preparation of Compound 4-chloro-5-(3-(4-methoxy-2-(trifluoromethyl)benzoyl)-5,6-dihydroimidazo[1,2-a]pyrazin-7(8H)-yl)pyridazin-3(2H)-one (L020)

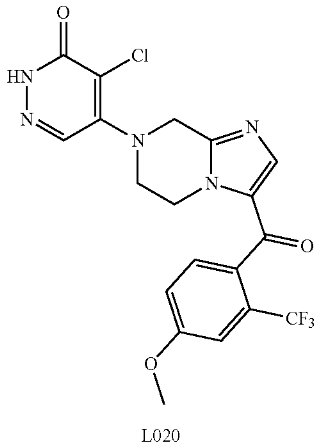

L020

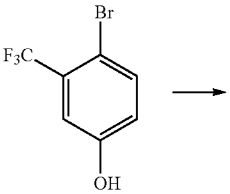

L020-a

-continued

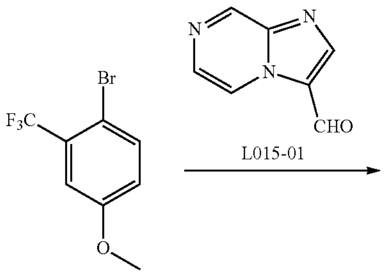

L020-01

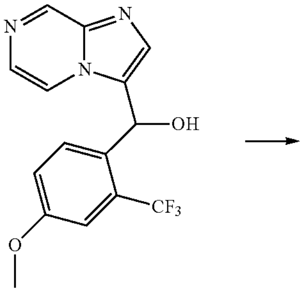

L020-02

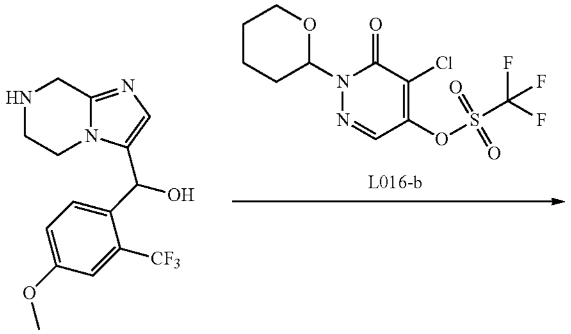

L020-03

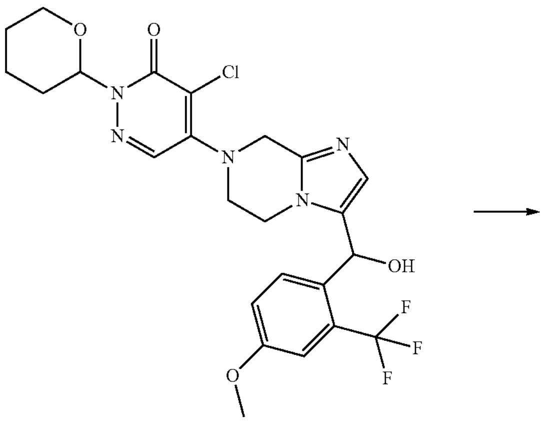

L020-04

-continued

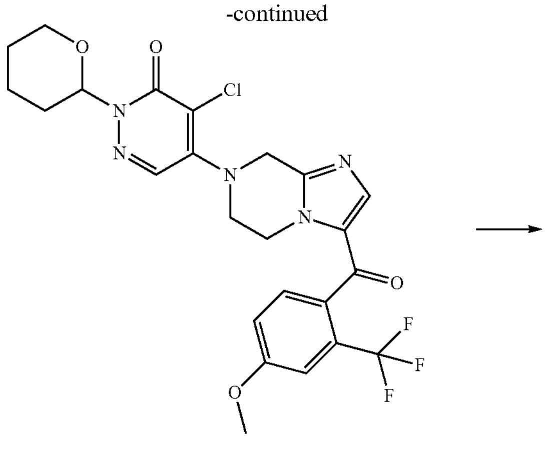

L020-05

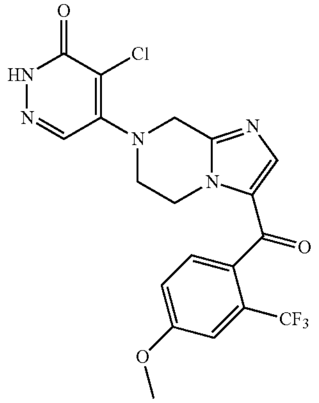

L020

20.1 Preparation of Compound L020-01

Compound L020-a (1.5 g, 6.22 mmol) was dissolved in anhydrous N,N-dimethylformamide (30 mL), and sodium hydride (298 mg, 60%, 7.46 mmol) was added thereto at 0° C. under the protection of nitrogen, and then the reaction solution was stirred for 0.5 hours, and methyl iodide (2.65 g, 18.7 mmol) was added thereto. After the addition was completed, the mixture was raised to room temperature slowly and continued to stir for 2 hours. After the reaction was completed, the reaction solution was poured into water (100 mL), extracted with ethyl acetate (50 mL*3), then the organic phase was concentrated under reduced pressure, and the crude product was purified by silica gel column chromatography (PE:EA=6:1-2:1) to obtain 1.2 g of compound L020-01.

20.2 Preparation of Compound L020-02

Compound L020-01 (1.2 g, 4.71 mmol) was dissolved in anhydrous tetrahydrofuran (10 mL), and then n-butyllithium (2.8 mL, 7.07 mmol) was added dropwise thereto at −78° C. under the protection of nitrogen, and the mixture was stirred at this temperature for 1 hour, and then compound L015-01 (692 mg, 4.71 mmol) was added thereto. After the addition was completed, the mixture was raised to room temperature slowly and stirred for 16 hours. After the reaction was completed, the reaction solution was quenched with saturated ammonium chloride aqueous solution (100 mL), and extracted with ethyl acetate (50 mL*3). The organic phase was concentrated under reduced pressure, and the crude product was purified by silica gel column chromatography to obtain 400 mg of compound L020-02. LC-MS $[M+H]^+$=324.05.

20.3 Preparation of Compound L020-03

Compound L020-02 (400 mg, 1.24 mmol) was dissolved in methanol (10 mL), then dry palladium/carbon (10%, 50 mg) was added thereto, and the reaction solution was stirred at 40° C. under hydrogen atmosphere (15 Psi) for 16 hours. After the reaction was completed, the reaction solution was filtered, and the filtrate was concentrated under reduced pressure to obtain 100 mg of compound L020-03 as a crude product. LC-MS $[M+H]^+$=328.10.

20.4 Preparation of Compound L020-04

Compound L020-03 (100 mg, 0.306 mmol) and compound L016-b (91.4 mg, 0.367 mmol) were dissolved in dimethyl sulfoxide (1 mL), then N,N-diisopropylethylamine (78.9 mg, 0.367 mmol) was added thereto and stirred at 100° C. for 2 hours. After the reaction was completed, the reaction solution was poured into water (50 mL), extracted with ethyl acetate (30 mL*3), and the organic phase was concentrated under reduced pressure, and then the crude product was purified by thin-layer chromatography silica gel plate (dichloromethane/methanol=10/1) to obtain 60 mg of compound L020-04.

20.5 Preparation of Compound L020-05

Compound L020-04 (60 mg, 0.111 mmol) was dispersed in dichloromethane (2 mL), and Dess-Martin periodinane (71 mg, 0.167 mmol) was added to the resulting suspension in batches at 25° C. and the mixture was stirred for 1 hour. After the reaction was completed, the reaction solution was quenched with saturated sodium sulfite aqueous solution (50 mL), extracted with ethyl acetate (30 mL*3), and the organic phase was concentrated under reduced pressure, and then the crude product was purified by thin-layer chromatography silica gel plate (dichloromethane/methanol=10/1) to obtain 30 mg of compound L020-05.

20.6 Preparation of Compound 4-chloro-5-(3-(4-methoxy-2-(trifluoromethyl)benzoyl)-5,6-dihydroimidazo[1,2-a]pyrazin-7(8H)-yl)pyridazin-3(2H)-one (L020)

Compound L020-05 (30 mg, 55.8 μmol) was dissolved in a solution of hydrogen chloride in 1,4-dioxane (4M, 2 mL), and the resulting solution was stirred at 25° C. for 1 hour. After the reaction was completed, the reaction solution was concentrated under reduced pressure at room temperature. The pH of the mixture was adjusted to 9 with $NaHCO_3$ aqueous solution, and the mixture was extracted with ethyl acetate (5 mL*3), then the organic phase was concentrated under reduced pressure, and the crude product was purified by preparative high-performance liquid chromatography to obtain 3.3 mg of compound L020.

LC-MS $[M+H]^+$=454.05;

$^1H$ NMR (400 MHz, DMSO-$d_6$) § 13.04 (br. s, $^1H$), 8.01 (s, $^1H$), 7.67 (d, J=8.4 Hz, $^1H$), 7.36 (d, J=2.4 Hz, $^1H$), 7.33 (dd, J=8.4, 2.5 Hz, $^1H$), 7.29 (s, $^1H$), 4.82 (s, 2H), 4.53-4.48 (m, 2H), 3.94-3.88 (m, 5H).

Example 21 Preparation of Compound 4-chloro-5-(3-(4-hydroxy-2-(trifluoromethyl)benzoyl)-5,6-dihydroimidazo[1,2-a]pyrazin-7(8H)-yl)pyridazin-3(2H)-one (L021)

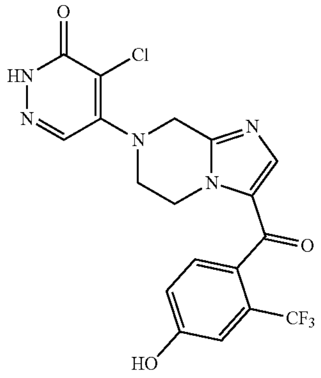

L021

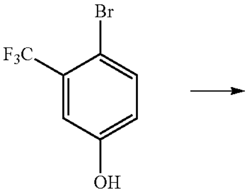

L020-a

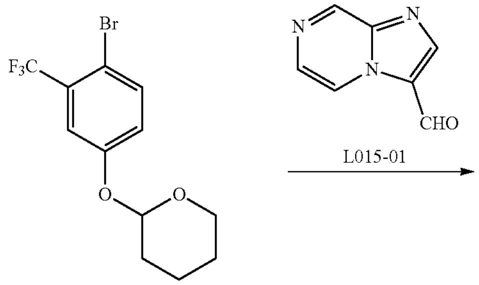

L021-01

L015-01

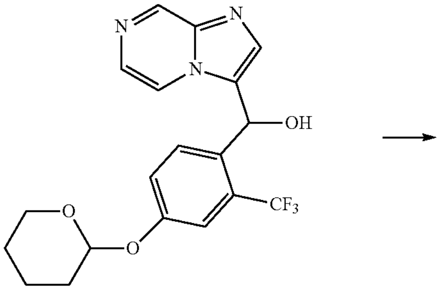

L021-02

-continued

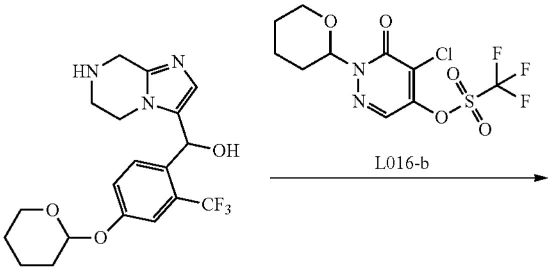

L021-03

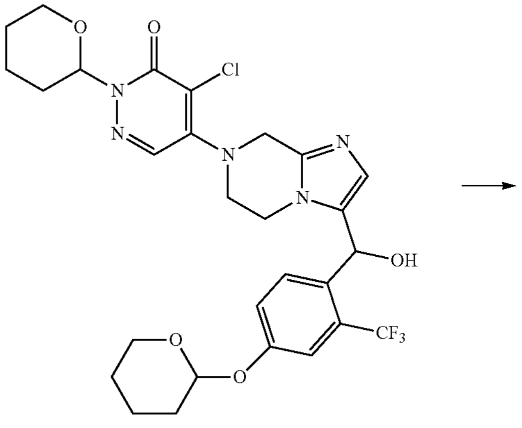

L021-04

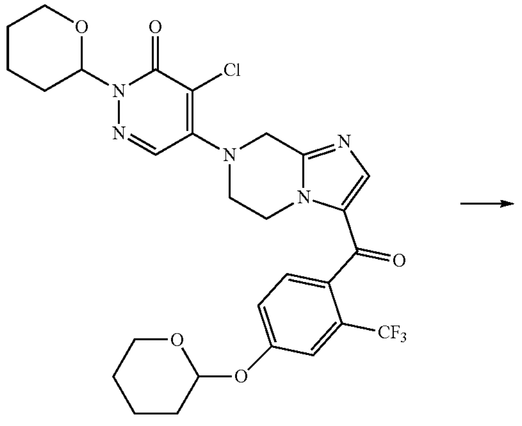

L021-05

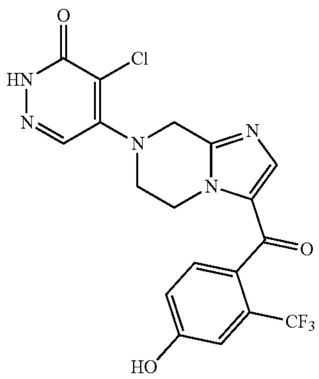

L021

21.1 Preparation of Compound L021-01

Compound L020-a (2 g, 8.3 mmol), 3,4-2H-dihydropyran (1.4 g, 16.6 mmol), pyridinium p-toluenesulfonate (41.6 mg, 0.83 mmol) and dichloromethane (20 mL) were added to a reaction flask in turn, and the mixture was stirred for dissolution, and then the obtained reaction solution was stirred at room temperature for 4 hours. The reaction solution was concentrated under reduced pressure, and the crude product was purified by rapid preparative chromatography (6% ethyl acetate in petroleum ether) to obtain 2.7 g of compound L021-01.

$^{1}$H NMR (400 MHz, $CDCl_3$) § 10.48-10.37 (m, 3H), 10.17-10.10 (m, 2H), 10.07-10.00 (m, $^{1}$H), 8.41-8.36 (m, $^{1}$H), 8.20-8.14 (m, $^{1}$H), 6.58 (t, J=3.0 Hz, $^{1}$H), 4.92 (dd, $J_1$=8.8, $J_2$=3.2 Hz, $^{1}$H), 4.63 (d, J=3.2 Hz, $^{1}$H), 4.44 (d, J=8.8 Hz, $^{1}$H).

21.2 Preparation of Compound L021-02

The compound L021-02 was prepared referred to the preparation method of compound L020-02, and the raw material in step 20.2 was changed from compound L020-01 to compound L021-01. 660 mg of compound L021-02 was obtained. LC-MS $[M+H]^+$=394.10.

21.3 Preparation of Compound L021-03

The compound L021-03 was prepared referred to the preparation method of compound L020-03, and the raw material in step 20.3 was changed from compound L020-02 to compound L021-02. 500 mg of compound L021-03 was obtained as a crude product.

21.4 Preparation of Compound L021-04

The compound L021-04 was prepared referred to the preparation method of compound L020-04, and the raw material in step 20.4 was changed from compound L020-03 to compound L021-03. 380 mg of compound L021-04 was obtained. LC-MS $[M+H]^+$=610.15.

21.5 Preparation of Compound L021-05

Compound L021-04 (300 mg, 0.49 mmol) was dissolved in dichloromethane (10 mL), and sodium bicarbonate (50 mg, 0.59 mmol) and sodium bromide (2.53 mg, 0.024 mmol) were added in turn, and then the reaction solution was cooled to 0° C. Then 2,2,6,6-tetramethylpiperidine-nitrogen oxide (0.7 mg, 0.005 mmol) and sodium hypochlorite (366 mg, 0.49 mmol, purity of 10%) were added thereto, and the reaction solution was stirred overnight at room temperature. After the reaction was completed, the reaction solution was slowly poured into sodium bicarbonate aqueous solution (50 mL), and extracted with ethyl acetate (30 mL*2). The combined organic phases were washed with saturated brine, dried over anhydrous sodium sulfate, and filtered, and the filtrate was evaporated to dryness by rotary evaporation. The residue was purified by rapid preparative chromatography (80-100% ethyl acetate in petroleum ether) to obtain 150 mg of compound L021-05. LC-MS $[M+H]^+$=608.20.

21.6 Preparation of Compound 4-chloro-5-(3-(4-hydroxy-2-(trifluoromethyl)benzoyl)-5,6-dihydro-imidazo[1,2-a]pyrazin-7(8H)-yl)pyridazin-3(2H)-one (L021)

L021-05 (150 mg, 0.34 mmol) was placed in a single necked flask, and a solution of hydrogen chloride in 1,4- dioxane (3 mL, 4 M) was added to the reaction, and the reaction solution was stirred for 2 hours at room temperature. After the reaction was completed, the reaction solution was evaporated to dryness by rotary evaporation at low temperature, then slowly poured into sodium bicarbonate aqueous solution (20 mL), extracted with ethyl acetate (10 mL*2), and the combined organic phases were washed with saturated brine, dried over anhydrous sodium sulfate, and filtered, and the filtrate was evaporated to dryness by rotary evaporation. The residue was purified by preparative HPLC to obtain 37.5 mg of compound L021.

LC-MS $[M+H]^+$=440.05;

$^1$H NMR (400 MHz, DMSO-$d_6$): δ 8.01 (s, $^1$H), 7.55 (d, J=8.4 Hz, $^1$H), 7.30 (s, $^1$H), 7.19 (d, J=2.4 Hz, $^1$H), 7.10 (dd, $J_1$=8.4, $J_2$=2.4 Hz, $^1$H), 4.81 (s, 2H), 4.49 (t, J=5.2 Hz, 2H), 3.90 (t, J=5.2 Hz, 2H).

Example 22 Preparation of Compound 4-chloro-5-(3-(4-(dimethylamino)-(trifluoromethyl)benzoyl)-5,6-dihydroimidazo[1,2-a]pyrazin-7(8H)-yl)pyridazin-3(2H)-one (L022)

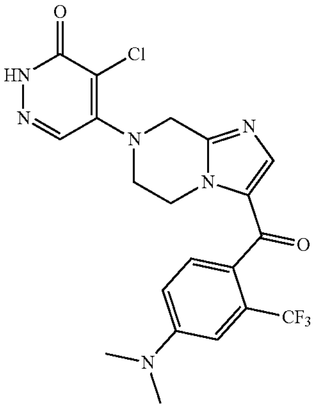

L022

-continued

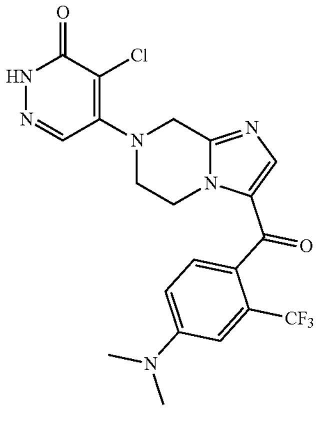

L022

Compound L015 (200 mg, 453 μmol), dimethylamine hydrochloride (110 mg, 1.36 mmol), and potassium carbonate (250 mg, 1.81 mmol) were added to N,N-dimethylformamide (3.0 mL) in turn, and the reaction was stirred at 100° C. for 2 hours. The reaction solution was cooled to room temperature, and added with ethyl acetate (10 mL), then washed for 2 times (20 mL*2) with saturated sodium chloride aqueous solution, dried over anhydrous sodium sulfate, filtered, and the filtrate was concentrated under reduced pressure. The residue was purified by thin-layer chromatography silica gel plate, and then the obtained crude product was purified by preparative HPLC (pure water system) and lyophilized to obtain compound L022 (68.7 mg).

LC-MS $[M+H]^+$=467.1;

$^1$H NMR (400 MHz, DMSO-$d_6$): 13.04 (s, $^1$H), 8.01 (s, $^1$H), 7.55 (d, J=8.8 Hz, $^1$H), 7.28 (s, $^1$H), 7.01 (d, J=2.4 Hz, $^1$H), 6.94 (dd, J=8.8, 2.4 Hz, $^1$H), 4.48 (t, J=5.2 Hz, 2H), 3.89 (t, J=5.2 Hz, 2H), 3.32 (s, 2H), 3.05 (s, 6H).

Example 23 Preparation of Compound 4-chloro-5-(3-((4-fluoro-2-(trifluoromethyl)phenyl)thio)-5,6-dihydroimidazo[1,2-a]pyrazin-7(8H)-yl)pyridazin-3(2H)-one (L023)

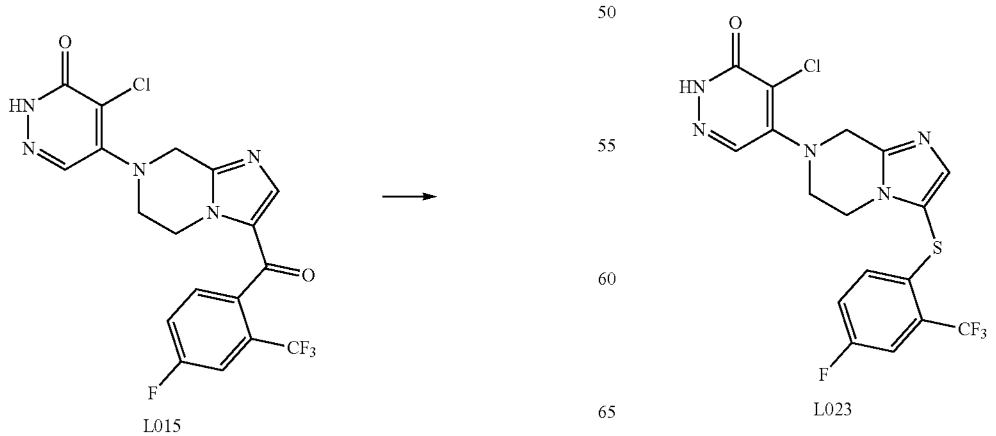

L015

L023

-continued

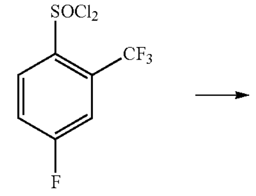

L023-a

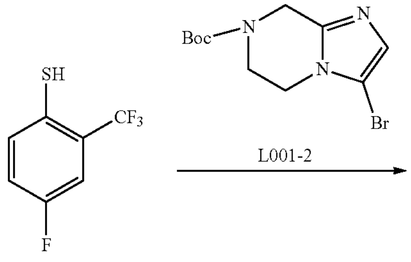

L023-01

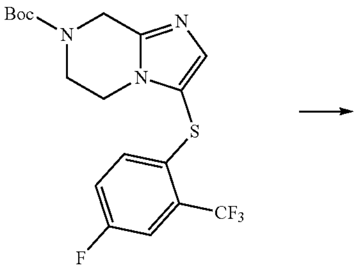

L023-02

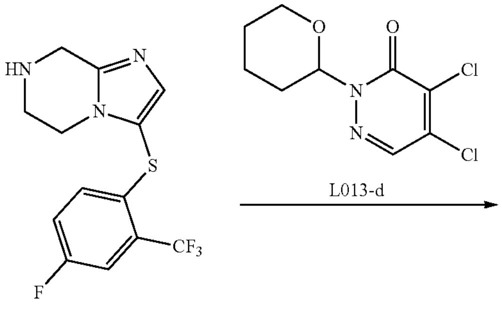

L023-03

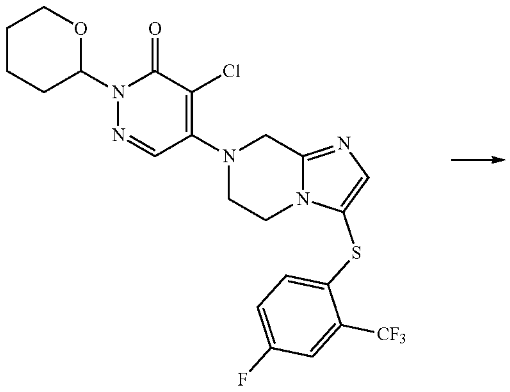

L023-04

-continued

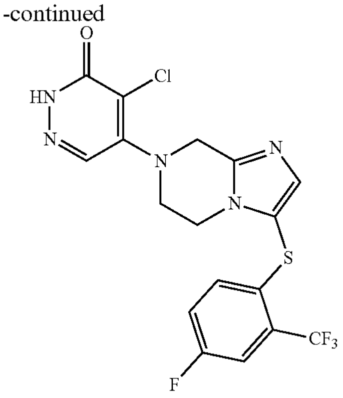

L023

23.1 Preparation of Compound L023-01

L023-a (1 g, 3.55 mmol) and triphenylphosphine (2.8 g, 10.64 mmol) were dissolved in tetrahydrofuran (15 mL), and the reaction solution was stirred at room temperature for 16 hours. After the reaction was completed, the reaction solution was quenched with water (200 mL), extracted with ethyl acetate (200 mL*3), and the organic phases were combined, washed with saturated brine (50 mL), and dried over anhydrous sodium sulfate, and then filtered, and the filtrate was concentrated under reduced pressure and the crude product was purified by silica gel column chromatography (petroleum ether/ethyl acetate=5/1) to obtain 450 mg of compound L023-01.

$^1$H NMR (400 MHz, DMSO-$d_6$) δ 7.85 (dd, $J_1$=8 Hz, $J_2$=4 Hz, $^1$H), 7.74 (dd, $J_1$=12 Hz, $J_2$=4 Hz, $^1$H), 7.64 (td, $J_1$=8 Hz, $J_2$=4 Hz, $^1$H).

23.2 Preparation of Compound L023-02

Compound L023-01 (400 mg, 2.02 mmol), L001-2 (2.8 g, 10.64 mmol), tris(dibenzylideneacetone) dipalladium (186 mg, 0.21 mmol), 2-dicyclohexylphosphino-2',4',6'-triisopropylbiphenyl (190 mg, 0.41 mmol) and cesium carbonate (1.33 g, 4.04 mmol) were dissolved in diethylene glycol dimethyl ether (5 mL), and the system was replaced with nitrogen for three times, and then the mixture was reacted at 140° C. for 5 hours, then the reaction was completed. The reaction solution was quenched with water (50 mL), extracted with ethyl acetate (50 mL*3), and the organic phases were combined, washed with saturated brine (50 mL), dried over anhydrous sodium sulfate, filtered, and the filtrate was concentrated under reduced pressure. The crude product was purified by silica gel chromatography column (petroleum ether/ethyl acetate=1/1) and than further purified by preparative high-performance liquid chromatography to obtain 40 mg of compound L023-02. LC-MS $[M+H]^+$=418.05.

23.3 Preparation of Compound L023-03

Compound L023-02 (40 mg, 0.10 mmol) was dissolved in a solution of 4M hydrogen chloride in 1,4-dioxane (2 mL). Then palladium/carbon (10%, 60 mg) was added thereto, and the reaction mixture was stirred and reacted at room temperature for 2 hours, and the reaction was completed. The reaction solution was concentrated to obtain 35 mg of compound L023-03.

LC-MS $[M+H]^+$=318.05.

23.4 Preparation of Compound L023-04

Compound L023-03 (30 mg, 0.094 mmol), L013-d (41 mg, 0.11 mmol) and N,N-diisopropylethylamine (61 mg, 0.47 mol) were dissolved in dimethyl sulfoxide (1 mL), and the reaction mixture was heated to 60° C. and reacted for 2 hours, and the reaction was completed. The reaction solution was quenched with 20 mL of water, extracted with ethyl acetate (30 mL*3), and the organic phases were combined, washed with saturated brine (50 mL), and dried over anhydrous sodium sulfate, and then filtered, and the filtrate was concentrated under reduced pressure to obtain 40 mg of compound L023-04 as a crude product.

23.5 Preparation of Compound 4-chloro-5-(3-((4-fluoro-2-(trifluoromethyl)phenyl)thio)-5,6-dihydroimidazo[1,2-a]pyrazin-7(8H)-yl)pyridazin-3(2H)-one (L023)

Compound L023-04 (35 mg, 0.07 mmol) was dissolved in a solution of 4M hydrogen chloride in 1,4-dioxane (2 mL). The reaction solution was reacted at room temperature for 2 hours, and the reaction was completed. The reaction solution was concentrated, and the residue was purified by preparative high-performance liquid chromatography to obtain 6 mg of compound L023.

LC-MS $[M+H]^+$=445.00.

$^{1}H$ NMR (400 MHz, DMSO-$d_6$) δ 13.01 (s, $^{1}H$), 7.93 (s, $^{1}H$), 7.70 (dd, J=9.0, 2.8 Hz, $^{1}H$), 7.49 (s, $^{1}H$), 7.44 (td, J=8.5, 2.8 Hz, $^{1}H$), 6.95 (dd, J=8.9, 5.1 Hz, $^{1}H$), 4.71 (s, 2H), 3.89-3.75 (m, 4H).

Example 24 Preparation of Compound 4-chloro-5-(3-((4-fluoro-2-(trifluoromethyl)phenyl)sulfinyl)-5,6-dihydroimidazo[1,2-a]pyrazin-7(8H)-yl)pyridazin-3(2H)-one (L024)

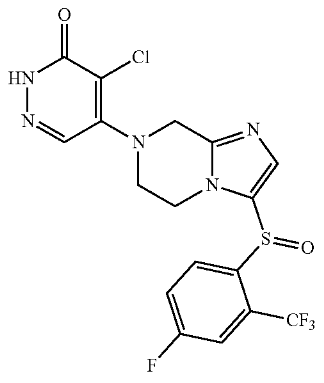

L024

-continued

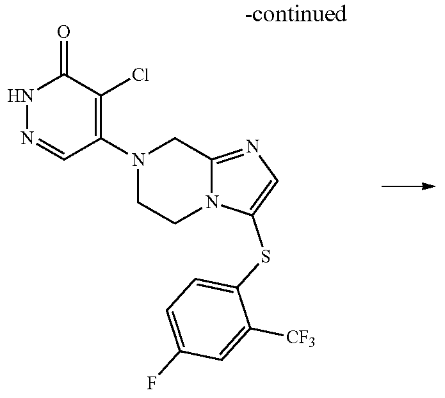

L023

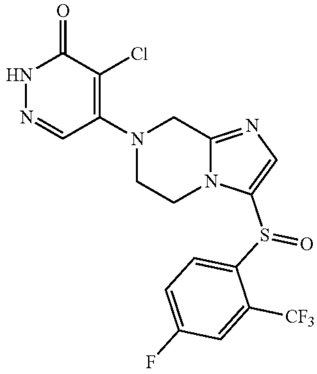

L024

Compound L023 (18 mg, 0.04 mmol) was dissolved in acetic acid: hydrogen peroxide=1:1 (4 mL), and the reaction solution was stirred at room temperature for 36 hours. After the reaction was completed, the reaction solution was quenched with sodium sulfite (10 mL), then the pH of the mixture was adjusted to 8 with sodium bicarbonate, and the mixture was extracted with ethyl acetate (30 mL*3). The organic phases were combined, washed with saturated brine (50 mL), dried over anhydrous sodium sulfate, and then filtered, and the filtrate was concentrated under reduced pressure, and the residue was purified by preparative high-performance liquid chromatography to obtain 8.3 mg of compound L024.

LC-MS $[M+H]^+$=462.00.

$^{1}H$ NMR (400 MHz, DMSO-$d_6$) δ 13.06 (s, $^{1}H$), 8.42 (dd, $J_1$=8 Hz, $J_2$=4 Hz, $^{1}H$), 7.96-7.92 (m, 2H), 7.15 (d, J=52 Hz, $^{1}H$), 6.93 (d, J=20 Hz, $^{1}H$), 4.73 (s, 2H), 4.37-4.32 (m, $^{1}H$), 4.12-4.06 (m, $^{1}H$), 3.95-3.82 (m, 2H).

Example 25 Preparation of Compound 4-chloro-5-(3-(2-(difluoromethyl)-4-fluorobenzoyl)-5,6-dihydroimidazo[1,2-a]pyrazin-7(8H)-yl)pyridazin-3(2H)-one (L025)

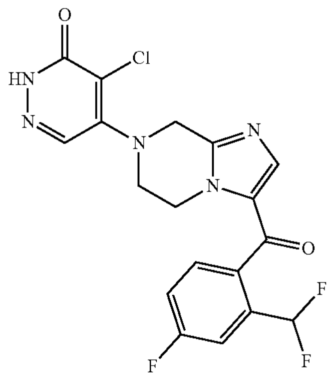

L025

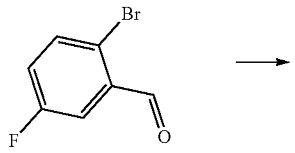

L025-a

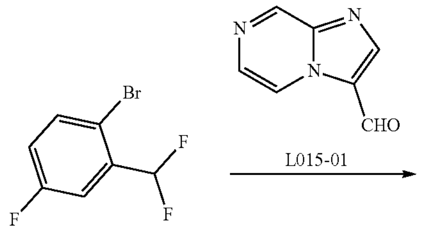

L025-01

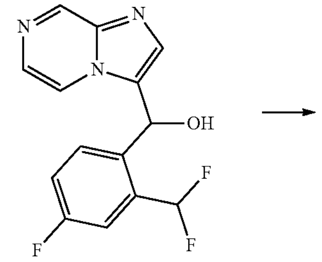

L025-02

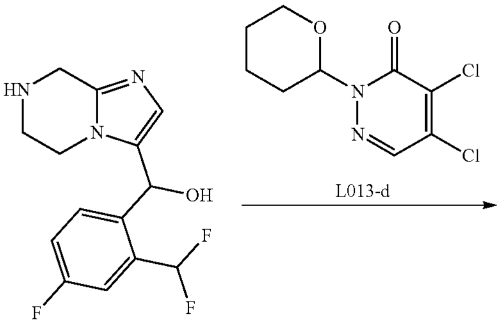

L025-03

-continued

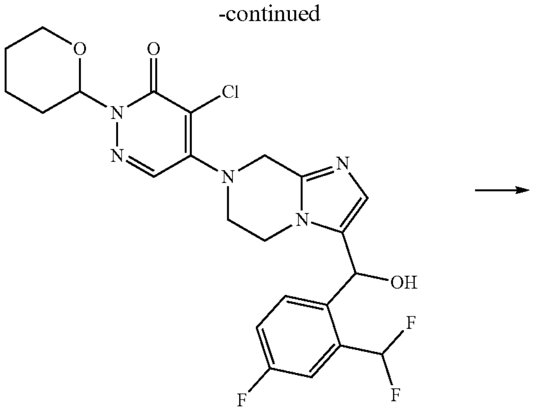

L025-04

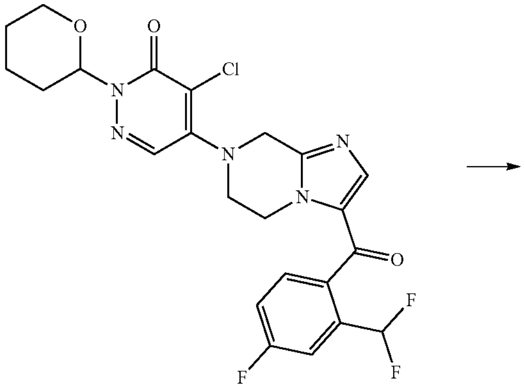

L025-05

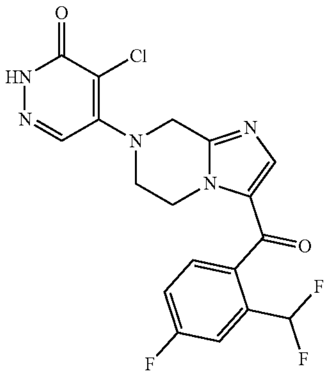

L025

25.1 Preparation of Compound L025-01

Compound L025-a (10.00 g, 49.30 mmol) and diethylamino sulfur trifluoride (15.90 g, 98.30 mmol) were dissolved in dichloromethane (100 mL), and the reaction solution was stirred at −10° C. for 16 hours. After the reaction was completed, the reaction solution was concentrated under reduced pressure to obtain a crude product, and the crude product was purified by silica gel chromatography column (petroleum ether/ethyl acetate=5/1) to obtain 7 g of compound L025-01.

25.2 Preparation of Compound L025-02

Compound L025-01 (2.00 g, 8.89 mmol) was dissolved in anhydrous tetrahydrofuran (20 mL), and the system was replaced with nitrogen for three times, and n-butyllithium (2.5 M, 3.91 mL, 9.78 mmol) was added thereto at −78° C. and the mixture was reacted for 0.5 hours. Then L015-01 (1.44 g, 9.78 mmol) was added to the reaction and the reaction mixture was reacted at −78° C. for 2 hours. After the reaction was completed, the reaction solution was quenched with saturated sodium chloride aqueous solution (20 mL), and then extracted with ethyl acetate (50 mL*3), and the organic phases were combined, and then washed with saturated brine (50 mL), dried over anhydrous sodium sulfate, filtered, then the filtrate was concentrated under reduced pressure, and the crude product was purified by silica gel chromatography column (petroleum ether/ethyl acetate=10/1) to obtain 1.1 g of compound L025-02.

LC-MS $[M+H]^+$=294.05.

25.3 Preparation of Compound L025-03

Compound L025-02 (244 mg, 0.85 mmol) was dissolved in methanol (3 mL). Then platinum dioxide (38.70 mg, 0.17 mmol) was added thereto, and the reaction mixture was reacted at 45° C. for 2 hours under hydrogen atmosphere, and the reaction was completed. The reaction solution was filtered, and the filtrate was concentrated to obtain 300 mg of compound L025-03.

25.4 Preparation of Compound L025-04

Compound L025-03 (300 mg, 1.04 mmol), L013-d (300 mg, 1.30 mmol) and N,N-diisopropylethylamine (250 mg, 2.00 mmol) were dissolved in dimethyl sulfoxide (5 mL), and the reaction solution was heated to 80° C. and reacted for 2 hours, and the reaction was completed. The reaction solution was quenched with water (20 mL), extracted with ethyl acetate (30 mL*3), and the organic phase was combined, washed with saturated brine (50 mL), and dried over anhydrous sodium sulfate, and then filtered and the filtrate was concentrated under reduced pressure, and the crude product was purified by silica gel chromatography column (dichloromethane/methanol=10/1) to obtain of 200 mg of compound L025-04. LC-MS $[M+H]^+$=510.20.

25.5 Preparation of Compound L025-05

Compound L025-04 (200 mg, 0.39 mmol), $H_2O$ (0.5 mL), sodium bicarbonate (49.40 mg, 0.59 mmol) and sodium bromide (2.00 mg, 0.02 mmol) were dissolved in dichloromethane (5 mL), and 2,2,6,6-tetramethylpiperidine oxide (2.00 mg, 0.01 mmol) was added thereto at 0° C., and then sodium hypochlorite (10%, 30 mg, 0.40 mmol) was added dropwise at this temperature. Then the mixture was stirred at 0° C. for 1 hour. After the reaction was completed, the reaction solution was quenched with saturated sodium thiosulfate aqueous solution, extracted with ethyl acetate (30 mL*3), and the organic phase was combined, washed with saturated brine (50 mL), and dried over anhydrous sodium sulfate, and then filtered and the filtrate was concentrated under reduced pressure, and the crude product was purified by silica gel chromatography column (dichloromethane/methanol=10/1) to obtain 110 mg of compound L025-05. LC-MS $[M+H]^+$=508.05.

25.6 Preparation of Compound 4-chloro-5-(3-(2-(difluoromethyl)-4-fluorobenzoyl)-5,6-dihydroimidazo[1,2-a]pyrazin-7(8H)-yl)pyridazin-3(2H)-one (L025)

Compound L025-05 (80 mg, 0.16 mmol) was dissolved in a solution of hydrogen chloride in 1,4-dioxane (3 mL, 4 mol/L), and the mixture was stirred at 25° C. for 1 hour. After the reaction was completed, the mixture was evaporated to dryness by rotary evaporation to remove the solvent to obtain a crude product, and the crude product was purified by preparative high-performance liquid chromatography to obtain 18.1 mg of compound L025.

LC-MS $[M+H]^+$=424.05;

$^1H$ NMR (400 MHz, DMSO-$d_6$) δ13.06 (s, $^1H$), 8.02 (s, $^1H$), 7.78-7.72 (m, $^1H$), 7.61-7.57 (m, 2H), 7.41 (s, $^1H$), 7.04 (t, J=56 Hz, $^1H$), 4.84 (s, 2H), 4.54 (t, J=8 Hz, 2H), 3.92 (t, J=8 Hz, 2H).

Example 26 Preparation of Compound 4-chloro-5-(3-(4-methyl-2-(trifluoromethyl)benzoyl)-5,6-dihydroimidazo[1,2-a]pyrazin-7(8H)-yl)pyridazin-3(2H)-one (L026)

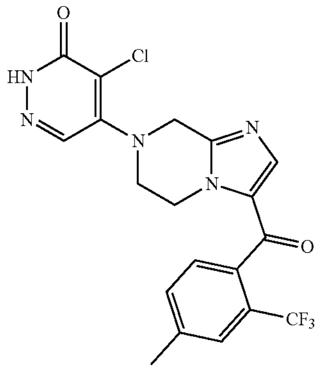

L026

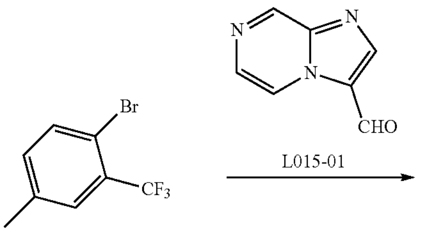

L026-a

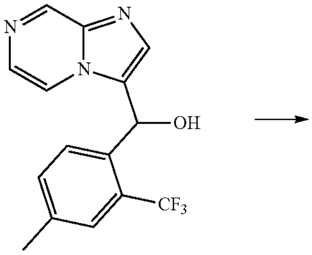

L026-01

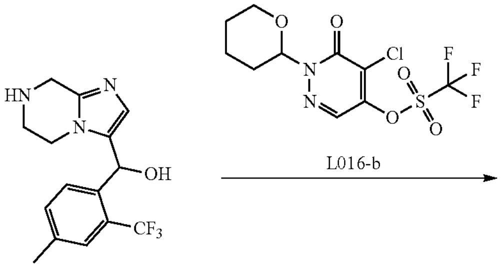

L026-02

-continued

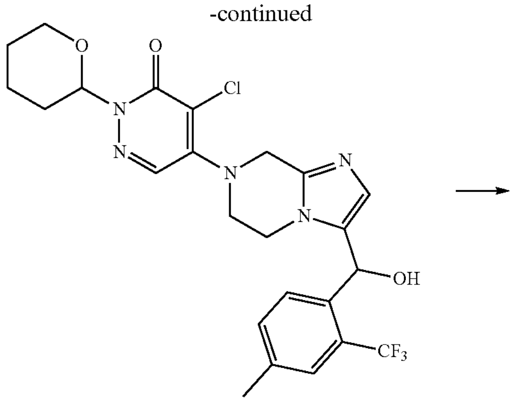

L026-03

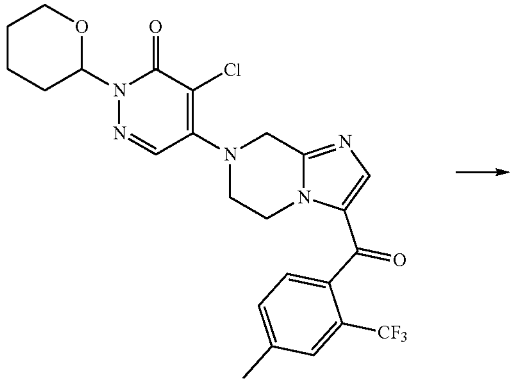

L026-04

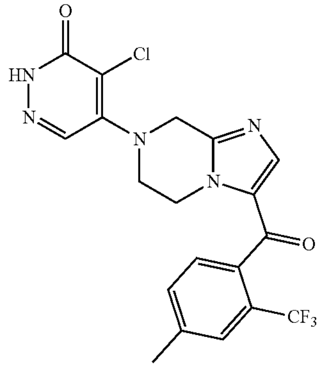

L026

26.1 Preparation of Compound L026-01

The compound L026-01 was prepared referred to the preparation method of compound L025-02, and the raw material in step 25.2 was changed from compound L025-01 to compound L026-a. 130 mg of compound L026-01 was obtained. LC-MS [M+H]$^+$=308.10.

26.2 Preparation of Compound L026-02

The compound L026-02 was prepared referred to the preparation method of compound L025-03, and the raw material in step 25.3 was changed from compound L025-02 to compound L026-01. 100 mg of compound L026-02 was obtained. LC-MS [M+H]$^+$=312.10.

26.3 Preparation of Compound L026-03

The compound L026-03 was prepared referred to the preparation method of compound L025-04, and the raw material in step 25.4 was changed from compound L025-03 to compound L026-02, and changed from compound L013-d to compound L016-b. 110 mg of compound L026-03 was obtained. LC-MS [M+H]$^+$=524.15.

26.4 Preparation of Compound L026-04

L026-03 (100 mg, 0.19 mmol) was dissolved in dichloromethane (4 mL), and Dess-Martin periodinane (122 mg, 0.29 mmol) was added thereto in batches at 0° C. and the mixture was raised to room temperature and reacted for 30 minutes. The reaction solution was added with saturated sodium thiosulfate aqueous solution (30 mL), extracted with dichloromethane (30 mL*3), and the organic phase was combined, washed with saturated brine, and dried over anhydrous sodium sulfate, and then filtered, and the filtrate was concentrated under reduced pressure to obtain a crude product. The crude product was purified by thin-layer chromatography silica gel plate (DCM/MeOH=25/1) to obtain 80 mg of compound L026-04. LC-MS [M+H]$^+$=522.15.

26.5 Preparation of Compound 4-chloro-5-(3-(4-methy-2-(trifluoromethyl)benzoyl)-5,6-dihydroimidazo[1,2-a]pyrazin-7(8H)-yl)pyridazin-3(2H)-one (L026)

The compound L026 was prepared referred to the preparation method of compound L025, and the raw material in step 25.6 was changed from compound L025-05 to compound L026-04. 15.4 mg of compound L026 was obtained.

LC-MS [M+H]$^+$=438.05;

$^1$H NMR (400 MHz, DMSO-$d_6$) § 13.05 (s, $^1$H), 8.00 (s, $^1$H), 7.72 (s, $^1$H), 7.68-7.62 (m, 2H), 7.30 (s, $^1$H), 4.81 (s, 2H), 4.54 (t, J=5.2 Hz, 2H), 3.90 (t, J=5.3 Hz, 2H), 2.35 (s, 3H).

Example 27 Preparation of Compound 5-(3-(2,4-bis(trifluoromethyl)benzyl)-5,6-dihydroimidazo[1,2-a]pyrazin-7(8H)-yl)-4-chloropyridazin-3(2H)-one (L027)

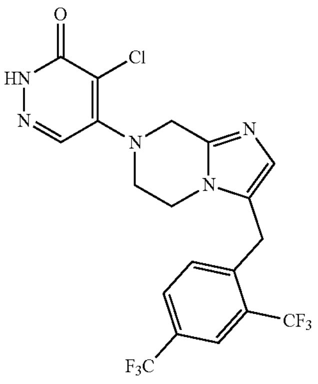

L027

-continued

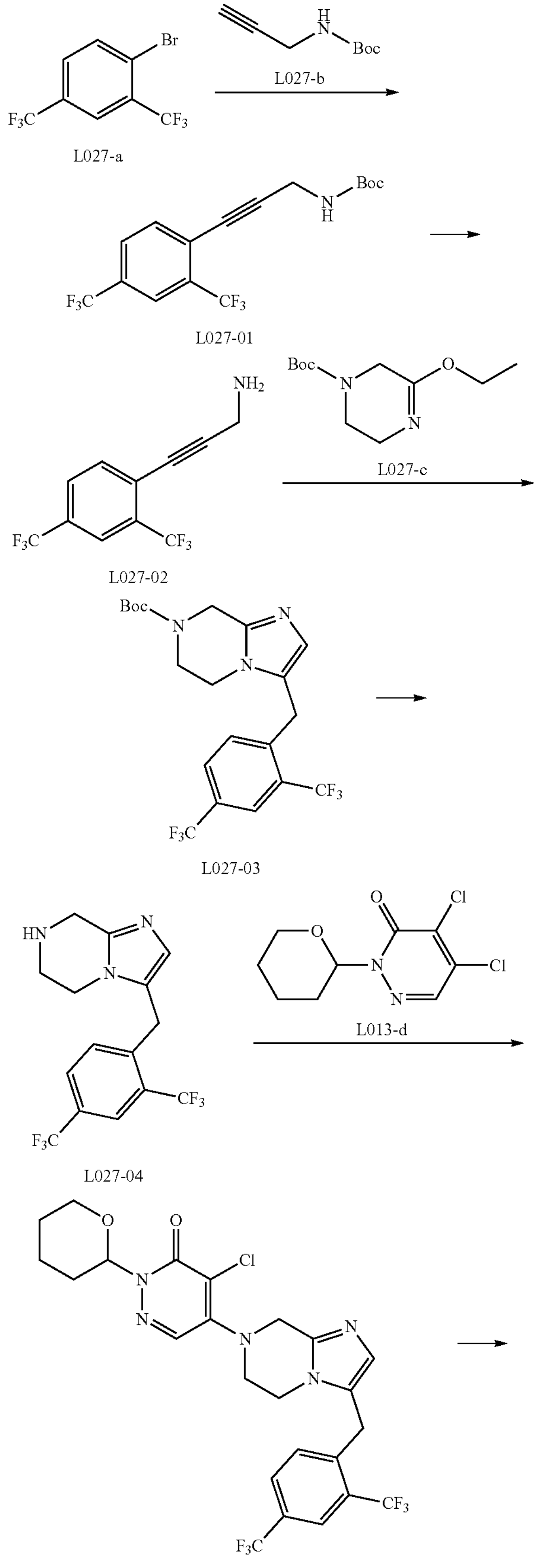

-continued

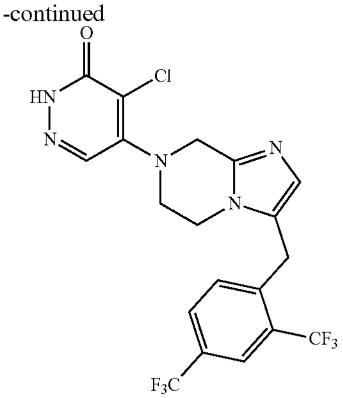

L027

27.1 Preparation of Compound L027-01

The compound L027-01 was prepared referred to the preparation method of compound L006-2, and the raw material in step 6.2 was changed from compound 2-bromo-5-fluorotrifluorotoluene to compound L027-a, and then the catalyst was changed from bis(triphenylphosphine) palladium chloride to Pd(dppf)$Cl_2$. 2.42 g of compound L027-01 was obtained.

$^{1}$H NMR (400 MHz, DMSO-$d_6$) 8.05 (d, J=8.0 Hz, 2H), 7.87 (d, J=8.0 Hz, $^{1}$H), 7.42 (t, J=5.2 Hz, $^{1}$H), 4.04 (d, J=5.6 Hz, 2H), 1.40 (s, 9H).

27.2 Preparation of Compound L027-02

The compound L027-02 was prepared referred to the preparation method of compound L006-3, and the raw material in step 6.3 was changed from compound tert-butyl 3-(4-fluoro-2-(trifluoromethyl)phenyl) prop-2-yn-1-yl) carbamate to compound L027-01. 80.0 mg of compound L027-02 was obtained.

LC-MS $[M+H]^+$=268.00.

27.3 Preparation of Compound L027-03

The compound L027-03 was prepared referred to the preparation method of compound L006-4, and the raw material in step 6.4 was changed from compound tert-butyl 3-(4-fluoro-2-(trifluoromethyl)phenyl) prop-2-yn-1-yl) carbamate to compound L027-02, and changed from compound tert-butyl 5-methoxy-2,3,6,7-tetrahydro-$^{1}$H-1,4-diazepine-1-carboxylate to compound L027-c. 60.0 mg of compound L027-03 was obtained.

LC-MS $[M+H]^+$=450.1.

27.4 Preparation of Compound L027-04

The compound L027-04 was prepared referred to the preparation method of compound L006-5, and the raw material in step 6.5 was changed from compound tert-butyl 3-(4-fluoro-2-(trifluoromethyl)benzyl)-5,6,8,9-tetrahydro-7H-imidazo[1,2-d][1,4]diazepine-7-carboxylate to compound L027-03. 45.0 mg of compound L027-04 was obtained. LC-MS $[M+H]^+$=350.0.

27.5 Preparation of Compound L027-05

The compound L027-05 was prepared referred to the preparation method of compound L006-6, and the raw material in step 6.6 was changed from compound tert-butyl 3-(4-fluoro-2-(trifluoromethyl)benzyl)-5,6,8,9-tetrahydro-7H-imidazo[1,2-d][1,4]diazepine-7-carboxylate to compound L027-03. 40 mg of compound L027-05 was obtained. LC-MS $[M+H]^+$=562.10.

27.6 Preparation of Compound 5-(3-(2,4-bis(trifluoromethyl)benzyl)-5,6-dihydroimidazo[1,2-a]pyrazin-7(8H)-yl)-4-chloropyridazin-3(2H)-one (L027)

The compound L027 was prepared referred to the preparation method of compound L006, and the raw material in step 6.7 was changed from compound 4-chloro-5-(3-(4-fluoro-2-(trifluoromethyl)benzyl)-5,6,8,9-tetrahydro-7H-imidazo[1,2-d][1,4]diazepin-7-yl)-2-(tetrahydro-2H-pyran-2-yl)pyridazin-3(2H)-one to compound L027-05. LC-MS $[M+H]^+$=478.00.

$^1$H NMR (400 MHz, DMSO-$d_6$): 13.03 (s, $^1$H), 8.03 (d, J=8.8 Hz, 2H), 7.95 (s, $^1$H), 7.49 (d, J=8.0 Hz, $^1$H), 6.56 (s, $^1$H), 4.65 (s, 2H), 4.22 (s, 2H), 3.91 (t, J=5.2 Hz, 2H), 3.82 (t, J=5.2 Hz, 2H).

Example 28 Preparation of Compound 4-chloro-5-(3-(4-fluoro-2-(trifluoromethyl) phenoxy)-5,6-dihydroimidazo[1,2-a]pyrazin-7(8H)-yl)pyridazin-3(2H)-one (L028)

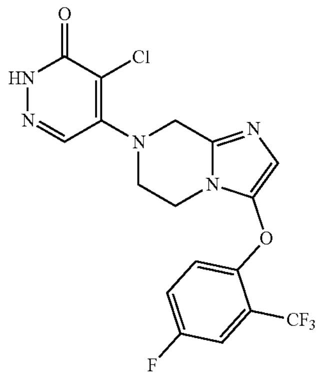

L028

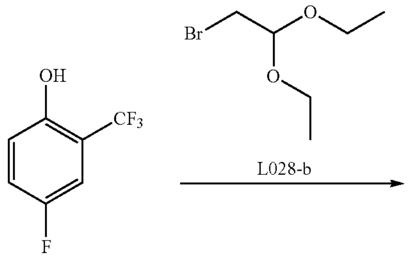

L028-b

L028-a

-continued

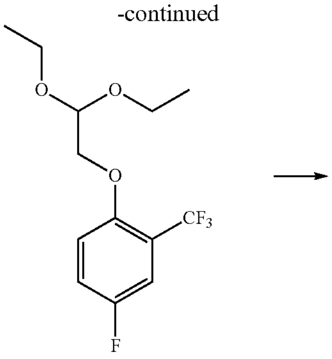

L028-01

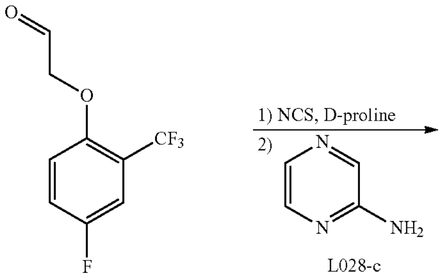

L028-c

L028-02

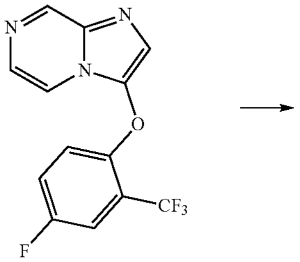

L028-03

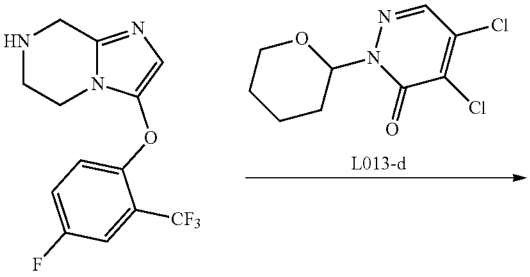

L013-d

L028-04

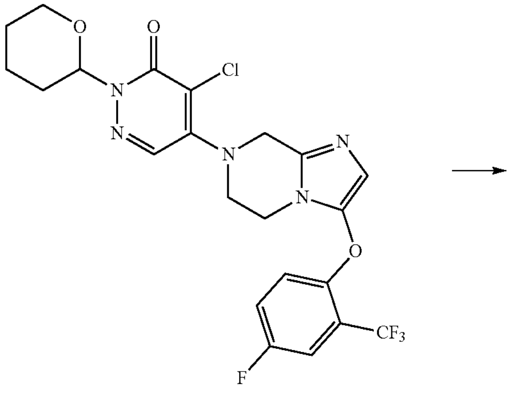

L028-05

-continued

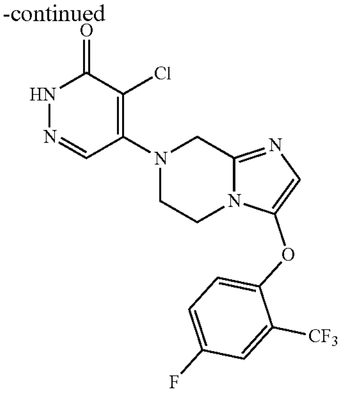

L028

28.1 Preparation of Compound L028-01

Compound L028-a (2.2 g, 12.15 mmol) was dissolved in DMF (25 mL), and L028-b (2.63 g, 13.36 mmol) and potassium carbonate (3.36 g, 24.29 mmol) were added thereto. The mixture was stirred at 70° C. for 2 hours under the protection of nitrogen, and after the reaction was completed, water (50 mL) was added thereto, and the resulting mixture was extracted with ethyl acetate (20 mL*2). The organic phase was washed with saturated brine (20 mL*2), dried over anhydrous sodium sulfate, and the crude product was separated by silica gel column chromatography (petroleum ether/ethyl acetate=10/1) to obtain 2.5 g of compound L028-01.

$^1$H NMR (300 MHz, $CDCl_3$) δ 7.28 (dd, J=8, 7, 3.0 Hz, $^1$H), 7.21-7.14 (m, $^1$H), 6.96 (dd, J=9.0, 3.9 Hz, $^1$H), 4.83 (t, J=5.4 Hz, $^1$H), 4.04 (d, J=5.1 Hz, 2H), 3.84-3.74 (m, 2H), 3.70-3.60 (m, 2H), 1.24 (t, J=7.2 Hz, 6H).

28.2 Preparation of Compound L028-02

Compound L028-01 (2.5 g, 8.41 mmol) was dissolved in THF (5 mL), then concentrated hydrochloric acid (12.06 mol/L, 5 mL) was added dropwise, and the mixture was stirred at 25° C. for 1 hour. After the reaction was completed, the pH of the mixture was adjusted to about 8 with sodium carbonate solution (20 mL), and the mixture was extracted with dichloromethane (20 mL*3). The organic phase was washed with saturated brine (10 mL*2), dried over anhydrous sodium sulfate and concentrated, and then the crude product was separated by silica gel column chromatography (petroleum ether/ethyl acetate=5/1) to obtain 1.5 g of compound L028-02. 1H NMR (300 MHz, $CDCl_3$) δ 9.86 (s, $^1$H), 7.35 (dd, J=8.1, 3.0 Hz, $^1$H), 7.22-7.17 (m, $^1$H), 6.84 (dd, J=9.0, 3.9 Hz, $^1$H), 4.62 (d, J=0.9 Hz, 2H).

28.3 Preparation of Compound L028-03

Compound L028-02 (600 mg, 2.68 mmol) was dissolved in chloroform (6 mL), then D-proline (62 mg, 0.54 mmol) and N-chlorosuccinimide (359 mg, 2.69 mmol) were added thereto, and the mixture was stirred at 0° C. for 30 minutes under the protection of nitrogen, then the reaction solution was raised to room temperature and stirred for 2 hours. Aminopyrazine (256 mg, 2.69 mmol) was added thereto, the mixture was continued to stir at room temperature for 1 hour, and then evaporated to dryness by rotary evaporation to remove the solvent. n-Butanol (4 mL) was added, and the mixture was stirred at 100° C. for 2 hours under the protection of nitrogen. After the reaction was completed, the reaction solution was concentrated, and the crude product was separated by silica gel column chromatography (dichloromethane/ethyl acetate=2/1) to obtain 180 mg of compound L028-03. LC-MS $[M+H]^+$=298.1.

28.4 Preparation of Compound L028-04

Compound L028-03 (180 mg, 0.60 mmol) was dissolved in THF (3 mL), and Pd/C (10%, 32 mg, 0.30 mmol) was added thereto. The mixture was stirred at 25° C. for 9 hours under hydrogen atmosphere. After the reaction was completed, the mixture was filtered through diatomite, and the filtrate was concentrated to obtain 180 mg of compound L028-04.

LC-MS $[M+H]^+$=301.8.

28.5 Preparation of Compound L028-05

Compound L028-04 (180 mg, 0.59 mmol) was dissolved in n-butanol (1.0 mL), then N,N-diisopropylethylamine (231 mg, 1.78 mmol) and compound L013-d (223 mg, 0.89 mmol) were added thereto. The reaction mixture was stirred at 120° C. for 3 hours under the protection of nitrogen. After the reaction was completed, the mixture was concentrated, and the crude product was separated by thin-layer chromatography silica gel plate (petroleum ether/ethyl acetate=1/1) to obtain 90 mg of compound L028-05. LC-MS $[M+H]^+$ =514.2.

28.6 Preparation of Compound 4-chloro-5-(3-(4-fluoro-2-(trifluoromethyl) phenoxy)-5,6-dihydroimidazo[1,2-a]pyrazin-7(8H)-yl)pyridazin-3(2H)-one (L028)

Compound L028-05 (90 mg, 0.17 mmol) was dissolved in dichloromethane (2 mL), and a solution of hydrogen chloride in 1,4-dioxane (4 mmol/L, 2 mL) was added thereto. The mixture was stirred at 25° C. for 1 hour. After the reaction was completed, the mixture was concentrated to obtain 75.7 mg of compound L028.

LC-MS $[M+H]^+$=430.1.

$^1$H NMR (400 MHz, DMSO-$d_6$) δ 13.11 (s, $^1$H), 8.01 (s, $^1$H), 7.83 (dd, J=8.0, 3.2 Hz, $^1$H), 7.71-7.65 (m, $^1$H), 7.52 (dd, J=9.2, 4.4 Hz, $^1$H), 7.42 (s, $^1$H), 4.94 (s, 2H), 4.05 (t, J=4.8 Hz, 2H), 3.94 (t, J=5.2 Hz, 2H).

Example 29 Preparation of Compound 4-chloro-5-(3-(5-fluoro-2-(trifluoromethyl) phenoxy)-5,6-dihydroimidazo[1,2-a]pyrazin-7(8H)-yl)pyridazin-3(2H)-one (L029)

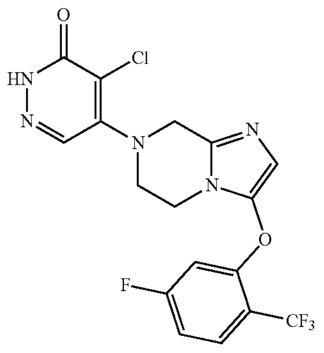

L029

-continued

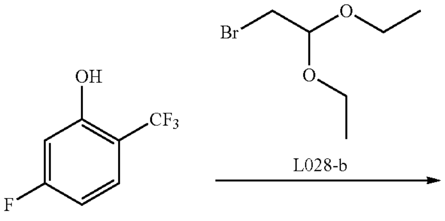

L029-a

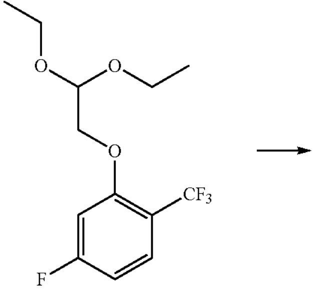

L029-01

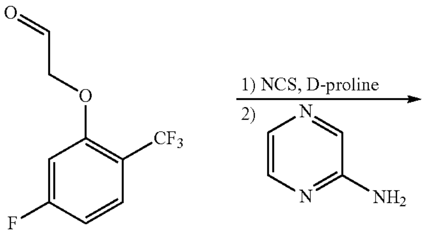

L029-02

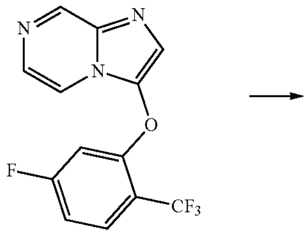

L029-03

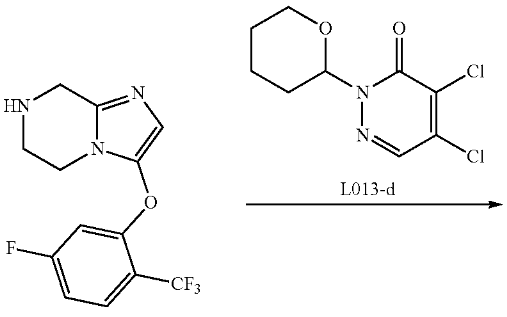

L029-04

-continued

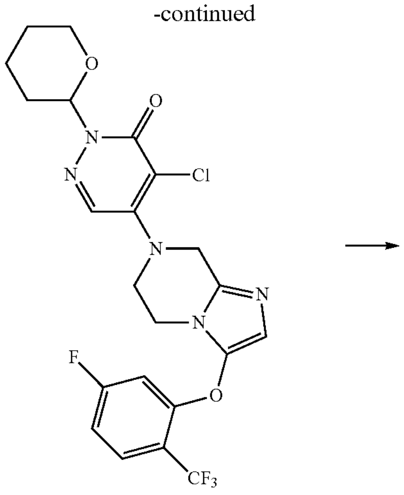

L029-05

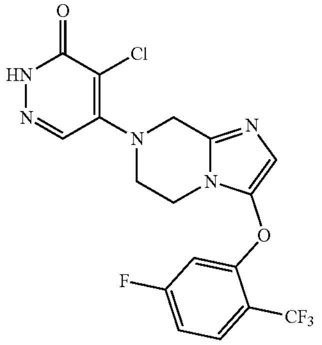

L029

29.1 Preparation of Compound L029-01

The compound L029-01 was prepared referred to the preparation method of compound L028-01, and the raw material in step 28.1 was changed from compound L028-a to compound L029-a to obtain 1.2 g of compound L029-01.

$^1$H NMR (300 MHz, DMSO-$d_6$) 7.69 (dd, J=8.5, 6.6 Hz, $^1$H), 7.28 (d, J=11.2 Hz, $^1$H), 6.95 (s, $^1$H), 4.82 (t, J=5.3 Hz, $^1$H), 4.11 (d, J=5.4 Hz, 2H), 3.64 (dddd, J=16.5, 14.1, 7.1, 2.4 Hz, 4H), 1.13 (t, J=7.0 Hz, 6H).

29.2 Preparation of Compound L029-02

The compound L029-02 was prepared referred to the preparation method of compound L028-02, and the raw material in step 28.2 was changed from compound L028-01 to compound L029-01 to obtain 1.2 g of compound L029-02 as a crude product, which was directly used in the next step without purification.

29.3 Preparation of Compound L029-03

The compound L029-03 was prepared referred to the preparation method of compound L028-03, and the raw material in step 28.3 was changed from compound L028-02 to compound L029-02 to obtain 200 mg of compound L029-03. LC-MS $[M+H]^+$=297.8.

29.4 Preparation of Compound L029-04

The compound L029-04 was prepared referred to the preparation method of compound L028-04, and the raw material in step 28.4 was changed from compound L028-03 to compound L029-03 to obtain 50 mg of compound L029-04. LC-MS $[M+H]^+$=301.8.

29.5 Preparation of Compound L029-05

The compound L029-05 was prepared referred to the preparation method of compound L028-05, and the raw material in step 28.5 was changed from compound L028-04 to compound L029-04 to obtain 40 mg of compound L029-04. LC-MS $[M+H]^+$=513.6;

29.6 Preparation of Compound 4-chloro-5-(3-(5-fluoro-2-(trifluoromethyl) phenoxy)-5,6-dihydroimidazo[1,2-a]pyrazin-7(8H)-yl)pyridazin-3(2H)-one (L029)

The compound L029 was prepared referred to the preparation method of compound L028, and the raw material in step 28.6 was changed from compound L028-05 to compound L029-05 to obtain 12.0 mg of compound L029.

LC-MS $[M+H]^+$=429.6.

$^1H$ NMR (400 MHz, $CD_3OD$): 7.97 (s, $^1H$), 7.80 (dd, J=8.7, 6.0 Hz, $^1H$), 7.10-7.04 (m, $^1H$), 7.01 (dd, J=9.8, 2.1 Hz, $^1H$), 6.77 (s, $^1H$), 4.73 (s, 2H), 3.97 (dd, J=10.6, 4.3 Hz, 4H).

Example 30 Preparation of Compound 4-chloro-5-(3-(2-(trifluoromethyl)benzyl)-5,6-dihydroimidazo[1,5-a]pyrazin-7(8H)-yl)pyridazin-3(2H)-one (L030)

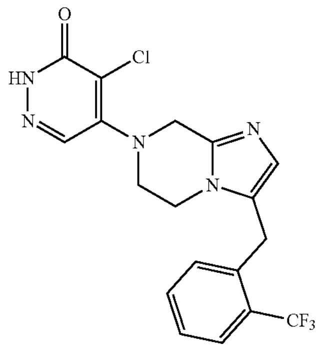

L030

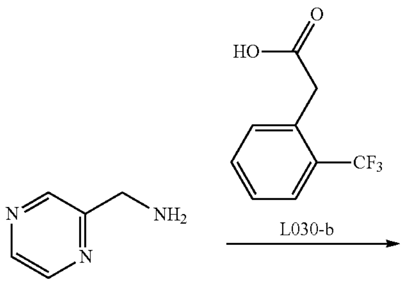

L030-a

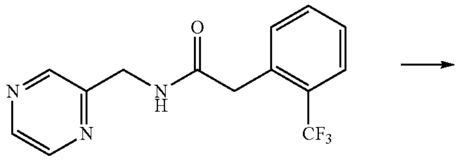

L030-01

-continued

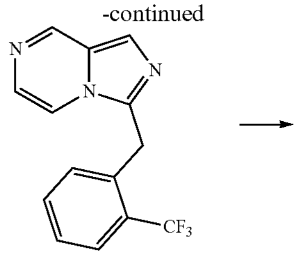

L030-02

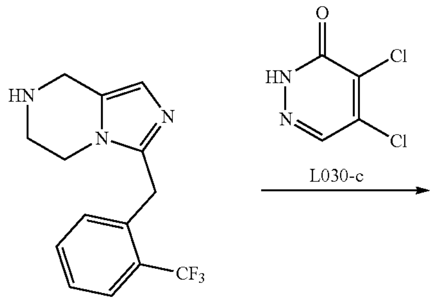

L030-03

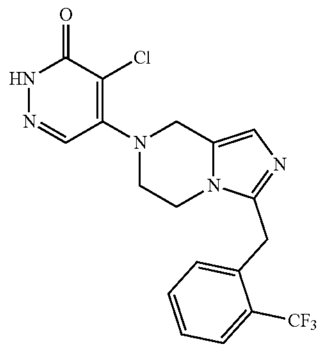

L030

30.1 Preparation of Compound L030-01

Compound L030-a (1.0 g, 9.17 mmol) was weighed into a reaction flask, and then compound L030-b (1.87 g, 9.17 mmol), HATU (5.23 g, 13.7 mmol) and DIPEA (3.55 g, 27.5 mmol) were added to the reaction flask, and then DMF (20 mL) was added to dissolve the above reactants, and the resulting reaction solution was stirred at 50° C. for 2 hours. EtOAc (50 mL) and water (20 mL) were added to the reaction solution, and the mixture was stirred and the phases were separated. The aqueous phase was extracted for 2 times with EtOAc (30 mL), then the combined organic phase was washed with saturated brine, and dried over anhydrous sodium sulfate, filtered, and then the filtrate was concentrated under reduced pressure to obtain a crude product, and the crude product was purified by silica gel column chromatography (PE:EA=4:1 to 2:1) and then concentrated to obtain 2.5 g of compound L030-01.

30.2 Preparation of Compound L030-02

Compound L030-01 (2.4 g, 8.13 mmol) was weighed, and $POCl_3$ (20 mL) was added to dissolve, and the resulting reaction solution was stirred at 90° C. for 2 hours. The reaction solution was cooled to 20° C., and slowly added dropwise to ice water (30 mL), and then EtOAc (50 mL) was added thereto. The pH of the reaction solution was adjusted to 7 to 8 with 0.5 M of NaOH aqueous solution, and the mixture was stirred and the phases were separated. The aqueous phase was extracted for 2 times with EtOAc (50 mL), then the combined organic phases were washed with saturated brine, and dried over anhydrous sodium sulfate, filtered, and then the filtrate was concentrated under reduced pressure to obtain a crude product, and the crude product was purified by silica gel column chromatography (PE: EA=3:1 to 1:1) and then concentrated to obtain 1.1 g of compound L030-02. LC-MS $[M+H]^+$=278.05.

30.3 Preparation of Compound L030-03

Compound L030-02 (500 mg, 1.8 mmol) was weighed, then Pd/C (50 mg, 10%) and MeOH (20 mL) were added, and the mixture was replaced with hydrogen for three times, and stirred at 50° C. for 16 hours under hydrogen atmosphere. The mixture was filtered, and the filter cake was washed with MeOH (10 mL) for 2 times and the filtrate was combined and concentrated at 45° C. under reduced pressure to obtain 440 mg of compound L030-03. LC-MS $[M+H]^+$ =282.10.

30.4 Preparation of Compound 4-chloro-5-(3-(2-(trifluoromethyl)benzyl)-5,6-dihydroimidazo[1,5-a]pyrazin-7(8H)-yl)pyridazin-3(2H)-one (L030)

Compounds L030-03 (440 mg, 1.56 mmol) and L030-c (284 mg, 1.7 mmol) were weighed, and DIPEA (600 mg, 4.7 mmol) and DMF (10 mL) were added thereto, and the reaction solution was stirred at 100° C. for 16 hours. EtOAc (50 mL) and water (20 mL) were added to the reaction solution, and the mixture was stirred and the phases were separated. The aqueous phase was extracted for 2 times with EtOAc (30 mL), then the combined organic phases were washed with saturated brine, and dried over anhydrous sodium sulfate, filtered, and then the filtrate was concentrated under reduced pressure to obtain a crude product, and the crude product was purified by preparative high-performance liquid chromatography in a $H_2O$/acetonitrile system, and the preparation solution was concentrated at 45° C. and lyophilized to obtain 89 mg of compound L030. LC-MS $[M+H]^+$=410.00;

$^1H$ NMR (400 MHz, DMSO-$d_6$) δ 13.13 (s, $^1H$), 7.95 (s, $^1H$), 7.85 (d, J=7.6 Hz, $^1H$), 7.71 (t, J=7.6 Hz, $^1H$), 7.61 (t, J=7.6 Hz, $^1H$), 7.51 (s, $^1H$), 7.32 (d, J=7.6 Hz, $^1H$), 4.79 (s, 2H), 4.56 (s, 2H), 4.24 (t, J=5.4 Hz, 2H), 3.91 (t, J=5.4 Hz, 2H).

Comparative Example

Compounds C001 and C002 were the compounds disclosed in patent WO2019055966A2 as TRPC5 inhibitors.

TABLE 1

| Compound number | Compound structure |
|---|---|
| C001 | 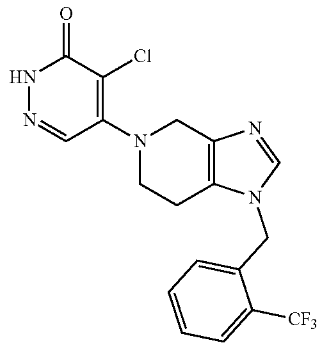 [SMILES: O=c1[nH]ncc(N2CCc3c(ncn3Cc3ccccc3C(F)(F)F)C2)c1Cl] |
| C002 | 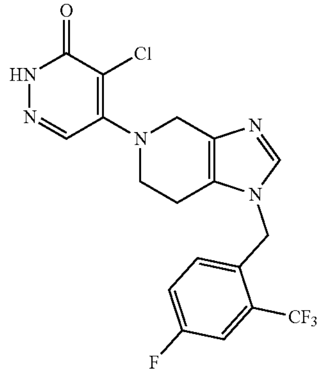 [SMILES: O=c1[nH]ncc(N2CCc3c(ncn3Cc3ccc(F)cc3C(F)(F)F)C2)c1Cl] |

Effect Example 1 Biological Activity Test

TRPC5 was a type of non-selective cation channel with permeability to calcium ions, therefore, TRPC5 agonist Englerin A (EA) and TRPC5 inhibitor Pico145 were used as positive controls in this experiment. The method for detecting intracellular $Ca^{2+}$ in TRPC5-HEK 293 cells by using Fluo-4 AM fluorescent dye to detect compound indirectly reflected the effect of the compound on the TRPC5 channel.

1. Cell Culture 1.1 TRPC5 Resuscitation

Resuscitation fluid: 100% DMEM with high glucose

Selective medium: DMEM with high glucose+10% FBS+1% P/S+1% HEPES+Blasticidin (5 μg/mL)+Hygromycine (50 μg/mL)

Induction medium: DMEM with high glucose+10% FBS+1% P/S+1% HEPES+Doxycycline (1 μg/mL)

Resuscitation process: The TRPC5 was taken out of the liquid nitrogen tank, and transferred from the ice box to the water bath, and then dissolved in a circle to a small piece of ice, the TRPC5 was transferred form the cryopreservation solution to the resuscitation solution, and centrifuged at 1000 rpm for 5 minutes, and then the supernatant was discarded, then transferred to the selective medium, and expanded in a $CO_2$ incubator (5% $CO_2$, 95% humidity, 37° C.).

1.2 TRPC5 Cell Junction Plate

Before 14 hours of the real-time fluorescence experiment, the cells were washed with PBS and digested with TE, and then the cells were diluted to 200,000 cells/mL using induction medium and inoculated to a 96-well black-walled clear bottom plate coated with PDL (10 mg/mL of the mother liquor with a final concentration of 10 μg/mL), 100 μL/well, i.e., 20,000 cells/well.

2. Preparation of Buffer Solution 500 mL of TRPC5 calcium signal detection external solution: 4.0908 g NaCl, 0.1864 g KCl, 0.111 $CaCl_2$), 0.0476 g $MgCl_2$, 0.9 Glucose, 1.1915 HEPES.

Calcium fluorescent dyes: TRPC5 calcium signal detection external solution containing Fluo-4 with a final concentration of 4 μM (containing 0.5% BSA)

3. Compound Preparation

Agonist: Englerin A (EA)

Concentration: Since the $EC_{50}$ of TRPC5 activated by the EA was approximately 0.35 nM, and 0.3 nM of EA was used.

Positive inhibitor: Pico145 (HC608)

Concentration: 100 nM

Test compound

Routine preparation, 8×drug solution, 60 μL per well of V-bottom plate

4. Data Processing

Water reduction well, remove baseline, AUC

The results are shown in Table 2:

TABLE 2

| Compound number | TRPC5 inhibition, $IC_{50}$ (nM) |
|---|---|
| L001 | 10.75 |
| L002 | 6.52 |
| L007 | 7.37 |
| L009 | 39.43 |
| L013 | 14.56 |
| L014 | 18.23 |
| L015 | 11.5 |
| L019 | 24 |

Effect Example 2 Liver Microsome Half-Life Test

The in vitro metabolic stability of the compounds of the present disclosure was determined using warm incubation method of various liver microsomes. A proper amount of test compound was added to the liver microsomal reaction system (1 mg/mL liver microsomal protein, 25 U/mL glucose 6-phosphate dehydrogenase, 1 mM NADP, 6 mM D-6-phosphate glucose, 5 mM $MgCl_2$), and the reaction solution was started by incubation in a water bath at 37° C., then 100 μL of the reaction solution at each time point was added to a centrifuge tube containing 400 μL of internal standard working solution precooled at 0° C. (containing a solution of 200 ng/mL dexamethasone, diclofenac, tolbutamide and labetalol in acetonitrile), then the reaction was stopped, centrifuged at 4° C. for 10 min at 10,000 g, and the supernatant was taken into LC-MS for analysis and detection to obtain in vitro metabolic half-lives of the tested compounds in various liver microsomes.

The results are shown in Table 3:

TABLE 3

| Compound | Liver microsomes $T_{1/2}$ (min) | | | | |
|---|---|---|---|---|---|
| number | Human | Rat | Mouse | Beagle dog | Monkey |
| C001 | 54 | 5 | 60 | 15 | 38 |
| C002 | 90 | 34 | 115 | 102 | 15 |
| L002 | 262 | | 188 | — | — |
| L001 | 173 | 20 | 154 | — | — |
| L013 | 148 | | 131 | — | — |
| L014 | 7589 | — | 167 | — | — |
| L015 | 531 | 174 | 78 | — | 247 |

The data in table 3 show that the metabolic stability of the compounds of the present disclosure in liver microsomes is significantly improved compared with compounds $C_{001}$ and $C_{002}$, indicating that the compounds of the present disclosure have better metabolic stability in liver microsomes and have better clinical pharmacokinetic properties.

Effect Example 3 Pharmacokinetic Study of the Compound of the Present Disclosure in Mice In Vivo SPF mice (SPF (Beijing) Biotechnology Co., Ltd.) were fasted overnight (no control water) after adaptive domestication, and given 3 mg/kg or 1 mg/kg of the compound of the present disclosure by gavage and tail vein injection respectively. Mouse plasma was collected at a specific time point after administration, the concentration of compound in plasma was detected by LC-MS/MS (AB SCIEX Qtrap4500), and the PK parameters of each compound (WinNonlin V5.2, Pharsight) were statistically analyzed and calculated to reflect the pharmacokinetic properties of the compound of the present disclosure in mice in vivo.

According to the above experiment compounds of the present disclosure, the results show that the compounds of the present disclosure have good pharmacokinetic properties in mice in vivo, and can obtain higher in-vivo exposure and higher oral bioavailability at a lower dose, and the oral bioavailability of some compounds is more than 30%, and the oral bioavailability of some compounds is more than 50%. Table 4 shows experimental data for representative compound.

TABLE 4

PK experiments of the compound of the present disclosure in mice in vivo

| Compound | Administered dose mg/kg | Administration mode | $C_{max}$ (ng/mL) | ($AUC_{last}$) (ng/ mL*hr) | Oral bioavailability (%) |
|---|---|---|---|---|---|
| L001 | 1 | p.o. | 84.30 | 84.30 | 80.6 |
| | | i.v. | 225.00 | 225.00 | |
| L002 | 1 | p.o. | 248 | 625 | 43.2 |
| | | i.v. | 833 | 1447 | |
| L014 | 1 | p.o. | 301 | 1066 | 161 |
| | | i.v. | 762 | 663 | |
| L015 | 1 | p.o. | 422 | 1245 | 66.8 |
| | | i.v. | 1110 | 1864 | |

Effect Example 4 Study on the Tissue Distribution of the Compound of the Present Disclosure In CD-1 Mice after Single Intragastric Administration

Experimental Protocol 1.1 Experimental Instruments

TABLE 5

| Name | Model/ specification | Manufacturer |
|---|---|---|
| Electronic analytical balance | MS105DU | Mettler-Toledo |
| Electronic scale | YP2001 | Shanghai youke instrument |
| High speed refrigerated centrifuge | STR16 | Thermo Fisher Scientific |
| Ultrafine homogenizer | F6/10-8G | Shanghai Fluke |

1.2 Experimental Preparation

Mice: CD-1 mice, SPF grade, 9, male, weighting 18-22 g (source: SPF (Beijing) Biotechnology Co., Ltd., certificate number: 110324200103036532).

Feeding conditions: Ordinary animal house feeding, free access to food and water, 3 animals/cage rearing, 12/12 hours light/dark cycle adjustment (7:00 am/7:00 pm), temperature 23±1° C.

Drug preparation: After accurately weighing the compound L015, 20% solutol of the required volume was firstly added, and the mixture was ultrasonicated for 20 minutes, and then stirred for 1.5 hours until no particles were visible to the naked eye. The middle layer of the drug solution was taken for administration. The suspension was taken 2 parts from the top, the middle and the low layer respectively, and then 2 parts were taken in the middle layer for the clarified solution, and each part was accurately drawn from 100 μL to 1.5 mL of EP tube. Samples were taken before administration, and then after sampling, the samples were stored in a −80° C. refrigerator and sent together with the plasma samples for bioanalytical test.

1.3 Dosage Regimen

Animals were randomly divided into 3 groups, compound L015 was administered at 3 different time points, 3 males in each group, all mice were given a single intragastric administration, and the administration volume was 10 mL/kg, the specific grouping and administration are as follows:

| Group | Subject | Number (female/male) | Time point | Solvent | Administration Dose (mg/kg) | Drug Concentration (mg/mL) | Administration volume (mL/kg) | Test substance |
|---|---|---|---|---|---|---|---|---|
| 1 | L015 | 0/3 | 0.167 hours | 20% | 10 | 1.00 | 10 | L015 |
| 2 | L015 | 0/3 | 1 hour | solutol | 10 | 1.00 | 10 | |
| 3 | L015 | 0/3 | 10 hours | | 10 | 1.00 | 10 | |

Note:
(1) Animal certificate number: 110324200103036532, CD-1 mouse, SPF (Beijing) Biotechnology Co., Ltd .; (2) three groups of mice fasted all night before administration with no control water; the food was returned 4 hours after administration; (3) the PK results of 1, 3, 10 mpk mice before were taken as reference: L015, after mice were given 10 mg/kg by intragastric administration, the absorption phase was 0.167 hours, and the plasma concentration of the test substance reached its peak at 1 h; at about 10 hours, it was in the elimination phase.

1.4 Sample Collection and Preparation

After the administration, each group of animals were anesthetized by intraperitoneal injection of 1% pentobarbital sodium (the volume of administration was 0.06 mL/10 g) 5 minutes in advance at their respective time points, and about 0.3 mL of blood was collected in an anticoagulant EP tube (containing 4 μL EDTA-K2, 375 mg/mL), which was slowly turned upside down for 3 times and stored in an ice box (no more than 30 minutes) centrifuged at 4° C. for 10 minutes with 3500×g, the supernatants were transferred to labeled EP tubes for bioanalytical test. If the test could not be done on the same day, the sample should be stored at −80° C. until the test (be careful not to perform multiple freezing/thawing processes).

After the blood was taken, the abdominal cavity was quickly opened, the abdominal aorta and vein of the mice were cut, and after the blood was dried, the heart, liver, spleen, lung, kidney and brain of the mice were taken respectively. After the tissue was taken, the tissue was immediately washed the surface residual blood with normal saline, blotted dry with filter paper, and the connective tissue was removed and weighed. The homogenization tube was placed in an ice water bath, and the tissue sample homogenate was thoroughly homogenized with a high-speed homogenizer and sent for bioanalytical test. If the test could not be done on the same day, the sample should be stored at −80° C. until the test (be careful not to perform multiple thawing/freezing processes).

1.5 Sample Analysis Method 1.5.1 Experimental Instruments

- High performance liquid chromatography pump: Exion LC AD Pump, Sciex Company
- Auto sampler (Exion LC AD Autosampler, Sciex Company
- Column oven: Exion LC AD Column Oven, Sciex company
- Mass spectrometer: AB Sciex Qtrap 4500
- High-speed refrigerated centrifuge: Thermo Fisher, ST16R, GG1206085-093
- Electronic balance: Mettler Toledo, MS-105D, GG1206363
- Micro vortex: Shanghai Huxi Analytical Instrument Factory, WH-2, GG1206487

1.5.2 Experimental Materials: Mouse Plasma and Tissue 1.5.3 Analyte: L015

1.5.4 Internal Standard: Labetalol 1.5.5 Analytical Method: LC-MS Method 1.5.6 Mass Spectrometry Conditions:

1.5.6.1 Mass Spectrometry Parameters

- Ion source: Ion Electrospray (ESI)
- Ionization mode: positive ion mode (Positive)
- Monitoring mode: Multi-reaction monitoring (MRM)
- Ion Spray Voltage: 5,500
- Turbo Ion Spray Temp: 550° C.
- Curtain Gas: 35
- CAD Gas: Medium
- Nebulizing Gas, Gas1: 55.00
- Auxiliary Gas, Gas 2:55.00

1.5.6.2. Detection of Ion Pairs

| Compound | Molecular ion (m/z) | Fragment ion (m/z) | Residence time (msec) | Decluster voltage (DP) (V) | Collision energy (CE) (eV) |
|---|---|---|---|---|---|
| Labetalol | 329.2 | 294.3 | 15 | 80 | 27 |
| L015 | 442.2 | 406.2 | 30 | 97 | 36 |

1.5.7 Liquid Phase Method:

Chromatographic column: Agilent poroshell 120 EC-C18 (4.6×50 mm, 2.7 μm)

Mobile Phase A: 0.1% formic acid aqueous solution

Mobile Phase B: a solution of 0.1% formic acid in methanol

Rinse Port Wash Solution:methanol:water:acetonitrile: isopropanol=1:1:1:1

Column Temperature: 40° C.

Flow Rate: 0.8 mL/min

Sample Tray Temp: 15° C.

Injection Volume: 10 μL (L015)

Needle Stroke: 49 mm

Rinse Pump Setting: Rinse only the injection port

Rinse Mode: Rinse before inhalation

Rinse Volume: 500 μL

Rinse Dip Time: 2 seconds.

Elution gradient:

| Time (min) | Module | Function | Value (%) |
|---|---|---|---|
| 0.01 | Pumps | Pump B Conc. | 35 |
| 0.20 | Pumps | Pump B Conc. | 35 |
| 1.20 | Pumps | Pump B Conc. | 98 |
| 2.40 | Pumps | Pump B Conc. | 98 |
| 2.41 | Pumps | Pump B Conc. | 35 |
| 3.00 | System Controller | Stop | 35 |

1.5.8 Pre-Treatment Method:

Sample pretreatment process: 3 μL of working solution was taken, and 57 μL of blank matrix was added into a 1.5 mL of centrifuge tube, and then 240 μL of acetonitrile containing 200 ng/mL tolbutamide and labetalol mixed standard with 0.1% formic acid was added to precipitate protein. The sample was vortexed and mixed for 1 minute, and then centrifuged in 4° C. centrifuge at 13000 rpm for 15 minutes. 100 μL of supernatant was taken in another 96-well deep well plate, 100 μL of methanol:water (1:3, v: v) solution containing 0.1% FA was added, and the mixture was mixed with shaking for 1 min, and centrifuged at 3500 rpm for 5 min in a 96-well plate centrifuge and injected directly into the sample.

1.6 Data Analysis

The concentration of compound L015 in plasma and each tissue at each time point was calculated, and the data were analyzed.

1.7 Experimental Conclusion:

20% solutol was used as the vehicle, and after single intragastric administration of male CD-1 mice with compound L015 at a dose of 10 mg/kg: at 0.167 hours after intragastric administration, compound L015 was widely distributed in the liver (3260 ng/g) and kidney (1467 ng/g) (5.55 times and 2.50 times of the plasma concentration, respectively), compound L015 was less distributed in brain (0.05 times of the plasma concentration); at 1 hour and 10 hours after administration, compound L015 was still mainly distributed in the liver and kidney (4.53-5.05 times and 2.51-1.50 times of the plasma concentration, respectively), and the concentrations of compound L015 in brain were 161 ng/g and 25.9 ng/g (0.19-0.09 times of the plasma concentration, respectively), suggesting that L015 is less distributed in brain at 10 mg/kg, and see The FIGURE for more details. It shows that the compound of the present disclosure is mainly distributed in the liver and the target organ (kidney), and the high distribution of the compound in the target organ can reduce the dosage and reduce the safety risk.

The invention claimed is:

1. A heterocyclic compound represented by formula I, a tautomer thereof, a pharmaceutically acceptable salt thereof, a solvate thereof or a solvate of the pharmaceutically acceptable salt thereof:

(I)

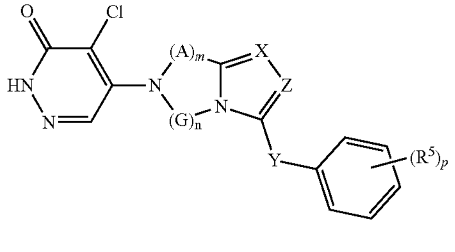

wherein, m is 1;

A is —($CR^1R^2$)—;

$R^1$ is independently hydrogen, halogen, $R^{1-1}$, $R^{1-2}$ substituted by one, two or more $R^{1-3}$, —(C═O)$NHR^{14}$, —NH(C═O)$R^{1-5}$, —(C═O)$OR^{1-6}$, —S(═O)$_2R^{1-7}$, or —S(═O)$R^{1-8}$;

$R^{1-1}$ and $R^{1-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, $C_6$-$C_{20}$ aryl-$C_1$-$C_{40}$ alkyl, 5- to 20-membered heteroaryl with 1, 2 or 3 heteroatoms selected from one or more of N, O and S, or 5- to 20-membered heteroaryl with 1, 2 or 3 heteroatoms selected from one or more of N, O and S —$C_1$-$C_{40}$ alkyl;

$R^{1-3}$, $R^{1-4}$, $R^{1-5}$, $R^{1-6}$, $R^{1-7}$ and $R^{1-8}$ are independently —CN, halogen, —OH, —$NH_2$, —COOH, —$NO_2$, —S(═O)$_2CH_3$, —C(═O)$NHCH_2CH_3$, oxo (═O), —NHC(═O)$R^{1-3-4}$, —C(═O)$OR^{1-3-5}$, $R^{1-3-1}$, or $R^{1-3-2}$ substituted by one, two or more $R^{1-3-3}$;

$R^{1-3-1}$ and $R^{1-3-2}$ are independently $C_1$-$C_{40}$ alkyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{1-3-3}$ is independently —CN, halogen, —OH, —$NH_2$, oxo (═O), —S(═O)$_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{1-3-4}$ is independently hydrogen, $R^{1-3-4-1}$, or $R^{1-3-4-2}$ substituted by one, two or more $R^{1-3-4-3}$;

$R^{1-3-4-1}$ and $R^{1-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{1-3-4-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{1-3-5}$ is independently hydrogen, $R^{1-3-5-1}$, or $R^{1-3-5-2}$ substituted by one, two or more $R^{1-3-5-3}$;

$R^{1-3-5-1}$ and $R^{1-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{1-3-5-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^2$ is independently hydrogen, halogen, $R^{2-1}$, $R^{2-2}$ substituted by one, two or more $R^{2-3}$, —(C=O)$NHR^{2-4}$, —NH(C=O)$R^{2-5}$, —(C=O)$OR^{2-6}$, —$S(=O)_2R^{2-7}$, or —S(=O)$R^{2-8}$;

$R^{2-1}$ and $R^{2-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, $C_6$-$C_{20}$ aryl-$C_1$-$C_{40}$ alkyl, 5- to 20-membered heteroaryl with 1, 2 or 3 heteroatoms selected from one or more of N, O and S, or 5- to 20-membered heteroaryl with 1, 2 or 3 heteroatoms selected from one or more of N, O and S —$C_1$-$C_{40}$ alkyl;

$R^{2-3}$, $R^{2-4}$, $R^{2-5}$, $R^{2-6}$, $R^{2-7}$ and $R^{2-8}$ are independently —CN, halogen, —OH, —$NH_2$, —COOH, —$NO_2$, —$S(=O)_2CH_3$, —C(=O)$NHCH_2CH_3$, oxo (=O), —NHC(=O)$R^{2-3-4}$, —C(=O)$OR^{2-3-5}$, $R^{2-3-1}$, or $R^{2-3-2}$ substituted by one, two or more $R^{2-3-3}$;

$R^{2-3-1}$ and $R^{2-3-2}$ are independently $C_1$-$C_{40}$ alkyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{2-3-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{2-3-4}$ is independently hydrogen, $R^{2-3-4-1}$, or $R^{2-3-4-2}$ substituted by one, two or more $R^{2-3-4-3}$;

$R^{2-3-4-1}$ and $R^{2-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{2-3-4-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{2-3-5}$ is independently hydrogen, $R^{2-3-5-1}$, or $R^{2-3-5-2}$ substituted by one, two or more $R^{2-3-5-3}$;

$R^{2-3-5-1}$ and $R^{2-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{2-3-5-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

n is 2;

G is —($CR^3R^4$)—;

$R^3$ is independently hydrogen, halogen, $R^{3-1}$, $R^{3-2}$ substituted by one, two or more $R^{3-3}$, —(C=O)$NHR^{3-4}$, —NH(C=O)$R^{3-5}$, —(C=O)$OR^{3-6}$, —$S(=O)_2R^{3-7}$, or —S(=O)$R^{3-8}$;

$R^{3-1}$ and $R^{3-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, $C_6$-$C_{20}$ aryl-$C_1$-$C_{40}$ alkyl, 5- to 20-membered heteroaryl with 1, 2 or 3 heteroatoms selected from one or more of N, O and S, or 5- to 20-membered heteroaryl with 1, 2 or 3 heteroatoms selected from one or more of N, O and S —$C_1$-$C_{40}$ alkyl;

$R^{3-3}$, $R^{3-4}$, $R^{3-5}$, $R^{3-6}$, $R^{3-7}$ and $R^{3-8}$ are independently —CN, halogen, —OH, —$NH_2$, —COOH, —$NO_2$, —$S(=O)_2CH_3$, —C(=O)$NHCH_2CH_3$, oxo (=O), —NHC(=O)$R^{3-3-4}$, —C(=O)$OR^{3-3-5}$, $R^{3-3-1}$, or $R^{3-3-2}$ substituted by one, two or more $R^{3-3-3}$;

$R^{3-3-1}$ and $R^{3-3-2}$ are independently $C_1$-$C_{40}$ alkyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{3-3-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{3-3-4}$ is independently hydrogen, $R^{3-3-4-1}$, or $R^{3-3-4-2}$ substituted by one, two or more $R^{3-3-4-3}$;

$R^{3-3-4-1}$ and $R^{3-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{3-3-4-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{3-3-5}$ is independently hydrogen, $R^{3-3-5-1}$, or $R^{3-3-5-2}$ substituted by one, two or more $R^{3-3-5-3}$;

$R^{3-3-5-1}$ and $R^{3-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{3-3-5-3}$ is independently —CN, halogen, —OH, —$NH_2$, oxo (=O), —$S(=O)_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^4$ is independently hydrogen, halogen, $R^{4-1}$, $R^{4-2}$ substituted by one, two or more $R^{4-3}$, —(C═O)NH$R^{4-4}$, —NH(C═O)$R^{4-5}$, —(C═O)O$R^{4-6}$, —S(═O)$_2R^{4-7}$, or —S(═O)$R^{4-8}$;

$R^{4-1}$ and $R^{4-2}$ are independently amino, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, $C_6$-$C_{20}$ aryl-$C_1$-$C_{40}$ alkyl, 5- to 20-membered heteroaryl with 1, 2 or 3 heteroatoms selected from one or more of N, O and S, or 5- to 20-membered heteroaryl with 1, 2 or 3 heteroatoms selected from one or more of N, O and S —$C_1$-$C_{40}$ alkyl;

$R^{4-3}$, $R^{4-4}$, $R^{4-5}$, $R^{4-6}$, $R^{4-7}$ and $R^{4-8}$ are independently —CN, halogen, —OH, —$NH_2$, —COOH, —$NO_2$, —S(═O)$_2CH_3$, —C(═O)NH$CH_2CH_3$, oxo (═O), —NHC(═O)$R^{4-3-4}$, —C(═O)O$R^{4-3-5}$, $R^{4-3-1}$, or $R^{4-3-2}$ substituted by one, two or more $R^{4-3-3}$;

$R^{4-3-1}$ and $R^{4-3-2}$ are independently $C_1$-$C_{40}$ alkyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{4-3-3}$ is independently —CN, halogen, —OH, —$NH_2$, oxo (═O), —S(═O)$_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{4-3-4}$ is independently hydrogen, $R^{4-3-4-1}$, or $R^{4-3-4-2}$ substituted by one, two or more $R^{4-3-4-3}$;

$R^{4-3-4-1}$ and $R^{4-3-4-2}$ are independently $C_1$-$C_{40}$ alkyl, $C_2$-$C_{40}$ alkenyl, $C_2$-$C_{40}$ alkynyl, $C_1$-$C_{40}$ alkoxy, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{4-3-4-3}$ is independently —CN, halogen, —OH, —$NH_2$, oxo (═O), —S(═O)$_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

$R^{4-3-5}$ is independently hydrogen, $R^{4-3-5-1}$, or $R^{4-3-5-2}$ substituted by one, two or more $R^{4-3-5-3}$;

$R^{4-3-5-1}$ and $R^{4-3-5-2}$ are independently $C_1$-$C_{40}$ alkyl, $C_2$-$C_{40}$ alkenyl, $C_2$-$C_{40}$ alkynyl, $C_3$-$C_{20}$ cycloalkyl, 3- to 20-membered heterocycloalkyl with 1, 2 or 3 heteroatoms selected from one or more of N, O and S, $C_6$-$C_{20}$ aryl, or 5- to 20-membered heteroaryl with 1, 2 or 3 heteroatoms selected from one or more of N, O and S;

$R^{4-3-5-3}$ is independently —CN, halogen, —OH, —$NH_2$, oxo (═O), —S(═O)$_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

X is N, Z is $CR^6$;

$R^6$ is hydrogen, halogen, amino, $C_1$-$C_4$ alkyl substituted by one or more $R^{6-2}$, $C_1$-$C_4$ alkoxy or —C(═O)—NH—$R^{6-1}$; $R^{6-1}$ is $C_1$-$C_4$ alkyl; $R^{6-2}$ is independently —CN, halogen, —OH, —$NH_2$, oxo (═O), —S(═O)$_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

Y is —O—, —S—, —$NR^8$—, —$CH_2$—, —C(═O)— or —S(═O)—;

$R^8$ is hydrogen, $C_1$-$C_4$ alkyl substituted by one or more $R^{8-2}$, $C_1$-$C_4$ alkoxy or —C(═O)—NH—$R^{8-1}$; $R^{8-1}$ is $C_1$-$C_4$ alkyl; $R^{8-2}$ is independently —CN, halogen, —OH, —$NH_2$, oxo (═O), —S(═O)$_2CH_3$, $C_1$-$C_{40}$ alkyl, $C_1$-$C_{40}$ alkyl substituted by one or more halogens, $C_1$-$C_{40}$ alkoxy, or $C_1$-$C_{40}$ alkoxy substituted by one or more halogens;

p is 1, 2 or 3;

$R^5$ is independently cyano, halogen, —OH, $C_1$-$C_4$ alkyl, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently H or $C_1$-$C_4$ alkyl.

2. The heterocyclic compound represented by formula I according to claim 1, the tautomer thereof, the pharmaceutically acceptable salt thereof, the solvate thereof or the solvate of the pharmaceutically acceptable salt thereof, wherein, $R^1$ is independently hydrogen or $R^{1-1}$; $R^{1-1}$ is $C_1$-$C_{40}$ alkyl;

or, $R^2$ is hydrogen;

or, $R^3$ is independently hydrogen, $R^{3-1}$, or $R^{3-2}$ substituted by one, two or more $R^{3-3}$; $R^{3-1}$ and $R^{3-2}$ are independently $C_1$-$C_{40}$ alkyl; $R^{3-3}$ is —OH;

or, $R^4$ is hydrogen;

or, X is N and Z is $CR^6$; $R^6$ is hydrogen, halogen or —C(═O)—NH—$R^{6-1}$; $R^{6-1}$ is $C_1$-$C_4$ alkyl;

or, Y is —$NR^8$—, —$CH_2$—, —C(═O)— or —S(═O)—; $R^8$ is hydrogen;

or, p is 1 or 2;

or, $R^5$ is independently cyano, halogen, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently H, methyl or ethyl.

3. The heterocyclic compound represented by formula I according to claim 2, the tautomer thereof, the pharmaceutically acceptable salt thereof, the solvate thereof or the solvate of the pharmaceutically acceptable salt thereof, wherein, $R^1$ is hydrogen;

or, $R^3$ is hydrogen;

or, X is N and Z is $CR^6$; $R^6$ is hydrogen;

or, Y is —$CH_2$— or —C(═O)—;

or, $R^5$ is independently cyano, halogen, or $C_1$-$C_4$ alkyl substituted by one or more halogens.

4. The heterocyclic compound represented by formula I according to claim 1, the tautomer thereof, the pharmaceutically acceptable salt thereof, the solvate thereof or the solvate of the pharmaceutically acceptable salt thereof, wherein, $R^1$ is independently hydrogen or $R^{1-1}$; $R^{1-1}$ is independently methyl or ethyl;

or, $R^3$ is independently hydrogen, $R^{3-1}$ or $R^{3-2}$ substituted by one, two or more $R^{3-3}$; $R^{3-1}$ and $R^{3-2}$ are independently methyl or ethyl; $R^{3-3}$ is —OH;

or, Y is —O—, —S—, —$NR^8$—, —$CH_2$—, —C(═O)— or —S(═O)—; $R^8$ is hydrogen;

or, $R^5$ is independently cyano, halogen, —OH, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently $C_1$-$C_4$ alkyl.

5. The heterocyclic compound represented by formula I according to claim 1, the tautomer thereof, the pharmaceutically acceptable salt thereof, the solvate thereof or the solvate of the pharmaceutically acceptable salt thereof, wherein, the heterocyclic compound is as described in any one of the following schemes:

scheme 1:

m is 1;

A is —($CR^1R^2$)—;

$R^1$ is independently hydrogen or $R^{1-1}$; $R^{1-1}$ is independently $C_1$-$C_{40}$ alkyl;
$R^2$ is hydrogen;
n is 2;
G is —($CR^3R^4$)—;
$R^3$ is independently hydrogen, $R^{3-1}$, or $R^{3-2}$ substituted by one, two or more $R^{3-3}$; $R^{3-1}$ and $R^{3-2}$ are independently $C_1$-$C_{40}$ alkyl; $R^{3-3}$ is —OH;
$R^4$ is hydrogen;
X is N and Z is $CR^6$;
$R^6$ is hydrogen, halogen or —C(═O)—NH—$R^{6-1}$; $R^{6-1}$ is $C_1$-$C_4$ alkyl;
Y is —$NR^8$— or —$CH_2$—; $R^8$ is hydrogen;
p is 1 or 2;
$R^5$ is independently halogen, or $C_1$-$C_4$ alkyl substituted by one or more halogens;
scheme 2:
m is 1;
A is —($CR^1R^2$)—;
$R^1$ is hydrogen;
$R^2$ is hydrogen;
n is 2;
G is —($CR^3R^4$)—;
$R^3$ is hydrogen;
$R^4$ is hydrogen;
X is N and Z is $CR^6$;
$R^6$ is hydrogen, halogen or —C(═O)—NH—$R^{6-1}$; $R^{6-1}$ is $C_1$-$C_4$ alkyl;
Y is —$NR^8$— or —$CH_2$—; $R^8$ is hydrogen;
p is 1 or 2;
$R^5$ is independently halogen, or $C_1$-$C_4$ alkyl substituted by one or more halogens;
scheme 3:
m is 1;
A is —($CR^1R^2$)—;
$R^1$ is hydrogen;
$R^2$ is hydrogen;
n is 2;
G is —($CR^3R^4$)—;
$R^3$ is hydrogen;
$R^4$ is hydrogen;
X is N and Z is $CR^6$;
$R^6$ is hydrogen;
Y is —$CH_2$—;
p is 1 or 2;
$R^5$ is independently halogen, or $C_1$-$C_4$ alkyl substituted by one or more halogens;
scheme 4:
m is 1;
A is —($CR^1R^2$)—;
$R^1$ is independently hydrogen or $R^{1-1}$; $R^{1-1}$ is independently $C_1$-$C_{40}$ alkyl;
$R^2$ is hydrogen;
n is 2;
G is —($CR^3R^4$)—;
$R^3$ is independently hydrogen, $R^{3-1}$, or $R^{3-2}$ substituted by one, two or more $R^{3-3}$; $R^{3-1}$ and $R^{3-2}$ are independently $C_1$-$C_{40}$ alkyl; $R^{3-3}$ is —OH;
$R^4$ is hydrogen;
X is N and Z is $CR^6$;
$R^6$ is hydrogen, halogen or —C(═O)—NH—$R^{6-1}$; $R^{6-1}$ is $C_1$-$C_4$ alkyl;
Y is —$NR^8$—, —$CH_2$—, —C(═O)— or —S(═O)—; $R^8$ is hydrogen;
p is 1 or 2;
$R^5$ is independently cyano, halogen, —OH, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently $C_1$-$C_4$ alkyl;
scheme 5:
m is 1;
A is —($CR^1R^2$)—;
$R^1$ is independently hydrogen or $R^{1-1}$; $R^{1-1}$ is independently methyl or ethyl;
$R^2$ is hydrogen;
n is 2;
G is —($CR^3R^4$)—;
$R^3$ is independently hydrogen, $R^{3-1}$, or $R^{3-2}$ substituted by one, two or more $R^{3-3}$; $R^{3-1}$ and $R^{3-2}$ are independently methyl or ethyl; $R^{3-3}$ is —OH;
$R^4$ is hydrogen;
X is N and Z is $CR^6$;
$R^6$ is hydrogen, halogen or —C(═O)—NH—$R^{6-1}$; $R^{6-1}$ is methyl or ethyl;
Y is —$NR^8$—, —$CH_2$—, —C(═O)— or —S(═O)—; $R^8$ is hydrogen;
p is 1 or 2;
$R^5$ is independently cyano, halogen, —OH, methoxy, ethoxy, —$NR^9R^{10}$, cyclopropyl or methyl substituted by one or more halogens; $R^9$ and $R^{10}$ are independently methyl or ethyl;
scheme 6:
m is 1;
A is —($CR^1R^2$)—;
$R^1$ is hydrogen;
$R^2$ is hydrogen;
n is 2;
G is —($CR^3R^4$)—;
$R^3$ is hydrogen;
$R^4$ is hydrogen;
X is N and Z is $CR^6$;
$R^6$ is hydrogen;
Y is —$CH_2$—, —C(═O)— or —S(═O)—;
p is 1 or 2;
$R^5$ is independently halogen, cyano, —OH, or $C_1$-$C_4$ alkyl substituted by one or more halogens;
scheme 7:
m is 1;
A is —($CR^1R^2$)—;
$R^1$ is hydrogen;
$R^2$ is hydrogen;
n is 2;
G is —($CR^3R^4$)—;
$R^3$ is hydrogen;
$R^4$ is hydrogen;
X is N and Z is $CR^6$;
$R^6$ is hydrogen;
Y is —$CH_2$—, —C(═O)— or —S(═O)—;
p is 1 or 2;
$R^5$ is independently halogen, cyano, —OH, or $C_1$-$C_4$ alkyl substituted by one or more halogens; when p is 1, $R^5$ is $C_1$-$C_4$ alkyl substituted by one or more halogens; when p is 2, the $C_1$-$C_4$ alkyl substituted by one or more halogens is $C_1$-$C_4$ alkyl substituted by 3 halogens;
scheme 9:
the structure of the heterocyclic compound represented by formula I is represented by formula IV or formula V:

IV

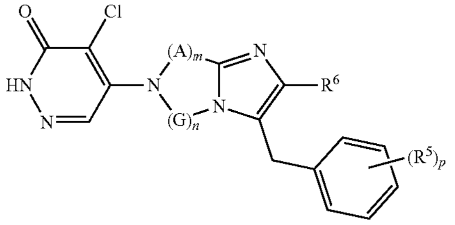

or

V

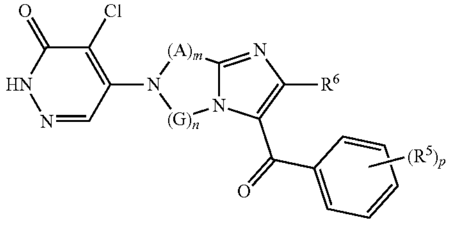

scheme 10:

the structure of the heterocyclic compound represented by formula I is represented by formula VI or formula VII:

VI

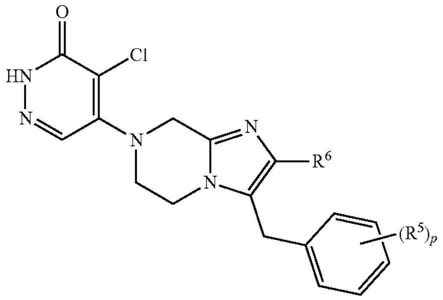

or

VII

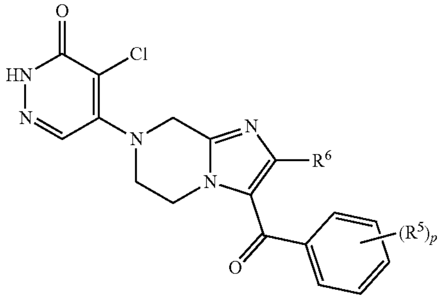

scheme 11:

m is 1;

A is —($CR^1R^2$)—;

$R^1$ is independently hydrogen or $R^{1-1}$; $R^{1-1}$ is $C_1$-$C_{40}$ alkyl;

$R^2$ is hydrogen;

n is 2;

G is —($CR^3R^4$)—;

$R^3$ is independently hydrogen, $R^{3-1}$, or $R^{3-2}$ substituted by one, two or more $R^{3-3}$; $R^{3-1}$ and $R^{3-2}$ are independently $C_1$-$C_{40}$ alkyl; $R^{3-3}$ is —OH;

$R^4$ is hydrogen;

X is N, Z is $CR^6$;

$R^6$ is hydrogen, halogen or —C(═O)—NH—$R^{6-1}$; $R^{6-1}$ is $C_1$-$C_4$ alkyl;

Y is —O—, —S—, —$NR^8$—, —$CH_2$—, —C(═O)— or —S(═O)—; $R^8$ is hydrogen;

p is 1 or 2;

$R^5$ is independently cyano, halogen, —OH, $C_1$-$C_4$ alkyl, $C_1$-$C_4$ alkoxy, —$NR^9R^{10}$, $C_3$-$C_6$ cycloalkyl, or $C_1$-$C_4$ alkyl substituted by one or more halogens; $R^9$ and $R^{10}$ are independently $C_1$-$C_4$ alkyl;

scheme 12:

m is 1;

A is —($CR^1R^2$)—;

$R^1$ is independently hydrogen or $R^{1-1}$; $R^{1-1}$ is independently methyl or ethyl;

$R^2$ is hydrogen;

n is 2;

G is —($CR^3R^4$)—;

$R^3$ is independently hydrogen, $R^{3-1}$, or $R^{3-2}$ substituted by one, two or more $R^{3-3}$; $R^{3-1}$ and $R^{3-2}$ are independently methyl or ethyl; $R^{3-3}$ is —OH;

$R^4$ is hydrogen;

X is N and Z is $CR^6$;

$R^6$ is hydrogen, halogen or —C(═O)—NH—$R^{6-1}$; $R^{6-1}$ is methyl or ethyl;

Y is —O—, —S—, —$NR^8$—, —$CH_2$—, —C(═O)— or —S(═O)—; $R^8$ is hydrogen;

p is 1 or 2;

$R^5$ is independently cyano, halogen, —OH, methoxy, ethoxy, —$NR^9R^{10}$, cyclopropyl, methyl, difluoromethyl or trifluoromethyl; $R^9$ and $R^{10}$ are independently methyl or ethyl;

scheme 13:

m is 1;

A is —($CR^1R^2$)—;

$R^1$ is hydrogen;

$R^2$ is hydrogen;

n is 2;

G is —($CR^3R^4$)—;

$R^3$ is hydrogen;

$R^4$ is hydrogen;

X is N and Z is $CR^6$;

$R^6$ is hydrogen;

Y is —$CH_2$— or —C(═O)—;

p is 1 or 2;

$R^5$ is independently halogen, cyano, or methyl substituted by one or more halogens;

when p is 2, the $R^5$ is located at the ortho and para positions of the Y, and the methyl substituted by one or more halogens is methyl substituted by 3 halogens;

when Y is —$CH_2$— and p is 1, $R^5$ is methyl substituted by one or more halogens.

6. The heterocyclic compound represented by formula I according to claim 1, the tautomer thereof, the pharmaceutically acceptable salt thereof, the solvate thereof or the solvate of the pharmaceutically acceptable salt thereof, wherein, when A is independently —($CR^1R^2$)—, the carbon atoms connected to $R^1$ and $R^2$ are carbon atoms of R-configuration or carbon atoms of S-configuration;

or, when $R^{1-1}$ is $C_1$-$C_{40}$ alkyl, the $C_1$-$C_{40}$ alkyl is $C_1$-$C_4$ alkyl;

or, when G is —($CR^3R^4$)—, wherein, the carbon atoms connected to $R^3$ and $R^4$ are carbon atoms of R-configuration or carbon atoms of S-configuration;

or, when $R^{3-1}$ is $C_1$-$C_{40}$ alkyl, the $C_1$-$C_{40}$ alkyl is $C_1$-$C_4$ alkyl;

or, when $R^{3-2}$ is $C_1$-$C_{40}$ alkyl, the $C_1$-$C_{40}$ alkyl is $C_1$-$C_4$ alkyl;

or, when $R^6$ is halogen, the halogen is fluorine, chlorine or bromine;

or, when $R^{6-1}$ is $C_1$-$C_4$ alkyl, the $C_1$-$C_4$ alkyl is methyl, ethyl, n-propyl, isopropyl, n-butyl, isobutyl, sec-butyl or tert-butyl;

or, the $R^5$ is independently located at the ortho, meta or para position of the Y;

or, when $R^5$ is independently halogen, the halogen is fluorine, chlorine or bromine;

or, when $R^5$ is independently $C_1$-$C_4$ alkyl substituted by one or more halogens, the number of the more halogens is 2 or 3;

or, when $R^5$ is independently $C_1$-$C_4$ alkyl substituted by one or more halogens, the halogen is fluorine, chlorine or bromine;

or, when $R^5$ is independently $C_1$-$C_4$ alkyl substituted by one or more halogens, the $C_1$-$C_4$ alkyl is methyl, ethyl, n-propyl, isopropyl, n-butyl, isobutyl, sec-butyl or tert-butyl.

7. The heterocyclic compound represented by formula I according to claim 6, the tautomer thereof, the pharmaceutically acceptable salt thereof, the solvate thereof or the solvate of the pharmaceutically acceptable salt thereof, wherein, when $R^{1-1}$ is $C_1$-$C_{40}$ alkyl, the $C_1$-$C_{40}$ alkyl is methyl or ethyl;

or, when $R^{3-1}$ is $C_1$-$C_{40}$ alkyl, the $C_1$-$C_{40}$ alkyl is methyl or ethyl;

or, when $R^{3-2}$ is $C_1$-$C_{40}$ alkyl, the $C_1$-$C_{40}$ alkyl is methyl or ethyl;

or, when $R^6$ is halogen, the halogen is bromine;

or, when $R^{6-1}$ is $C_1$-$C_4$ alkyl, the $C_1$-$C_4$ alkyl is methyl;

or, when p is 1, the $R^5$ is located at the ortho position of the Y;

or, when p is 2, the $R^5$ is located at the ortho or para position of the Y;

or, when $R^5$ is independently halogen, the halogen is fluorine or chlorine;

or, when $R^5$ is independently $C_1$-$C_4$ alkyl substituted by more halogens, the $C_1$-$C_4$ alkyl substituted by more halogens is difluoromethyl or trifluoromethyl.

8. The heterocyclic compound represented by formula I according to claim 1, the tautomer thereof, the pharmaceutically acceptable salt thereof, the solvate thereof or the solvate of the pharmaceutically acceptable salt thereof, wherein, when p is 2, the $R^5$ is independently located at the ortho or para position of the Y, or is located at the ortho or meta position of the Y;

or, the 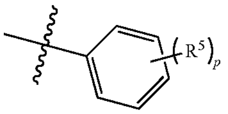 is

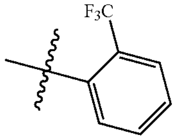, 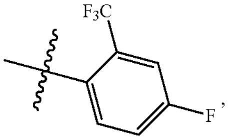,

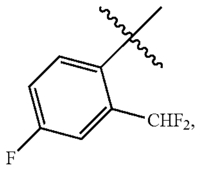 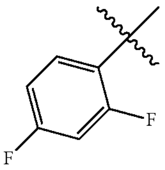,

-continued

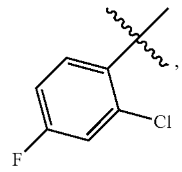, 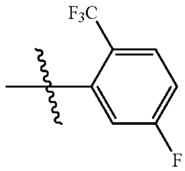,

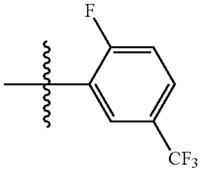 or 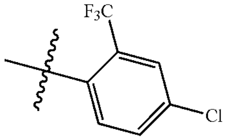,

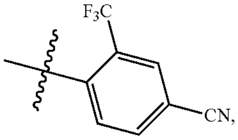 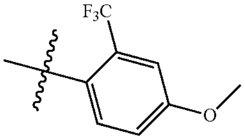,

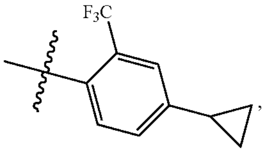

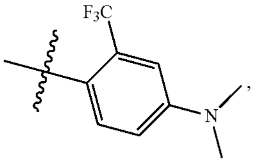 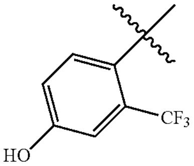,

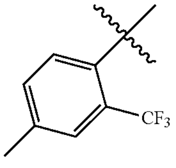 or 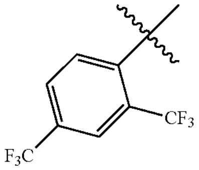;

or, the 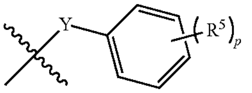 is

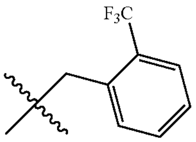, 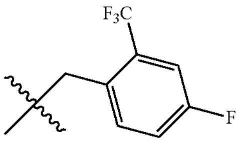

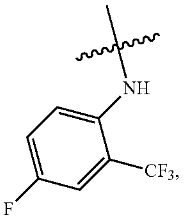 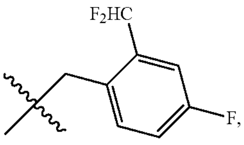

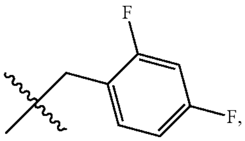 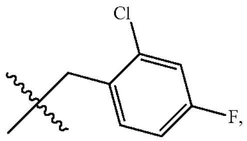

-continued
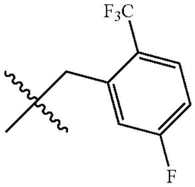,
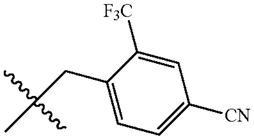,
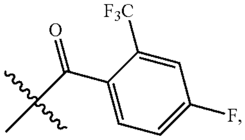
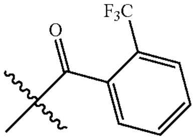,
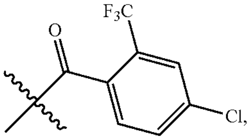
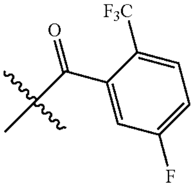,
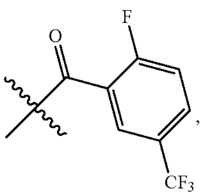,
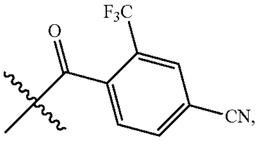
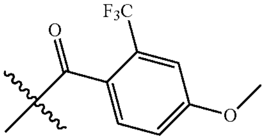,
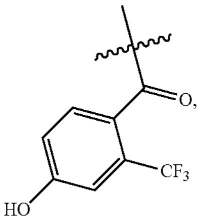
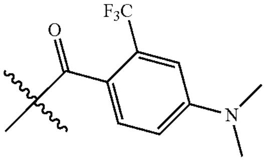,
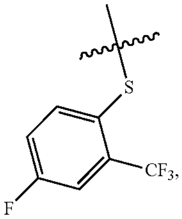
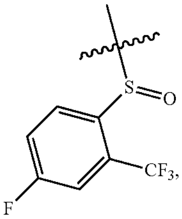
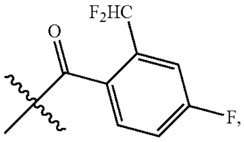
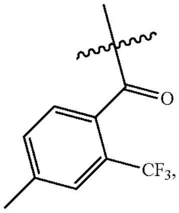
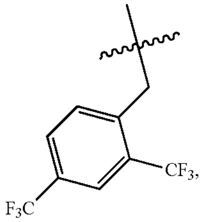
-continued
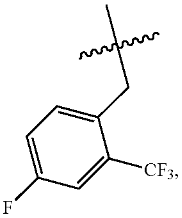
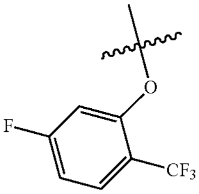 or
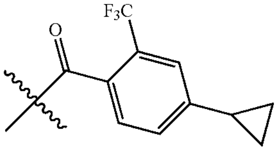.
9. The heterocyclic compound represented by formula I according to claim 8, the tautomer thereof, the pharmaceutically acceptable salt thereof, the solvate thereof or the solvate of the pharmaceutically acceptable salt thereof, wherein,
the 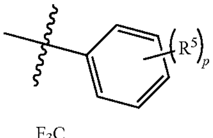 is 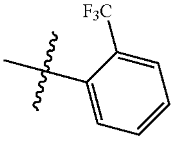,
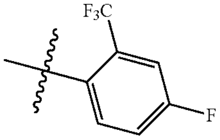 or
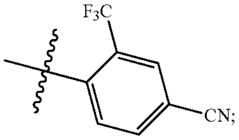 or,
the 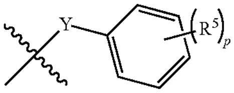 is
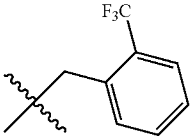,
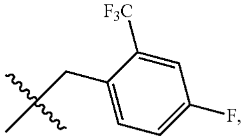
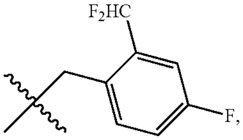
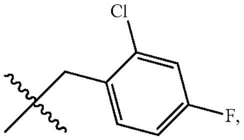
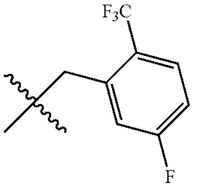,
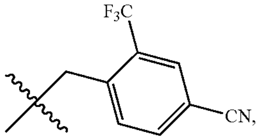

-continued

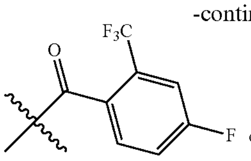 or 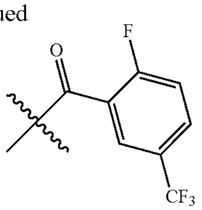 .

10. The heterocyclic compound represented by formula I according to claim 7, the tautomer thereof, the pharmaceutically acceptable salt thereof, the solvate thereof or the solvate of the pharmaceutically acceptable salt thereof, wherein, when $R^3$ is independently $R^{3-2}$ substituted by one $R^{3-3}$, the $R^{3-2}$ substituted by one $R^{3-3}$ is hydroxymethyl;

or, the

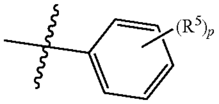

is 2-trifluoromethylphenyl, 2-trifluoromethyl-4-fluorophenyl, 2-difluoromethyl-4-fluorophenyl, 2,4-difluorophenyl or 2-chloro-4-fluorophenyl,

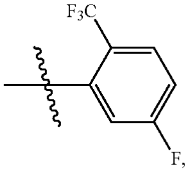 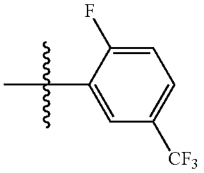

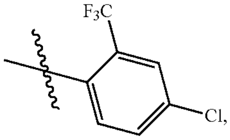 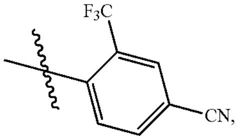

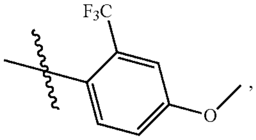 ,

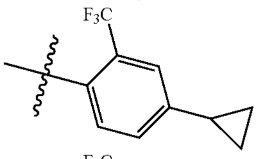 or

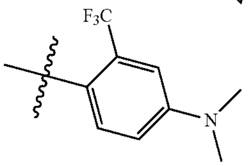 ; or, the 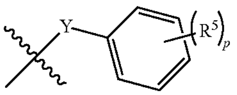 is

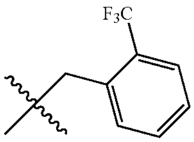 , 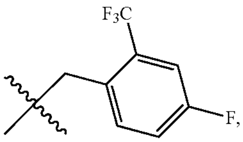

-continued

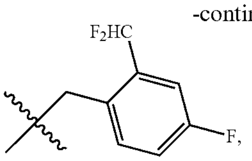 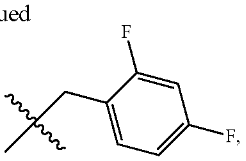

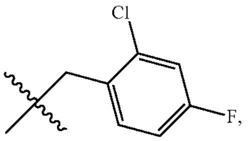 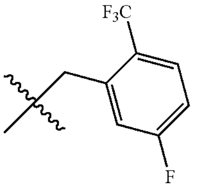 ,

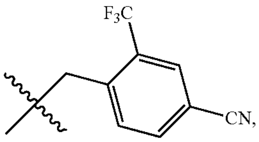 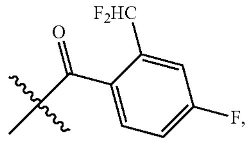

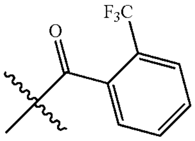 , 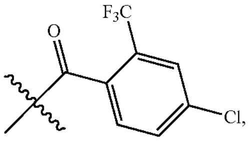

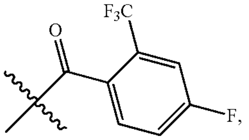 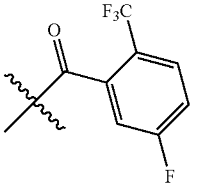 ,

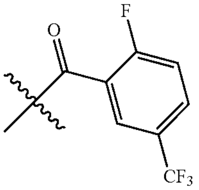 , 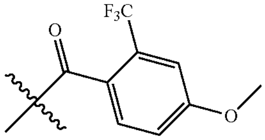 ,

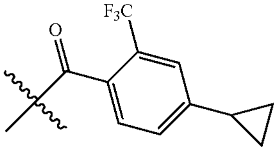 ,

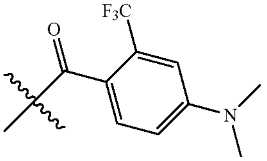 ,

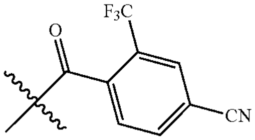 or

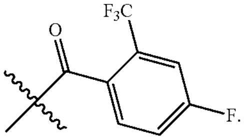

11. The heterocyclic compound represented by formula I according to claim 10, the tautomer thereof, the pharmaceutically acceptable salt thereof, the solvate thereof or the solvate of the pharmaceutically acceptable salt thereof, wherein, the

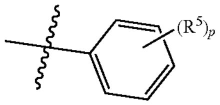

is 2-trifluoromethylphenyl, 2-trifluoromethyl-4-fluorophenyl, 2-difluoromethyl-4-fluorophenyl, 2,4-difluorophenyl, 2-chloro-4-fluorophenyl

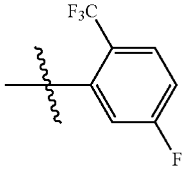

or

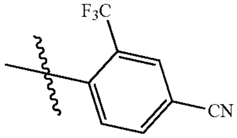

; or, the

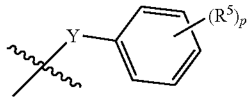

is

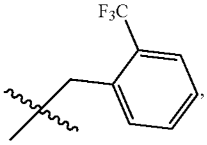

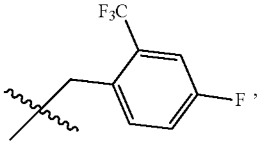

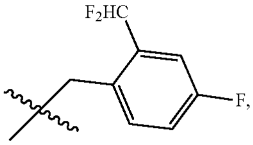

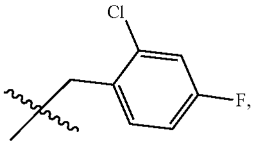

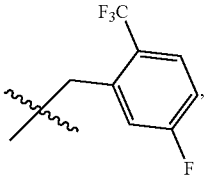

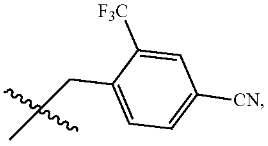

or

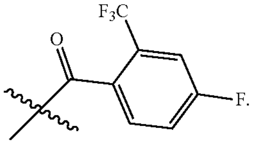

12. The heterocyclic compound represented by formula I according to claim 1, the tautomer thereof, the pharmaceutically acceptable salt thereof, the solvate thereof or the solvate of the pharmaceutically acceptable salt thereof, wherein, the heterocyclic compound represented by formula I is any one of the following compounds:

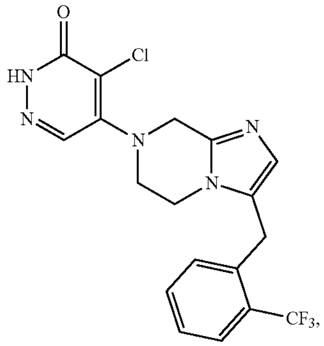

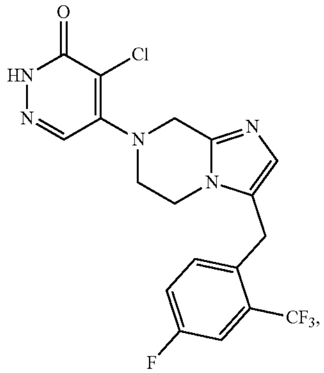

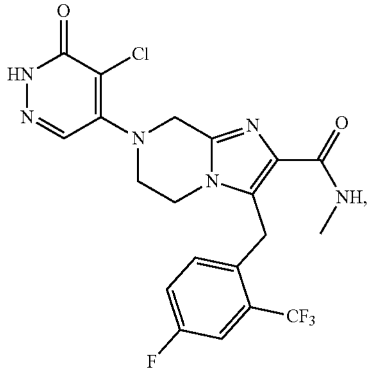

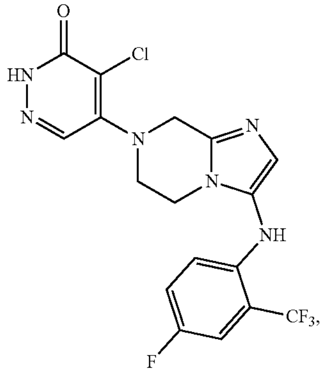

-continued
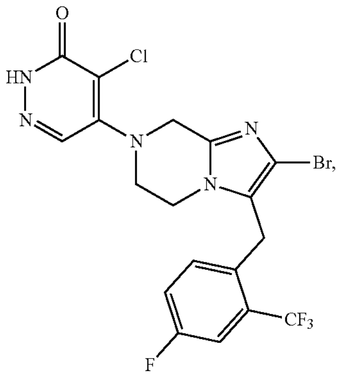
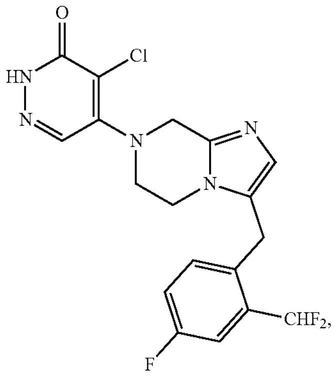
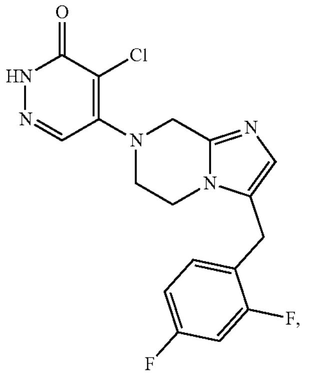
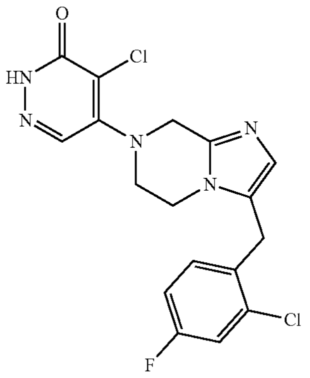
-continued
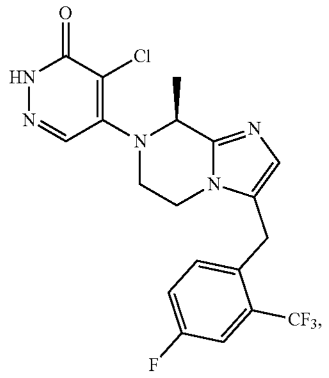
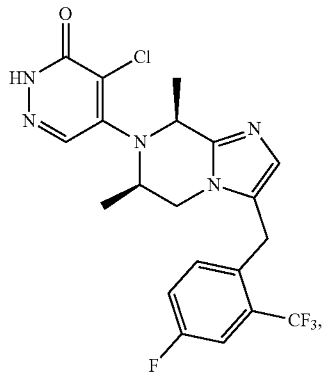
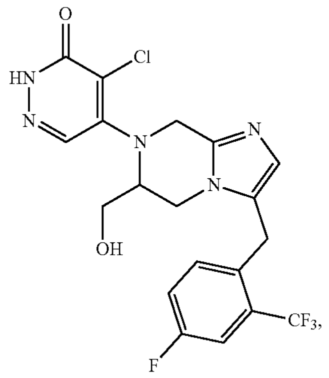
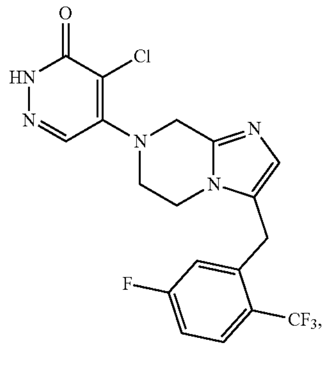

-continued
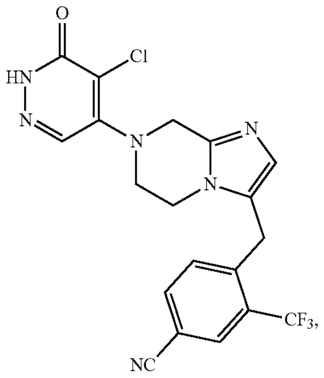
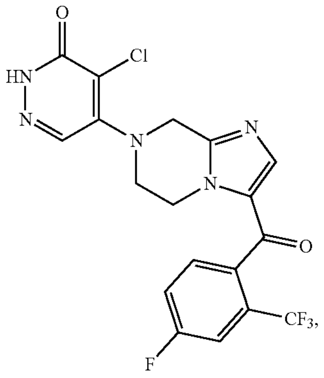
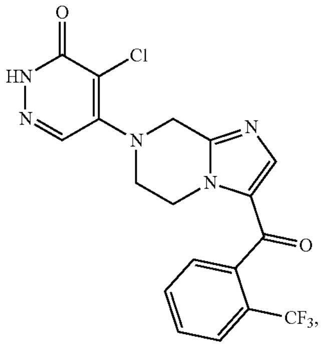
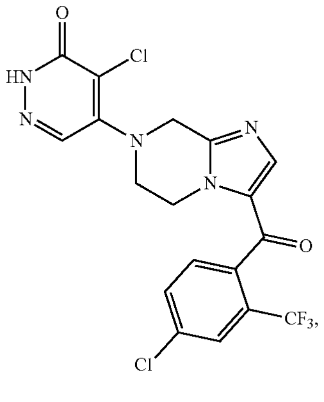
-continued
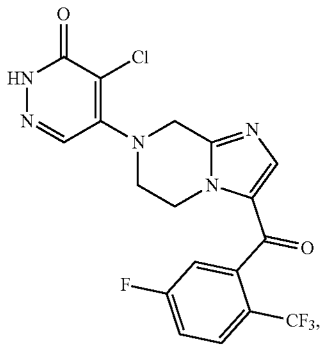
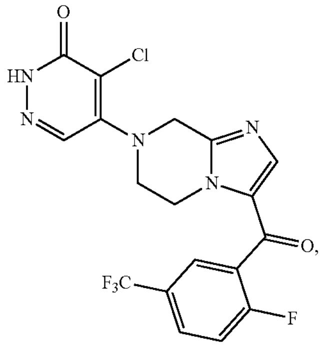
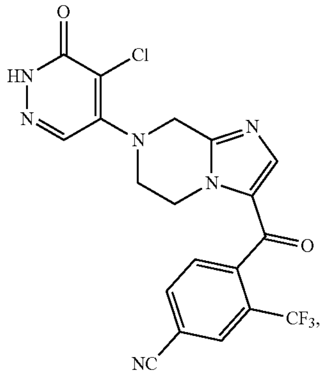
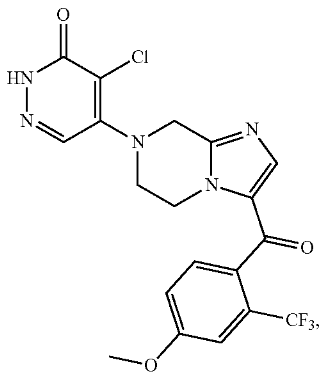

-continued
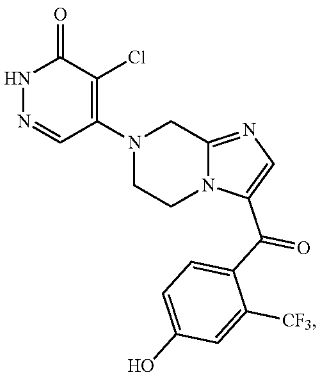
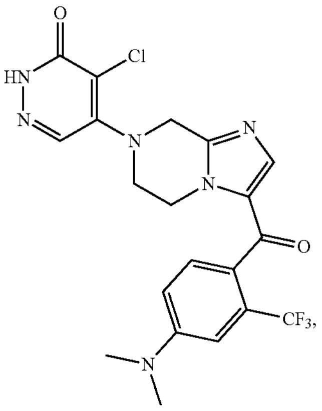
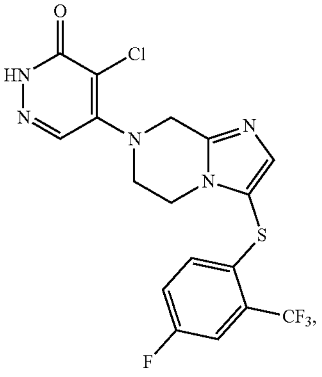
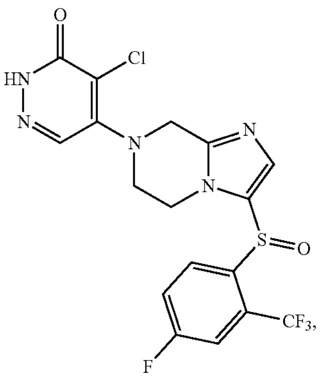
-continued
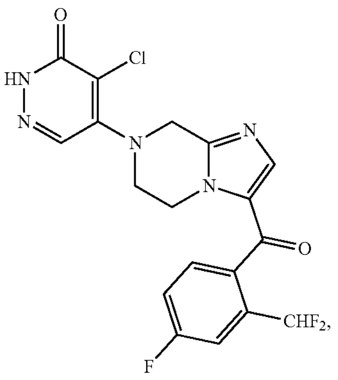
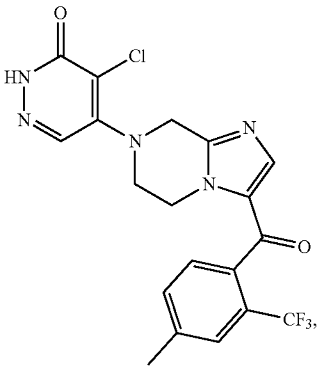
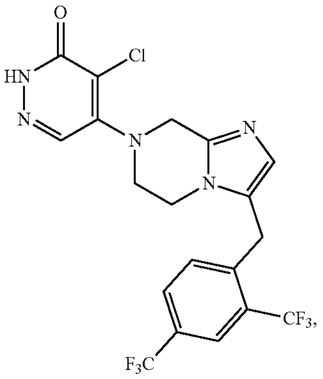
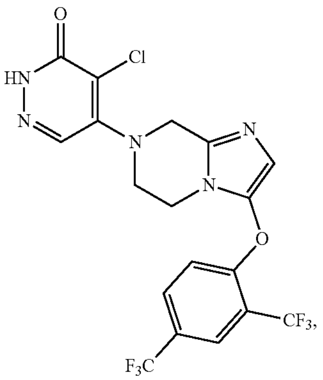

-continued

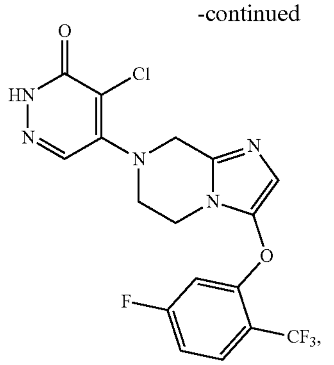

and

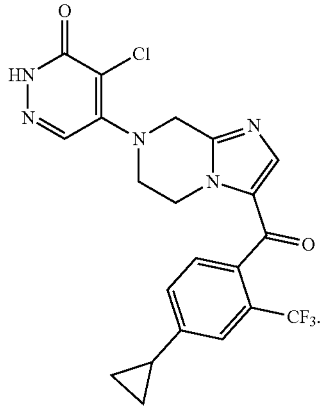 [SMILES: O=C(c1ccc(C2CC2)cc1C(F)(F)F)c1cnc2n1CCN(c1cn[nH]c(=O)c1Cl)C2]

13. A pharmaceutical composition, comprising substance Y and pharmaceutical excipients, the substance Y is the heterocyclic compound represented by formula I according to claim 1, the tautomer thereof, the pharmaceutically acceptable salt thereof, the solvent thereof or the solvent of the pharmaceutically acceptable salt thereof.

14. A method for inhibiting TRPC5 in a subject in need thereof, comprising: administering an effective amount of substance Y to the subject, the substance Y is the heterocyclic compound represented by formula I according to claim 1, the tautomer thereof, the pharmaceutically acceptable salt thereof, the solvate thereof or the solvent of the pharmaceutically acceptable salt thereof.

15. A method for treating a TRPC5-mediated disease in a subject in need thereof, comprising: administering an effective amount of substance Y to the subject, the substance Y is the heterocyclic compound represented by formula I according to claim 1, the tautomer thereof, the pharmaceutically acceptable salt thereof, the solvate thereof or the solvent of the pharmaceutically acceptable salt thereof.

16. The method according to claim 15, the TRPC5-mediated disease is psychiatric condition, neurological condition, neurodegenerative condition or nephropathy;

the psychiatric condition, neurological condition or neurodegenerative condition can be selected from: borderline personality disorder, depression, post-traumatic stress disorder, panic disorder, agoraphobia, social phobia, generalized anxiety disorder, panic disorder, social anxiety disorder, obsessive-compulsive disorder, separation anxiety amnesia, aphasia, brain injury, brain tumor, chronic fatigue syndrome, Creutzfeldt-Jakob disease, dissociative amnesia, fugue amnesia, learning disorder, sleeping disorder, multiple personality disorder, pain, post-traumatic stress disorder, schizophrenia, sports injury, stroke, Wernicke-Korsakoff Syndrome, Alzheimer's disease, Parkinson's disease, Huntington's disease, amyotrophic lateral sclerosis or epilepsy;

the nephropathy can be focal segmental glomerulosclerosis, minimal change nephropathy or diabetic nephropathy.

17. A method for treating psychiatric condition, neurological condition, neurodegenerative condition or nephropathy in a subject in need thereof, comprising: administering an effective amount of substance Y to the subject, the substance Y is the heterocyclic compound represented by formula I according to claim 1, the tautomer thereof, the pharmaceutically acceptable salt thereof, the solvent thereof, or the solvent of the pharmaceutically acceptable salt thereof.

18. The method according to claim 17, the psychiatric condition, neurological condition or neurodegenerative condition is selected from: borderline personality disorder, depression, post-traumatic stress disorder, panic disorder, agoraphobia, social phobia, generalized anxiety disorder, panic disorder, social anxiety disorder, obsessive-compulsive disorder, separation anxiety amnesia, aphasia, brain injury, brain tumor, chronic fatigue syndrome, Creutzfeldt-Jakob disease, dissociative amnesia, fugue amnesia, learning disorder, sleeping disorder, multiple personality disorder, pain, post-traumatic stress disorder, schizophrenia, sports injury, stroke, Wernicke-Korsakoff Syndrome, Alzheimer's disease, Parkinson's disease, Huntington's disease, amyotrophic lateral sclerosis or epilepsy;

or, the nephropathy is focal segmental glomerulosclerosis, minimal change nephropathy or diabetic nephropathy.

19. The method according to claim 16, wherein the depression is selected from major depression, major depressive disorder, psychiatric depression, dysthymia and postpartum depression, and bipolar disorder.

20. The method according to claim 18, wherein the depression is selected from major depression, major depressive disorder, psychiatric depression, dysthymia and postpartum depression, and bipolar disorder.

21. The heterocyclic compound represented by formula I according to claim 1, the tautomer thereof, the pharmaceutically acceptable salt thereof, the solvate thereof or the solvate of the pharmaceutically acceptable salt thereof, wherein $R^5$ is independently cyano, halogen, —OH, methoxy, ethoxy, —$N(CH_3)_2$, cyclopropyl, methyl, difluoromethyl or trifluoromethyl.

* * * * *